United States Patent
Gibson et al.

(10) Patent No.: US 12,312,330 B2
(45) Date of Patent: May 27, 2025

(54) 1-((S)-1-(3-CHLORO-5-FLUORO-2-((4-(1H-PYRAZOL-1-YL)-2-METHYLQUINOLIN-8-YLOXY)METHYL)PHENYL)ETHYL)-IMIDAZOLIDINE-2,4-DIONE DERIVATIVES AND RELATED COMPOUNDS AS BRADYKININ (BK) B2 RECEPTOR ANTAGONIST FOR TREATING SKIN DISEASES

(71) Applicant: Pharvaris GmbH, Zug (CH)

(72) Inventors: Christoph Gibson, Berlin (DE); Joern Saupe, Potsdam (DE); Horst-Dieter Ambrosi, Berlin (DE); Lars Ole Haustedt, Falkensee (DE)

(73) Assignee: Pharvaris GmbH, Zug (CH)

( * ) Notice: Subject to any disclaimer, the term of this patent is extended or adjusted under 35 U.S.C. 154(b) by 734 days.

(21) Appl. No.: 17/530,967

(22) PCT Filed: May 25, 2020

(86) PCT No.: PCT/EP2020/064375
§ 371 (c)(1),
(2) Date: Nov. 19, 2021

(87) PCT Pub. No.: WO2020/234479
PCT Pub. Date: Nov. 26, 2020

(65) Prior Publication Data
US 2022/0135542 A1    May 5, 2022

(30) Foreign Application Priority Data
May 23, 2019 (EP) .................................. 19176207

(51) Int. Cl.
C07D 401/14    (2006.01)
A61K 31/4709   (2006.01)
A61K 31/496    (2006.01)

(52) U.S. Cl.
CPC ........ *C07D 401/14* (2013.01); *A61K 31/4709* (2013.01); *A61K 31/496* (2013.01)

(58) Field of Classification Search
CPC . C07D 401/14; A61K 31/4709; A61K 31/496
USPC .................................................. 514/253.06
See application file for complete search history.

(56) References Cited

FOREIGN PATENT DOCUMENTS

| WO | WO-2008/116620 A1 | 10/2008 | | |
|----|-------------------|---------|--|--|
| WO | WO-2010031589 A1 * | 3/2010 | ................ | A61P 1/00 |
| WO | WO-2014159637 A1 * | 10/2014 | ........... | A61K 31/185 |
| WO | WO-2019/101906 A1 | 5/2019 | | |

OTHER PUBLICATIONS

Gibson et al., "Novel small molecule bradykinin B2 receptor antagonists," J Med Chem. 52(14):4370-9 (Jul. 2009).
Wermuth, Chapter 13: Molecular Conversion based on Isosteric Substitution. *The Practice of Medicinal Chemistry.* vol 1. Technomics, Inc. 235-271 (1998) (38 pages).
Nozaki et al., *Medicinal Chemistry.* Kagaku-Dojin Publishing Company, Inc., 98-99 (1995).
Lesage et al., "In Vitro Pharmacological Profile of a New Small Molecule Bradykinin B2 Receptor Antagonist," Front Pharmacol. 11:916 (Jun. 2020) (16 pages).

* cited by examiner

*Primary Examiner* — Yevgeny Valenrod
(74) *Attorney, Agent, or Firm* — Clark & Elbing LLP

(57) ABSTRACT

The invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to said compound(s) for use as in a method of treating a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; or edema.

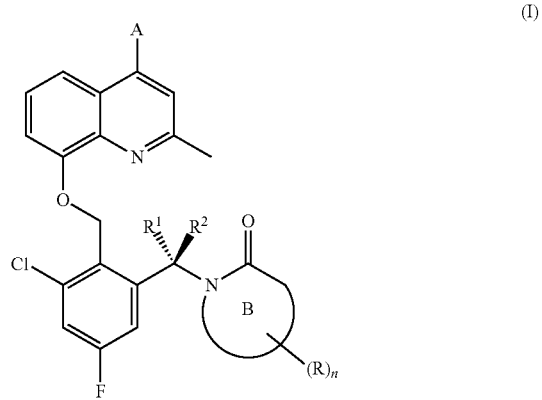

12 Claims, No Drawings

1-((S)-1-(3-CHLORO-5-FLUORO-2-((4-(1H-PYRAZOL-1-YL)-2-METHYLQUINOLIN-8-YLOXY)METHYL)PHENYL)ETHYL)-IMIDAZOLIDINE-2,4-DIONE DERIVATIVES AND RELATED COMPOUNDS AS BRADYKININ (BK) B2 RECEPTOR ANTAGONIST FOR TREATING SKIN DISEASES

FIELD OF THE INVENTION

This invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to uses of said compound(s), including the use as a medicament.

BACKGROUND OF THE INVENTION

BK is a peptide hormone that participates in inflammatory processes by activation of endothelial cells leading to vasodilation, increased vascular permeability, production of nitric oxide, and mobilization of arachidonic acid. BK also stimulates sensory nerve endings causing a burning dysaesthesia. Thus, the classical parameters of inflammation (e.g. redness, heat, swelling and pain) can all result from BK formation. BK is a short-lived component of the kallikrein-kinin system. The concentration of circulating BK is maintained at a low level under normal physiological conditions and may be rapidly increased under pathological situations by the enzymatic degradation of the circulating glycoprotein precursors called kininogens. The two most potent kininogen-metabolising enzymes are the trypsin-like serine proteases plasma kallikrein and tissue kallikrein. The precursors of these enzymes are normally present in all tissues and are ready to be activated by physiological or pathophysiological processes. (Sainz, I. M. et al Thromb. Haemost. 2007, 98, 77-83). The BK B2 receptor is constitutively expressed in most cell and tissue types and mediates most of the known effects of BK when this is produced in plasma or tissues. (Regoli, D. et al Pharmacol. Rev. 1980, 32, 1-46). A large number of in vivo studies have shown that agents that blockade the BK B2 receptor provide therapeutic benefits in pathological conditions such as asthma, allergic rhinitis, pancreatitis, osteoarthritis, traumatic brain injury, Alzheimer's disease, and angioedema.

Numerous peptide and non-peptide antagonists of BK B2 receptor have been described in the prior art. Quinoline derivatives having activity as BK B2 receptor antagonists are, for example, disclosed in WO 2014/159637, WO 2010/031589, WO 2008/116620, WO 2006/40004, WO 03/103671, WO 03/87090, WO 00/23439, WO 00/50418, WO 99/64039, WO 97/41104, WO 97/28153, WO 97/07115, WO 96/13485, EP 0 795 547, EP 0 796 848, EP 0 867 432, and EP 1 213 289. However, these compounds showed a number of deficiencies hampering their utility as a drug, including low metabolic stability, low bioavailability, formation of glutathione adducts and bioactivation (toxicity) as disclosed in WO 2014/159637.

In view of the deficits of the prior art compounds and the severe conditions associated with a pathophysiological level of BK, both acute and chronic, there is still a need for new BK B2 receptor antagonists.

SUMMARY AND DESCRIPTION OF THE INVENTION

The present invention was made in view of the prior art and the needs described above, and, therefore, the object of the present invention is to provide new BK B2 receptor antagonists according to general formula (I), preferably BK B2 receptor antagonists having one or more improved properties, e.g. an improved pharmacokinetic and/or physiochemical property, including bioavailability, solubility, metabolic stability, and a LADME (liberation, absorption, distribution, metabolism, and excretion) property. Other objects of the present invention are to provide a pharmaceutical composition comprising at least one BK B2 receptor antagonist as described herein; a combination preparation containing at least one compound of the invention and at least one further active pharmaceutical ingredient; and uses of the compound(s) of the invention, including the use as a medicament.

These objects are solved by the subject matter of the attached claims as will become apparent upon reference to the following description and definitions.

The present invention relates to:
[1] a compound of the general formula (I):

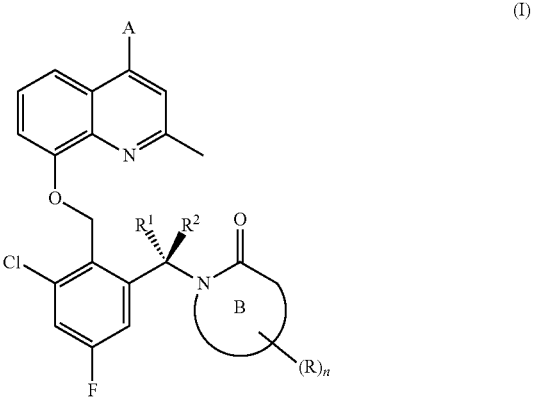

(I)

or a salt thereof, wherein
A represents a group:

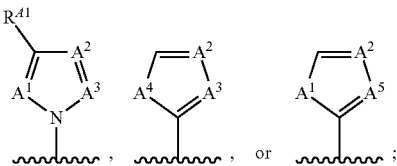

$A^1$ is N, or CH;
$A^2$ is N, or C—$R^{42}$;
$A^3$ is N, or C—$R^{43}$;
$A^4$ is NH, O, or S;
$A^5$ is N—$R^{45}$;
$R^{41}$ represents a hydrogen atom or a methyl group;
$R^{42}$ and $R^{43}$ each, independently of one another, represents a hydrogen atom, halogen atom, OH, CN, $NH_2$; $(C_1$-$C_3)$alkyl, which may be substituted by one or more, identical or different, group(s) selected from a halogen atom, OH, =O, and $NH_2$; $(C_1$-$C_3)$alkoxy, which may be substituted by one or more, identical or different, group(s) selected from a halogen atom, OH, =O, and $NH_2$; ($C_2$-$C_5$)alkoxyalkyl, which may be substituted by one or more, identical or different, group(s) selected from a halogen atom, OH, =O, and $NH_2$; C(O) $NR^{A6}R^{A7}$; or $NR^{A6}R^{A7}$;

$R^{A5}$, $R^{A6}$ and $R^{A7}$ each, independently of one another, represents a hydrogen atom or a ($C_1$-$C_3$) alkyl group, which may be substituted by one or more, identical or different, group(s) selected from a halogen atom, OH, =O, and $NH_2$;

$R^1$ represents a ($C_1$-$C_3$)alkyl or ($C_2$-$C_5$)alkoxyalkyl group, which alkyl group or alkoxyalkyl group may be substituted by one or more, identical or different, group(s) selected from a deuterium atom, halogen atom, OH, =O, and $NH_2$;

$R^2$ represents a hydrogen atom or a deuterium atom;

B represents a 5- or 6-membered nitrogen-containing heterocycloalkyl group having at least one oxo substituent and n substituents R, wherein n denotes the number 0, 1, 2, 3, 4 or 5; and each R, at each occasion independently, represents a halogen atom, OH, $NR^{C1}R^{C2}$, =O, G, OG, or a ($C_3$-$C_5$)cycloalkyl group;

$R^{C1}$ and $R^{C2}$ each, independently of one another, represents a hydrogen atom or a ($C_1$-$C_3$)alkyl group;

G represents a ($C_1$-$C_6$)alkyl group, in which 1 to 5 H atoms may, at each occasion independently, be replaced by a halogen atom, =O, $OR^{G1}$, or $NR^{G2}R^{G3}$, and/or in which one $CH_2$ group, or two non-adjacent $CH_2$ groups, may be replaced by O, C(O), OC(O), C(O)O, C(O)NH, NHC(O), NH, S, SO, and/or $SO_2$; and $R^{G1}$, $R^{G2}$, and $R^{G3}$ each, independently of one another, represents a hydrogen atom, ($C_1$-$C_3$)alkyl, ($C_1$-$C_3$) haloalkyl, ($C_1$-$C_3$) hydroxyalkyl, ($C_1$-$C_3$) heteroalkyl, or ($C_3$-$C_5$) cycloalkyl group.

Compounds are usually described herein using standard nomenclature or the definitions presented below. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. It will be apparent that the compound of the invention may, but need not, be present as a hydrate, solvate or non-covalent complex. In addition, the various crystal forms and polymorphs are within the scope of the present invention, as are prodrugs of the compound of the invention. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The compound according to the invention is described herein using a general formula that includes variables such as, e.g. A, $A^1$-$A^5$, B, $B^1$-$B^7$, R, $R^1$-$R^2$, $R^{A1}$-$R^{A7}$, $R^{B1}$-$R^{B7}$, $R^{B11}$-$R^{B19}$, $R^{C1}$-$R^{C2}$, and $R^{G1}$-$R^{G3}$. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted, or substituted with 1 or 2 group(s) R*, wherein R* at each occurrence is selected independently from the corresponding definition of R*. Also, combinations of substituents and/or variables are permissible only if such combinations result in stable compounds, i.e., compounds that can be isolated, characterized and tested for biological activity.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range. For example, the term "$C_1$-$C_3$" refers to 1 to 3, i.e. 1, 2 or 3, carbon atoms; and the term "$C_1$-$C_6$" refers to 1 to 6, i.e. 1, 2, 3, 4, 5 or 6, carbon atoms. Further, the prefix "($C_{x-y}$)" as used herein means that the chain, ring or combination of chain and ring structure as a whole, indicated in direct association of the prefix, may consist of a minimum of x and a maximum of y carbon atoms (i.e. x<y), wherein x and y represent integers defining the limits of the length of the chain (number of carbon atoms) and/or the size of the ring (number of carbon ring atoms).

A "pharmacologically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such pharmaceutical salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxy ethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmacologically acceptable salts for the compounds provided herein. In general, a pharmacologically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "substituent," as used herein, refers to a molecular moiety that is covalently bonded to an atom within a molecule of interest. For example, a substituent on a ring may be a moiety such as a halogen atom, an alkyl, haloalkyl, hydroxy, cyano, or amino group, or any other substituent described herein that is covalently bonded to an atom, preferably a carbon or nitrogen atom, that is a ring member.

The term "substituted," as used herein, means that any one or more hydrogen atom(s) on the designated atom or group (e.g. alkyl, alkoxy, alkoxyalkyl, cycloalkyl, heterocycloalkyl, heteroaryl) is replaced with a selection from the indicated substituents, provided that the designated atom's normal valence or the group's number of possible sites for substitution is not exceeded, and that the substitution results in a stable compound, i.e. a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and may lead to a loss of aromaticity. For example, a pyridyl group substituted by oxo is a pyridone. The indication mono-, di-, tri or tetrasubstituted denotes groups having one (mono), two (di), three (tri) or four (tetra) substituents, provided that the substitution does not exceeded the number of possible sites for substitution and results in a stable compound. For example, a monosubstituted imidazolyl group may be an (imidazolidin-2-on)yl group and a disubstituted isoxazolyl group may be a ((3,5-dimethyl)isoxazolyl) group.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

The expression alkyl or alkyl group denotes a saturated, straight-chain or branched hydrocarbon group that contains from 1 to 20 carbon atoms, preferably from 1 to 12 carbon atoms, more preferably from 1 to 6 carbon atoms, or the number of carbon atoms indicated in the prefix. If an alkyl is substituted, the substitution may take place, independently of one another, by mono-, di-, or tri-substitution of individual carbon atoms of the molecule, e.g. 1, 2, 3, 4, 5, 6, or 7 hydrogen atom(s) may, at each occasion independently, be replaced by a selection from the indicated substituents. The foregoing also applies if the alkyl group forms a part of a group, e.g. haloalkyl, hydroxyalkyl, alkylamino, alkoxy, or alkoxyalkyl. Examples of an alkyl group include methyl, ethyl, propyl, iso-propyl, n-butyl, iso-butyl, sec-butyl, tert-butyl, n-pentyl, iso-pentyl, n-hexyl, 2,2-dimethylbutyl, or n-octyl, and examples of a substituted alkyl group or a group where the alkyl forms a part of a group, include haloalkyl, e.g. a trifluoromethyl or a difluoromethyl group; hydroxyalkyl, e.g. hydroxymethyl or 2-hydroxyethyl group, and a methoxymethyl group. The term "$(C_{1-6})$ alkyl" includes, for example, H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)—, H$_3$C—CH$_2$—CH(CH$_2$CH$_3$)—, —CH$_2$CH$_2$CH$_2$CH$_2$CH$_2$CH$_3$, —CH(CH$_3$)CH$_2$CH$_2$CH$_2$CH$_3$, (H$_3$CH$_2$C)CH(CH$_2$CH$_2$CH$_3$)—, —C(CH$_3$)$_2$(CH$_2$CH$_2$CH$_3$), —CH(CH$_3$)CH(CH$_3$)CH$_2$CH$_3$, and —CH(CH$_3$)CH$_2$CH(CH$_3$)$_2$.

The expression alkoxy or alkoxy group refers to an alkyl group singular bonded to oxygen, i.e. —O-alkyl. The term "$(C_1-C_6)$ alkoxy" includes, for example, methoxy, ethoxy, n-propoxy, iso-propoxy, n-butoxy, sec-butoxy, iso-butoxy, tert-butoxy, n-pentyloxy, tert-amyloxy- or n hexyloxy, and accordingly $(C_1-C_3)$alkoxy includes methoxy, ethoxy, n-propoxy, iso-propoxy.

The expression alkoxyalkyl or alkoxyalkyl group refers to an alkyl group singular bonded to one or more alkoxy group(s), e.g. -alkyl-O-alkyl or -alkyl-O-alkyl-O-alkyl. The term "$(C_2-C_5)$ alkoxyalkyl" includes, for example, methoxymethyl, methoxyethyl, methoxy-n-propyl, methoxy-iso-propyl, methoxy-n-butyl, methoxy-sec-butyl, methoxy-iso-butyl, methoxy-tert-butyl, methoxyethoxymethyl, methoxyethoxyethyl, ethoxymethoxymethyl, ethoxymethoxyethyl, and 1-ethoxyethyl.

The expression haloalkyl or haloalkyl group refers to an alkyl group in which one, two, three or more hydrogen atoms have been replaced independently of each other by a halogen atom. The term "$(C_1-C_3)$ haloalkyl" includes, for example, fluoromethyl, difluoromethyl, trifluoromethyl, chloromethyl, dichloromethyl, bromomethyl, dibromomethyl, iodomethyl, (1- or 2-)haloethyl (e.g. (1- or 2-)fluoroethyl or (1- or 2-)chloroethyl), (2- or 3-) halopropyl (e.g. (2- or 3-) fluoropropyl or (2- or 3-) chloropropyl).

The expression hydroxyalkyl or hydroxyalkyl group refers to an alkyl group in which one, two, three or more hydrogen atoms have been replaced independently of each other by a hydroxy (OH) group. The term "$(C_1-C_4)$ hydroxyalkyl" includes, for example, hydroxymethyl, hydroxyethyl, hydroxypropyl and hydroxybutyl.

As used herein, the expression heteroalkyl or heteroalkyl group refers to an alkyl group, straight chain or branched as defined above, in which one or more, preferably 1, 2, 3 or 4, carbon atom(s) has/have been replaced, each independently of one another, by an oxygen, nitrogen, selenium, silicon or sulphur atom, preferably by an oxygen, sulphur or nitrogen atom, C(O), OC(O), C(O)O, C(O)NH, NHC(O), NH, SO, SO$_2$ or by a CH=CH group, wherein said heteroalkyl group may be substituted. For example, a "$(C_1-C_4)$heteroalkyl group" contains from 1 to 4, e.g. 1, 2, 3 or 4, carbon atoms and 1, 2, 3 or 4, preferably 1, 2 or 3, heteroatoms selected from oxygen, nitrogen and sulphur (especially oxygen and nitrogen). Examples of a heteroalkyl group include alkylamino, dialkylamino, alkylaminoalkyl, dialkylaminoalkyl, acyl, acylalkyl, alkoxycarbonyl, acyloxy, acyloxyalkyl, carboxyalkylamide, alkoxycarbonyloxy, alkylcarbamoyl, alkylamido, alkylcarbamoylalkyl, alkylamidoalkyl, alkylcarbamoyloxyalkyl, alkylureidoalkyl, alkoxy, alkoxyalkyl, or alkylthio group. The expression alkylthio or alkylthio group refers to an alkyl group, in which one or more non-adjacent CH$_2$ group(s) are replaced by sulphur, wherein the alkyl moiety of the alkylthio group may be substituted. Specific examples of a heteroalkyl group include acyl, methoxy, trifluoromethoxy, ethoxy, n-propyloxy, iso-propyloxy, tert-butyloxy, methoxymethyl, ethoxymethyl, methoxyethyl, methylamino, ethylamino, dimethylamino, diethylamino, iso-propylethylamino, methylaminomethyl, ethylaminomethyl, diisopropylaminoethyl, dimethylaminomethyl, dimethylaminoethyl, acetyl, propionyl, butyryloxy, acetyloxy, methoxycarbonyl, ethoxycarbonyl, isobutyrylaminomethyl, N-ethyl-N methylcarbamoyl, N-methylcarbamoyl, cyano, nitrile, isonitrile, thiocyanate, isocyanate, isothiocyanate and alkylnitrile.

The expression cycloalkyl or cycloalkyl group refers to a saturated carbocyclic ring group comprising one or more rings (preferably 1 or 2) and containing from 3 to 14 ring carbon atoms, preferably from 3 to 10 (more preferably 3, 4, 5, 6 or 7) ring carbon atoms; the cycloalkyl group may be substituted and can be bonded as a substituent via every suitable position of the ring system. Examples of cycloalkyl include monocyclic hydrocarbon rings, bicyclic hydrocarbon rings and spiro-hydrocarbon rings. In a bicyclic cycloalkyl group, two rings are joined together so that they have at least two carbon atoms in common. In a spiro-hydrocarbon ring, 2 or 3 rings are linked together by one common carbon atom (spiro-atom). If a cycloalkyl is substituted, the substitution may take place, independently of one another, by mono- or di-substitution of individual ring carbon atoms of the molecule, and the cycloalkyl group as a whole may carry 1, 2, 3, or 4 substituents from the indicated selection of substituents, i.e. 1, 2, 3, or 4 hydrogen atom(s) of the carbon ring atoms may, at each occasion independently, be replaced by a substituent selected from the indicated list of substituents thereby resulting in a mono-, di-, tri-, or tetrasubstituted cycloalkyl group. Examples of cycloalkyl include cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, and spiro[3.3]heptyl. If a cycloalkyl is partially unsaturated, the group contains one, two or more double bonds, such as, for example, a cycloalkenyl group, including cyclopropenyl, cyclobutenyl, cyclopentenyl, cyclohexenyl, cycloheptenyl, cyclobutadienyl, cyclopentadienyl, cyclohexadienyl, bicyclo[2.2.1]heptadienyl, and spiro[4,5]decenyl.

The expression heterocycloalkyl or heterocycloalkyl group refers to a cycloalkyl group, saturated or partially unsaturated, as defined above, in which one or more, preferably 1, 2 or 3, ring carbon atom(s) has/have been replaced each independently of one another by an oxygen, nitrogen or sulphur atom, preferably oxygen or nitrogen, or by NO, SO or SO$_2$; the heterocycloalkyl may be substituted and can be bonded as a substituent via every suitable position of the ring system; at least one carbon atom must be present between two oxygen atoms and between two sulphur atoms or between an oxygen and a sulphur atom; and the ring as a whole must have chemical stability. A heterocycloalkyl group has preferably 1 or 2 ring(s) containing from 3 to 10 (more preferably 3, 4, 5, 6 or 7, and most preferably 5, 6 or 7) ring atoms. Examples of heterocycloalkyl include aziridinyl, oxiranyl, thiiranyl, oxaziridinyl, azetidinyl, dioxiranyl, oxetanyl, thietanyl, diazetidinyl, dioxetanyl, dithietanyl, pyrrolidinyl, tetrahydrofuranyl, thiolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiomorpholinyl, trioxanyl, azepanyl, oxepanyl, thiepanyl, homopiperazinyl, urotropinyl, oxazolidinonyl, dihydropyrazolyl, dihydropyrrolyl, dihydropyrazinyl, dihydropyridyl, dihydropyrimidinyl, dihydrofuryl, dihydropyranyl, and examples of substituted heterocycloalkyl include lactam, lactone, and cyclic carbamate, cyclic carbamide as well as cyclic imide ring systems.

The expression halogen or halogen atom as used herein means fluorine, chlorine, bromine, or iodine.

The expression heteroatom as used herein, preferably denotes an oxygen, nitrogen or sulphur atom, more preferably a nitrogen or oxygen atom.

The present invention preferably relates to one or more of the following:

[2] the compound or salt according to [1] above, wherein A represents:

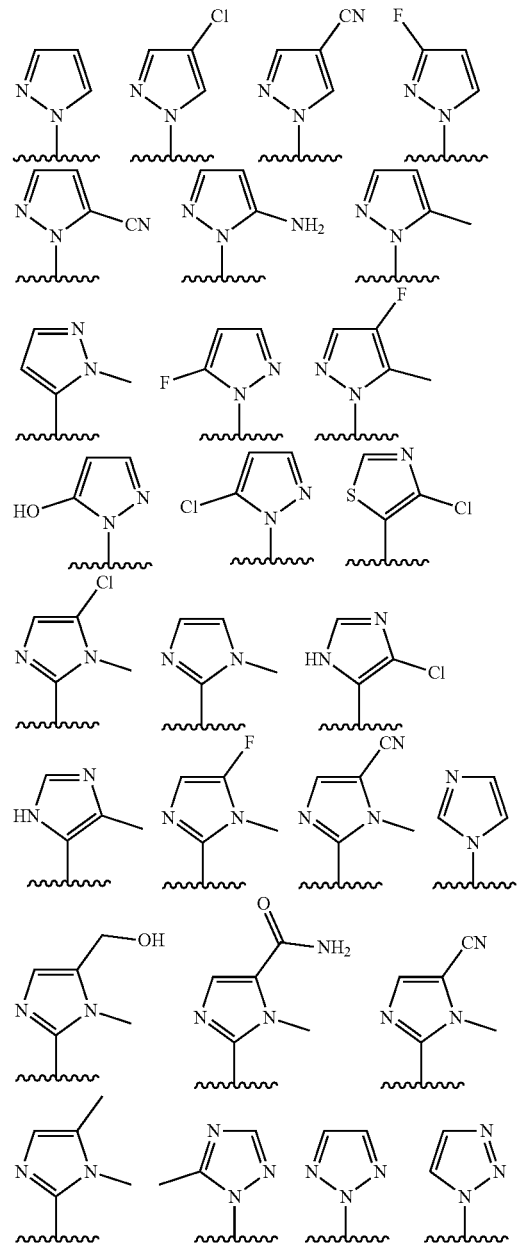

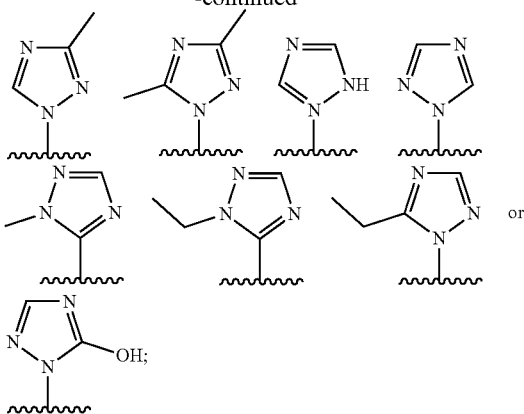

[3] the compound or salt according to [1] or [2], wherein A represents:

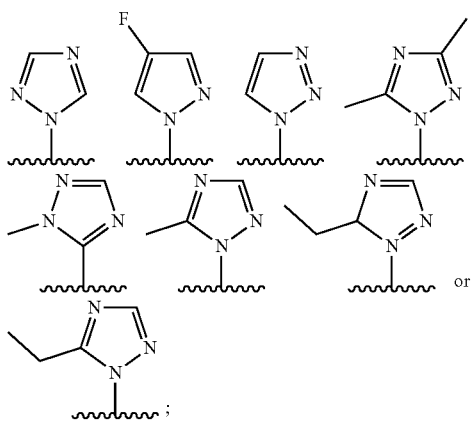

[4] the compound or salt according to any one of [1] to [3], wherein A represents:

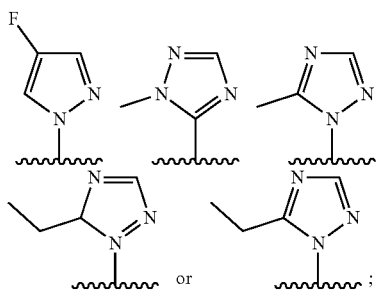

[5] the compound or salt according to any one of [1] to [4], wherein $R^1$ represents a $(C_1-C_2)$alkyl or $(C_2-C_4)$ alkoxyalkyl group, which alkyl group or alkoxyalkyl group may be substituted by one or more, identical or different, group(s) selected from a halogen atom and OH;

[6] the compound or salt according to any one of [1] to [5], wherein $R^1$ represents a methyl, ethyl, methoxymethyl, methoxyethyl, or ethoxymethyl group, which may be substituted by one or more, identical or different, group(s) selected from a halogen atom and OH;

[7] the compound or salt according to any one of [1] to [6], wherein $R^1$ represents $CH_3$, $C_2H_5$, $CH_2OH$, $CH_2F$, $CHF_2$, $CF_3$, $CH_2CH_2OH$, $CH_2CH_2F$, $CH_2CF_3$, $CH_2OCH_3$, $CH_2OCHF_2$, or $CH_2OCF_3$;

[8] the compound or salt according to any one of [1] to [7], wherein $R^1$ represents $CH_3$, $C_2H_5$, or $CH_2OH$;

[9] the compound or salt according to any one of [1] to [8], wherein n denotes the number 0, 1, 2, 3, or 4; and preferably the number 0, 1, 2, or 3;

[10] the compound or salt according to any one of [1] to [9], wherein $R^2$ represents a hydrogen atom;

[11] the compound or salt according to any one of [1] to [9], wherein $R^2$ represents a deuterium atom;

[12] the compound or salt according to any one of [1] to [11], wherein the oxo-substituted, nitrogen-containing heterocycloalkyl group B represents the 5-membered group (HetB1):

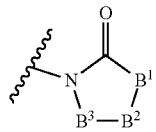

(HetB1)

wherein
$B^1$ is N—$R^{B1}$, O or $CR^{B2}R^{B3}$;
$B^2$ is $CR^{B4}R^{B5}$; and
$B^3$ is $CR^{B6}R^{B7}$;
$R^{B1}$ represents a hydrogen atom, G, or a $(C_3-C_5)$ cycloalkyl group;
$R^{B2}$ and $R^{B3}$ each, independently of one another, represents a hydrogen atom, a halogen atom, OH, G, OG, or $NR^{C1}R^{C2}$;
$R^{B4}$ and $R^{B5}$ each, independently of one another, represents a hydrogen atom, a halogen atom, OH, G, or OG; or $R^{B4}$ and $R^{B5}$ are taken together to form =O;
$R^{B6}$ and $R^{B7}$ each, independently of one another, represents a hydrogen atom, a halogen atom, or G; and
G, $R^{C1}$ and $R^{C2}$ are defined as in [1];

[13] the compound or salt according to [12], wherein at maximum 1, 2, or 3 of the ring substituents selected from $R^{B1}$ to $R^{B7}$ is/are different from a hydrogen atom;

[14] the compound or salt according to [12] or [13], wherein $B^1$ to $B^3$ are as defined in any one of the following (i) to (iii):
(i) $B^1$ is N—$R^{B1}$; $B^2$ is C=O or $CH_2$; and $B^3$ is $CH_2$ or $CH(CH_3)$;
(ii) $B^1$ is O; $B^2$ is $CR^{B4}R^{B5}$; and $B^3$ is $CH_2$ or $CH(CH_3)$; or
(iii) $B^1$ is $CR^{B2}R^{B3}$; $B^2$ is $CR^{B4}R^{B5}$; and $B^3$ is $CH_2$; and $R^{B1}$, $R^{B2}$, $R^{B3}$, $R^{B4}$ and $R^{B5}$ are as defined in [12];

[15] the compound or salt according to any one of [12] to [14], wherein each of $R^{B2}$, $R^{B3}$, $R^{B4}$, $R^{B5}$, $R^{B6}$ and $R^{B7}$, and independently of one another, represents a hydrogen atom, a halogen atom, OH, $(C_1-C_3)$alkyl, $(C_1-C_3)$ haloalkyl, $(C_1-C_3)$ hydroxyalkyl, $O(C_1-C_3)$alkyl, or $O(C_1-C_3)$ haloalkyl;

[16] the compound or salt according to any one of [12] to [15], wherein $R^{B1}$ represents a hydrogen atom, $(C_1-C_3)$ alkyl, $(C_1-C_3)$ haloalkyl, $(C_1-C_3)$ hydroxyalkyl, $(C_3-C_5)$cycloalkyl, $((C_1-C_3)$alkyl$)$-$NR^{C1}R^{C2}$, or $((C_1-C_3)$ alkyl$)$-C(O)—$NR^{C1}R^{C2}$, and each of $R^{C1}$ and $R^{C2}$ is defined as in [1];

[17] the compound or salt according to any one of [12] to [16], wherein the 5-membered group (HetB1) is selected from:

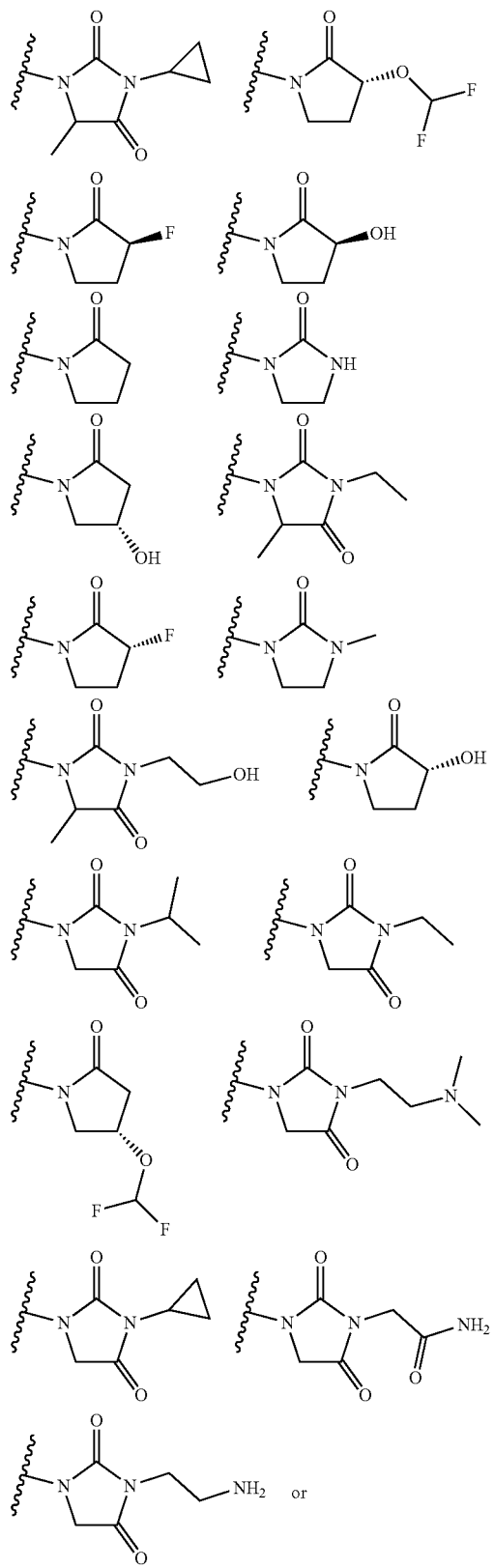

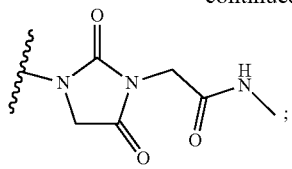

[18] the compound or salt according to any one of [1] to [11], wherein the oxo-substituted, nitrogen-containing heterocycloalkyl group B represents the 6-membered group (HetB2):

(HetB2)

wherein
$B^4$ is C=O or $CR^{B11}R^{B12}$;
$B^5$ is N—$R^{B13}$, O or $CR^{B14}R^{B15}$;
$B^6$ is C=O or $CR^{B16}R^{B17}$;
$B^7$ is $CR^{B18}R^{B19}$;
$R^{B11}$, $R^{B12}$, $R^{B14}$, $R^{B15}$, $R^{B16}$, $R^{B17}$, $R^{B18}$ and $R^{B19}$ each, independently of one another, represents a hydrogen atom, halogen atom, G, OH, OG, ($C_3$-$C_5$) cycloalkyl, or an O($C_3$-$C_5$)cycloalkyl group;
$R^{B13}$ represents a hydrogen atom, G, or a ($C_3$-$C_5$) cycloalkyl group; and
G is defined as in [1];

[19] the compound or salt according to [18], wherein at maximum 1, 2, 3 or 4; preferably 1, 2 or 3; of the ring substituents selected from $R^{B11}$ to $R^{B19}$ is/are different from a hydrogen atom;

[20] the compound or salt according to [18] or [19], wherein each of $R^{B11}$, $R^{B12}$, $R^{B14}$, $R^{B15}$, $R^{B16}$, $R^{B17}$, $R^{B18}$ and $R^{B19}$, and independently of one another, represents a hydrogen atom, a halogen atom, $G^1$, OH, $OG^1$, ($C_3$-$C_5$)cycloalkyl, or O($C_3$-$C_5$)cycloalkyl;
$G^1$ represents a ($C_1$-$C_4$)alkyl group, in which 1 to 3 H atoms may, at each occasion independently, be replaced by a halogen atom, =O, $OR^{G1}$, or $NR^{G2}R^{G3}$, and/or in which one $CH_2$ group, or two non-adjacent $CH_2$ groups, may be replaced by O, C(O), OC(O), C(O)O, C(O)NH, NHC(O), NH, S, SO, and/or $SO_2$; and
each of $R^{G1}$, $R^{G2}$, and $R^{G3}$ is defined as in [1];

[21] the compound or salt according to any one of [18] to [20], wherein each of $R^{B11}$, $R^{B12}$, $R^{B14}$, $R^{B15}$, $R^{B16}$, $R^{B17}$, $R^{B18}$ and $R^{B19}$, and independently of one another, represents a hydrogen atom, a halogen atom, OH, ($C_1$-$C_3$)alkyl, ($C_1$-$C_3$) haloalkyl, ($C_1$-$C_3$) hydroxyalkyl, O($C_1$-$C_3$)alkyl, or O($C_1$-$C_3$) haloalkyl;

[22] the compound or salt according to any one of [18] to [21], wherein $R^{B13}$ represents a hydrogen atom, ($C_1$-$C_3$)alkyl, ($C_1$-$C_3$) haloalkyl, ($C_1$-$C_3$) hydroxyalkyl, or a ($C_3$-$C_5$)cycloalkyl group; preferably a hydrogen atom, ($C_1$-$C_3$)alkyl, or ($C_1$-$C_3$) haloalkyl; and more preferably a hydrogen atom or ($C_1$-$C_3$)alkyl;

[23] the compound or salt according to any one of [18] to [22], wherein $B^4$ to $B^6$ are as defined in any one of the following (i) to (v):

(i) $B^4$ is C=O; $B^5$ is N—$R^{B13}$; and $B^6$ is $CR^{B16}R^{B17}$;
(ii) $B^4$ is $CR^{B11}R^{B12}$; $B^5$ is N—$R^{B13}$; and $B^6$ is C=O;
(iii) $B^4$ is $CR^{B11}R^{B12}$; $B^5$ is O; and $B^6$ is $CR^{B16}R^{B17}$;
(iv) $B^4$ is $CR^{B11}R^{B12}$, $B^5$ is N—$R^{B13}$; and $B^6$ is $CR^{B16}R^{B17}$; or
(v) $B^4$ is $CR^{B11}R^{B12}$, $B^5$ is $CR^{B14}R^{B15}$; and $B^6$ is $CR^{B16}R^{B17}$;

$B^7$ represents $CH_2$ or $CH(CH_3)$;

$R^{B11}$, $R^{B12}$, $R^{B14}$, $R^{B15}$, $R^{B16}$, $R^{B17}$, $R^{B18}$ and $R^{B19}$ are defined as in any one of [18], [20] or [21]; and $R^{B13}$ is defined as in [18] or [22];

[24] the compound or salt according to any one of [18] to [23], wherein the 6-membered group (HetB2) is selected from:

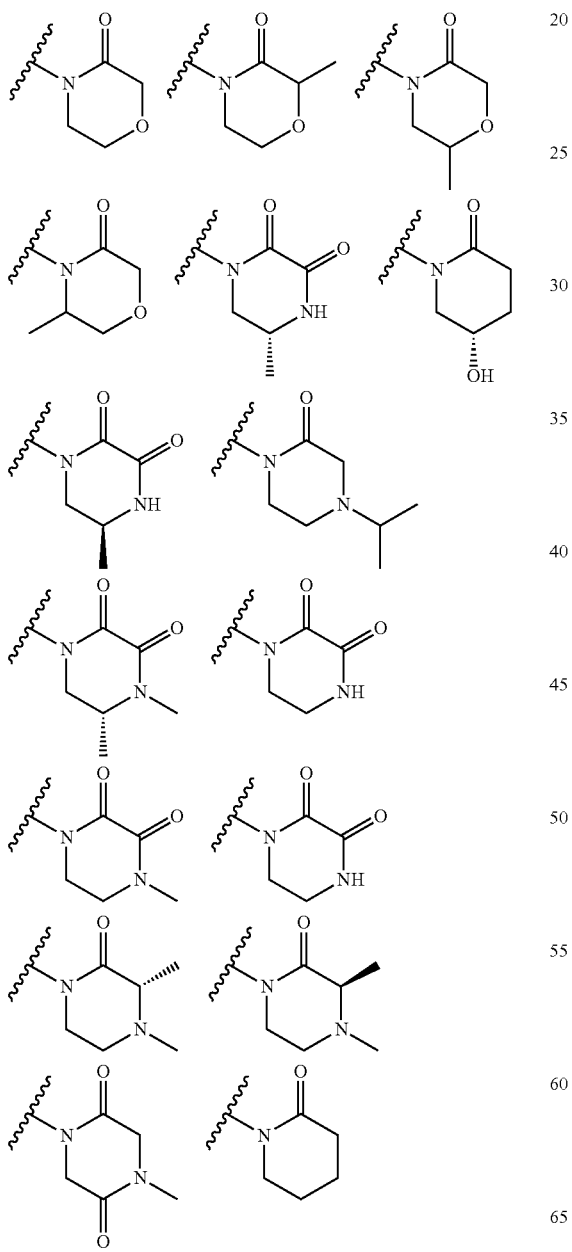

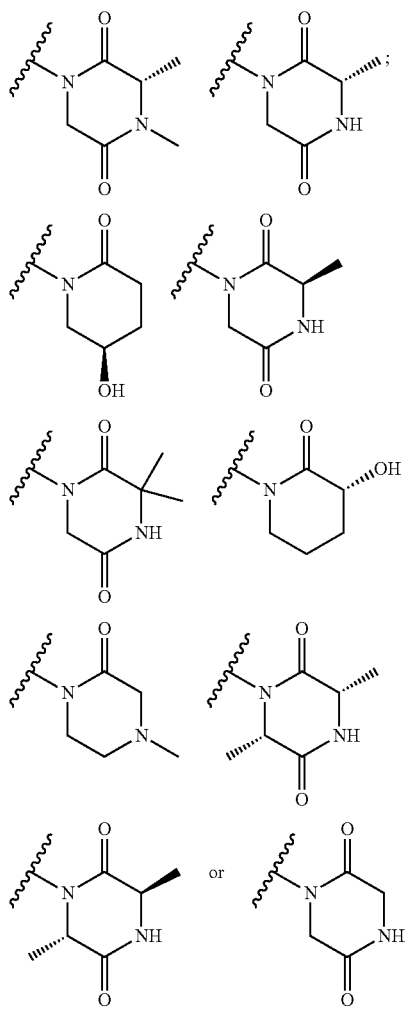

[25] the compound or salt according to any one of [1] to [24], wherein the compound is selected from the group:

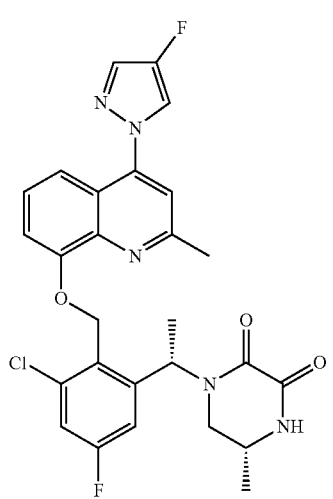

15
-continued
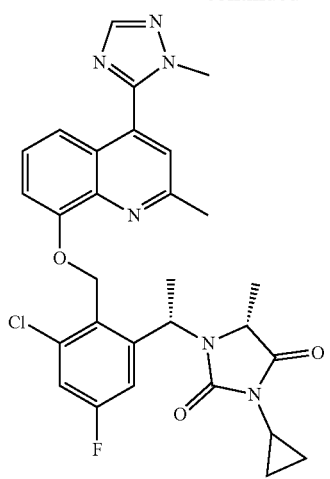
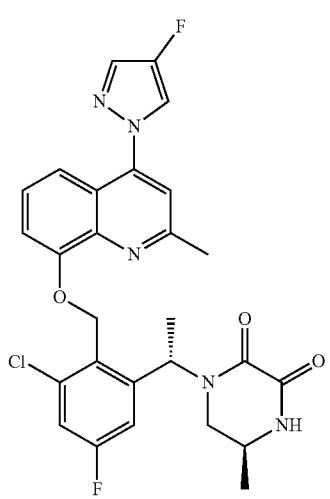
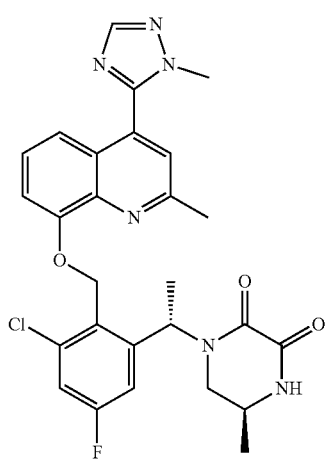
16
-continued
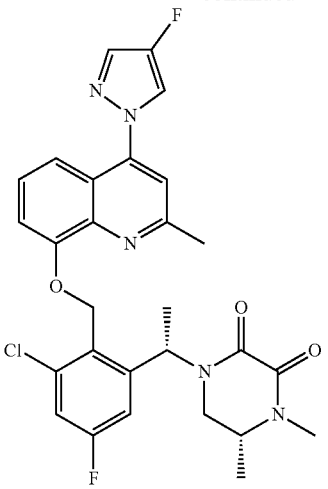
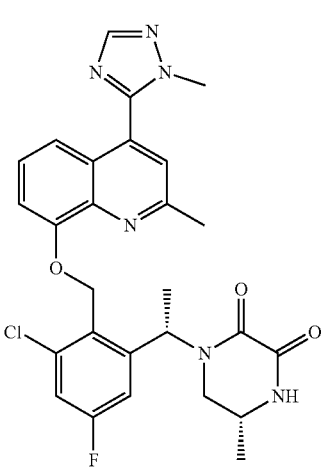
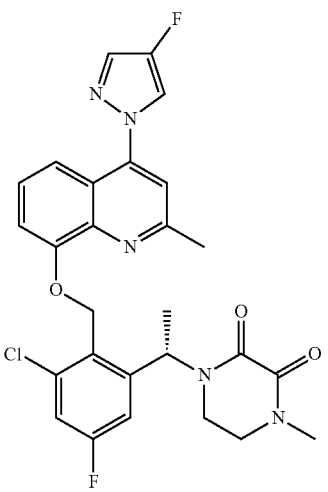

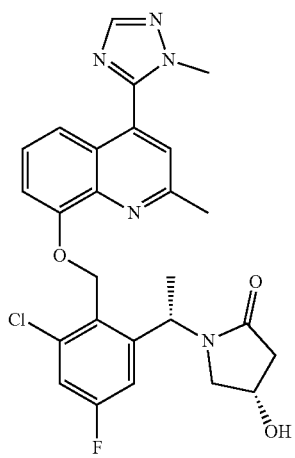
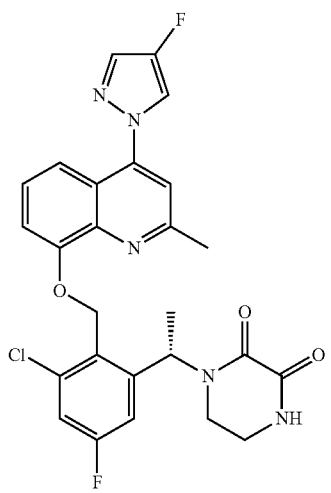
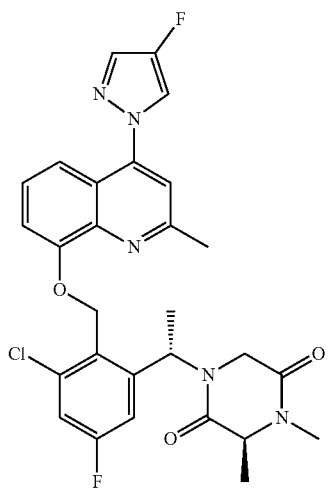
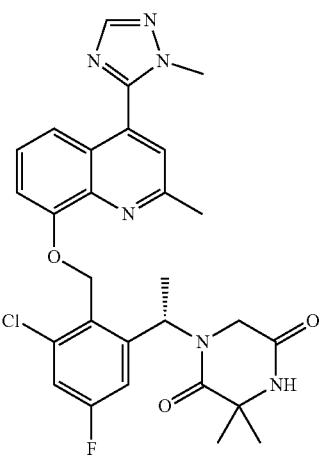
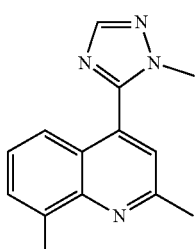
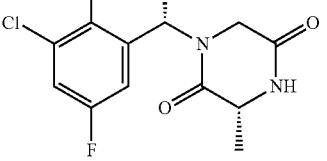
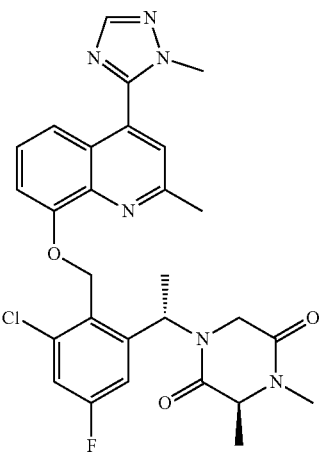

19
-continued
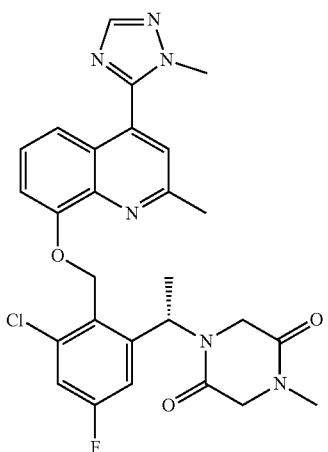
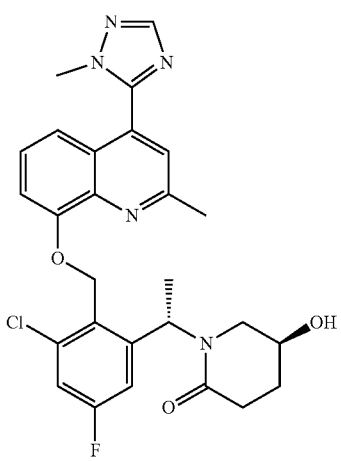
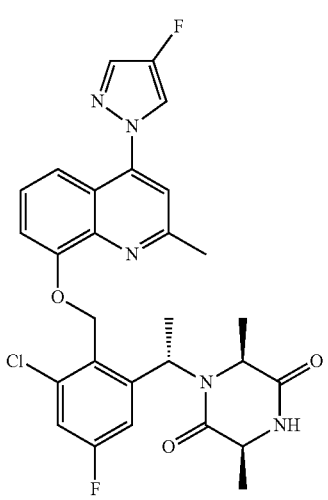
20
-continued
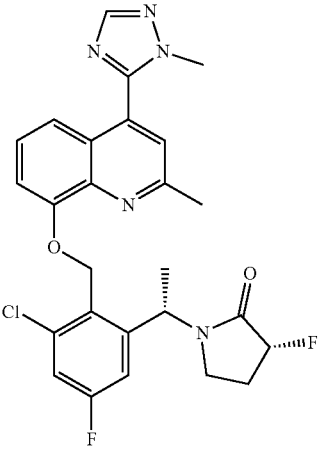
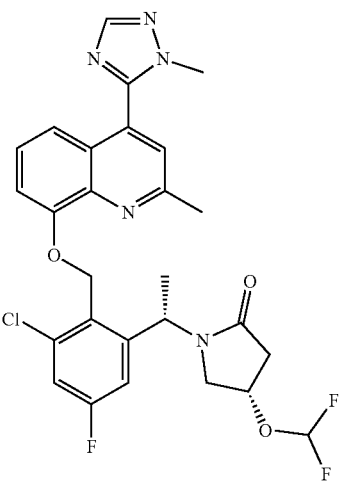
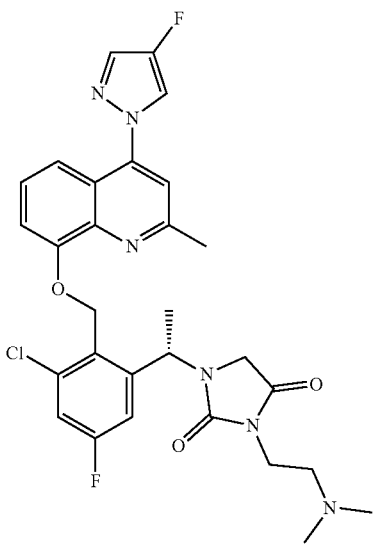

-continued

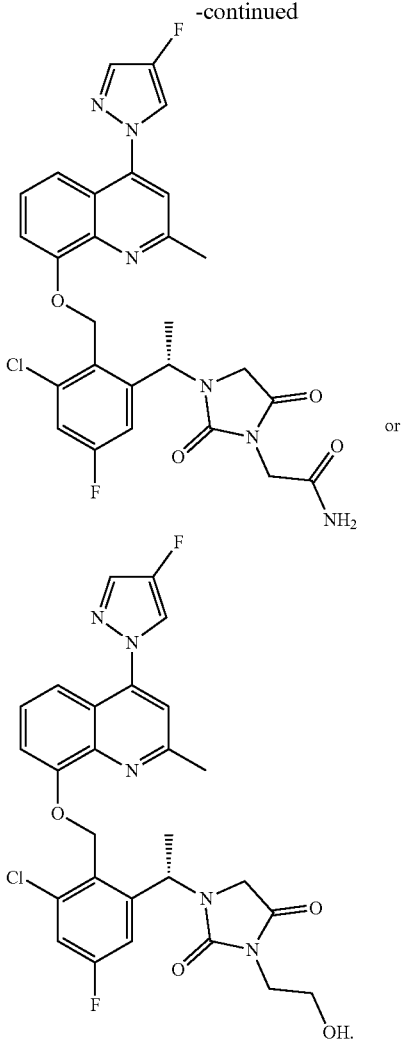

Compounds including suitable combinations of preferred embodiments, i.e. [2] to [25], of the compound according to general formula (I), or a salt thereof, are particularly preferred; e.g. a compound or salt thereof including a combination of [1], [3], [6] and [9] as disclosed herein. In other words, the present invention specifically encompasses all possible combinations of [1] to [24] as indicated above, which result in a stable compound.

The compound according to any one of [1] to [25] provided herein exhibits high activity on human BK B2 receptor, e. g. an inhibition constant $IC_{50}$ (half-maximal inhibitory concentration) for inhibition of BK-induced BK B2 receptor activity of 1 micromolar (μM) or less, e.g. of from 251 nanomolar (nM) to 1 μM; preferably an $IC_{50}$ of 250 nM or less, e.g. of from 51 nM to 250 nM; still more preferably an $IC_{50}$ of 50 nM or less; even more preferably an $IC_{50}$ of about 10 nM or less, or 1 nM or less in the assay mentioned below. The compound according to any one of [1] to [25] can exhibit a high activity on human BK B2 receptor, but also on BK B2 receptors of species other than human, e.g. rat, mouse, gerbil, guinea pig, rabbit, dog, cat, pig, or cynomolgus monkey.

The activity and more specifically the bioactivity of the compounds according to the present invention can be assessed using appropriate assays known to those skilled in the art, e.g. in vitro or in vivo assays. For instance, the inhibitory effect (expressed as $IC_{50}$ value) of a compound of the invention on the B2 receptor activity may be determined via intracellular calcium mobilization assay, such as the assay provided in Example 14, which is thus an embodiment of a standard in vitro B2 receptor-mediated assay. A particularly preferred compound or salt according to any one of [1] to [25] exhibits an $IC_{50}$ of 50 nM or less in a standard in vitro BK B2 receptor assay; e.g. the assay provided in Example 14.

The therapeutic use of a compound of general formula (I), its pharmacologically acceptable salt, solvate or hydrate; and also of a formulation or a pharmaceutical composition containing the same are within the scope of the present invention. The present invention also relates to the use of a compound of general formula (I) as active ingredient in the preparation or manufacture of a medicament.

A pharmaceutical composition according to the present invention comprises at least one compound of formula (I) or a pharmacologically acceptable salt thereof, preferably a compound according to any one of [1] to [25] or a salt thereof, and, optionally, at least one, i.e. one or more, carrier substance, excipient and/or adjuvant. In particular, a pharmaceutical composition of the invention can comprise one or more compound(s) according to the invention, e.g. a compound according to any one of [1] to [25], and, optionally, at least one carrier substance, excipient and/or adjuvant.

The pharmaceutical composition may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Furthermore, one or more other active ingredient(s) may (but need not) be included in the pharmaceutical composition provided herein. For instance, one or more compound(s) of the invention may advantageously be contained in a combination preparation that contains at least one further active pharmaceutical ingredient. The further or supplemental active agent or active pharmaceutical ingredient is preferably an active agent or active pharmaceutical ingredient which has utility in the prevention or treatment of one or more condition(s) responsive to BK B2 receptor modulation, including a condition selected from the group comprising a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; and edema. For instance, at least one compound or pharmaceutically acceptable salt of the invention may advantageously be contained in a combination preparation that includes an antibiotic, anti-fungal, or anti-viral agent, an anti histamine, a non-steroidal anti-inflammatory drug, a disease modifying anti-rheumatic drug, a cytostatic drug, a drug with smooth muscle activity modulatory activity, an antibody, or mixtures of the aforementioned as further or supplemental active agent or active pharmaceutical ingredient.

The pharmaceutical composition, or the combination preparation, of the invention may be formulated for any appropriate manner of administration, including, for example, topical (e.g., transdermal or ocular), oral, buccal, nasal, vaginal, rectal or parenteral administration. The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch). Briefly summarized, the pharmaceutical composition as well as the combination preparation can, for example, be formulated as an aerosol, a cream, a gel, a pill, a capsule, a syrup, a solution, a transdermal patch or a pharmaceutical delivery device.

For the prevention and/or treatment of diseases mediated by BK or analogues thereof, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

Compounds of general formula (I) provided herein can also be used as antagonists of BK B2 receptors in a variety of applications, both in vitro and in vivo. BK B2 receptor antagonists according to the present invention may be used to inhibit the binding of BK B2 receptor ligands (e.g., BK) to BK B2 receptor in vitro or in vivo. This use includes, for example, a method of inhibiting binding of BK to BK B2 receptor in vitro or in vivo, wherein said method comprises contacting BK B2 receptor with at least one compound or salt according to the invention, e.g. according to any one of [1] to [25], under conditions and in an amount sufficient to detectably inhibit binding of BK or any other substance to BK B2 receptor. BK B2 receptor antagonists provided herein are preferably administered to a patient (e.g., a human) orally or topically, and are present within at least one body fluid or tissue of the patient while modulating BK B2 receptor activity.

BK B2 receptor antagonists according to any one of [1] to [25], the pharmaceutical composition, or the combination preparation according to the present invention are useful as a medicament. In particular, the BK B2 receptor antagonists, the pharmaceutical composition, or the combination preparation according to the present invention are useful in the treatment and/or prevention and/or prophylaxis of a condition or disease that is responsive to BK B2 receptor modulation. The condition or disease that is responsive to BK B2 receptor modulation may be a skin disorder; eye disease, ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; edema or capillary leak syndrome(s). In the following the above indicated diseases and conditions that are responsive to BK B2 receptor modulation are further specified.

Skin disorders: Within the present application the term "skin disorders" encompasses, but is not limited to, disorders such as skin aging, skin efflorescences including pressure sores, decubital ulcers, irritated, sensitive and dysaesthetic skin, erythema, rash, skin edema, psoriasis, eczema, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis (Scholzen, T. E.; Luger, T. A. Exp Dermatol. 2004; 13 Suppl 4:22-6) neurodermatitis, radiation damage, sunburn, pruritus, itching, urticaria (EP0622361; Frigas, E.; Park, M. Immunol. Allergy Clin. North Am. 2006, 26, 739-51; Luquin, E.; Kaplan, A. P.; Ferrer, M. Clin. Exp. Allergy 2005, 35, 456-60; Kaplan, A. P.; Greaves, M. W. J. Am. Acad. Dermatol. 2005, 53, 373-88; quiz 389-92), psoriasis, mycosis, tissue ulceration, epidermolysis bullosa, wounds including abnormal wound healing, burns (Nwariaku, F. E.; Sikes, P. J.; Lightfoot, E.; Mileski, W. J.; Baxter, C. Burns 1996, 22, 324-7; Neely, A. N.; Imwalle, A. R.; Holder, I. A. Burns 1996, 22, 520-3), frostbite, skin inflammation and edema caused by venoms, alopecia, hair squama, corn, wart and panaris.

Eye diseases: Within the present application the term "eye diseases" encompasses, but is not limited to, inflammatory disorders such as scleritis, conjunctivitis, chemosis, iritis, iridocyclitis, uveitis, chorioretinitis, as well as disorders such as retinochoroidal circulatory disorders, bacterial eye infections, unspecific conjunctivitis and eye irritations, retinopathy of prematurity, proliferative vitreoretinopathy, macular degeneration (including age related macular degeneration and including both wet and dry forms), corneal diseases including corneal graft rejection, corneal injury, corneal scarring, corneal ulceration, corneal haze, keratoconus, glaucoma (preferably open angle glaucoma), myopia, ocular hypertension, ocular vessel damage, angiogenesis, eye fibrosis (e.g. anterior subcapsular fibrosis, posterior subcapsular opacities, posterior capsular opacities, corneal haze after laser surgery, subconjunctival scarring after glaucoma surgery), proliferative vitreoretinopathy (PVR), bacterial ocular infections including hordeolum and ptilosis.

Ear diseases: Within the present application the term "ear diseases" encompasses, but is not limited to, disorders such as Meniere's disease, inflammation of the middle ear, inflammation of the external auditory canal and acute hearing loss.

Mouth, throat and respiratory diseases: Within the present application the term "mouth, throat and respiratory diseases" encompasses, but is not limited to, disorders such as inflammation of the oral mucosa and gums including aphta and stomatitis, parodontitis, epiglottitis, pharyngitis, laryngotracheitis, tonsillitis, common cold, angina, rhinitis including seasonal allergic rhinitis or perennial allergic rhinitis, rhinorrea, sinusitis of whatever type, etiology or pathogenesis or sinusitis that is a member selected from the group consisting of purulent or nonpurulent sinusitis, acute and chronic sinusitis and ethmoid, frontal, maxillary or sphenoid sinusitis, expectoration, pneumoconiosis of whatever type or genesis, including for example aluminosis, anthracosis, asbestosis, chalicosis, siderosis, silicosis, tabacosis and, in particular, byssinosis, bronchitis, cough, trachitis, congestion, pneumonia, eosinophilc lung infiltrate, chronic eosinophilic pneumonia, idiopathic pulmonary fibrosis and other fibrotic lung diseases, treatment related fibrotic lung disease e.g. related to radiation, methotrexate, chemotherapy, amiodarone or nitrofurantoin, sarcoidosis, acute respiratory distress syndrome (ARDS), bronchoconstriction, asthma of whatever type (Akbary, A. M.; Wirth, K. J.; Scholkens, B. A. *Immunopharmacology* 1996, 33, 238-42; WO 00/75107 A2), etiology, or pathogenesis, or asthma that is a member selected from the group of atopic asthma, non-atopic asthma, allergic and non-allergic asthma, extrinsic asthma caused by environmental factors, intrinsic asthma caused by pathophysiologic disturbances, bronchial asthma, IgE-mediated asthma, essential asthma and essential asthma of unknown or inapparent cause, true asthma, emphysematous asthma, exercise-induced asthma, occupational asthma, infective asthma caused by bacterial, fungal, protozoal or viral infection, incipient asthma, wheezy infant syndrome, bronchial hyperreactivity, chronic obstructive pulmonary disease (COPD), COPD that is characterized by irreversible, progressive airways obstruction, acute respiratory distress syndrome (ARDS) and exacerbation of airways hyperreactivity consequent to other drug therapy, dyspnea, hyperoxic alveolar injury, pulmonary emphysema, pleurisy, tuberculosis, exposure to high altitude i.e. acute mountain sickness and preferably high altitude pulmonary edema (HAPE), resistant cough, bronchial hyporeactivity.

Gastrointestinal diseases: Within the present application the term "gastrointestinal diseases" encompasses, but is not limited to, disorders including esophagitis, gastritis, irritable stomach, gastric and duodenal ulcer, ileus, colon irritable, inflammatory bowel diseases including Crohn's disease and ulcerative colitis, enteritis, hypertensive gastro- and colopathy, colitis, peritonitis, appendicitis, rectitis, gastrointestinal hemorrhage caused by a portal hypertension, collateral circulation or hyperemia, postgastrectomy dumping-syndrome, digestion discomfort, diarrhea, hemorrhoids, worm diseases, abdominal colic and colic of parts of the gastrointestinal system.

Liver, gallbladder and pancreatic diseases (Cugno, M.; Salerno, F.; Nussberger, J.; Bottasso, B.; Lorenzano, E.; Agostoni, A. *Clin. Sci.* (Lond) 2001, 101, 651-7; WO 01/56995 A1; EP0797997 B1; Wirth, K. J.; Bickel, M.; Hropot, M.; Gunzler, V.; Heitsch, H.; Ruppert, D.; Scholkens, B. A. *Eur. J. Pharmacol.* 1997, 337, 45-53): Within the present application the term "liver and gallbladder diseases" encompasses, but is not limited to, disorders such as hepatitis, cirrhosis of the liver, liver fibrosis (e.g. due to viral (HBV/HCV) infections, toxins (alcohol), fatty liver, bile stasis, hypoxia), portal hypertension, hepatorenal syndrome, hepatogenic edema, cholangitis, cholecystitis, acute and chronic pancreatitis, and biliary colic.

Urinary tract and kidney diseases: Within the present application the term "Urinary tract and kidney diseases" encompasses, but is not limited to, urinary tract infections such as acute and chronic cystitis, interstitial cystitis (Campbell, D. *J. Clin. Exp. Pharmacol. Physiol.* 2001, 28, 1060-5; Meini, S.; Patacchini, R.; Giuliani, S.; Lazzeri, M.; Turini, D.; Maggi, C. A.; Lecci, A. *Eur. J. Pharmacol.* 2000, 388, 177-82; Zuraw, B. L.; Sugimoto, S.; Parsons, C. L.; Hugli, T.; Lotz, M.; Koziol, J. J. *Urol.* 1994, 152, 874-8; Rosamilia, A.; Clements, J. A.; Dwyer, P. L.; Kende, M.; Campbell, D. J. *J. Urol.* 1999, 162, 129-34), irritable bladder, overactive bladder (WO 2007003411 A2), incontinence including but not limited to stress-, urge and reflex incontinence, benign prostate hyperplasia (Srinivasan, D.; Kosaka, A. H.; Daniels, D. V.; Ford, A. P.; Bhattacharya, A. *Eur J Pharmacol.* 2004, 504(3):155-67), chronic renal disease, urethritis, inflammatory kidney diseases including glomerulonephritis, glomerular disease of the kidney, interstitial nephritis, pyelonephritis, diuresis, proteinuria, natriuresis, calciuresis, disorders of water balance, disorders of electrolyte balance, disorders of acid-base balance and renal colic, renal fibrosis, chronic renal allograft dysfunction, contrast-induced nephropathy.

Diseases of male genitale organs and female genitale organs: Within the present application the term "diseases of male genitale organs and female genitale organs" encompasses, but is not limited, to altered sperm mobility, male infertility, orchitis, prostatitis, prostate enhancement, mastitis, inflammatory pelvis diseases, vaginal infections and pain, adnexitis, colpitis, soft ulcus, syphilis, clap and ovarian hyperstimulation syndrome (Ujioka, T.; Matsuura, K.; Tanaka, N.; Okamura, H. *Hum Reprod.* 1998 November; 13(11):3009-15).

Diseases of the hormone system: Within the present application the term "diseases of the hormone system" encompasses, but is not limited to, menstrual disorders and pain, climacteric disturbance, emesis, premature uterine contractions, premature labor, endometriosis, endometritis, myoma, pre-eclampsia.

Metabolic diseases: Within the present application the term "metabolic diseases" encompasses, but is not limited to, disorders such as diabetes, including non-insulin dependent diabetes mellitus, diabetic retinopathy, diabetic macular edema (Speicher, M. A.; Danis, R. P.; Criswell, M.; Pratt, L. *Expert Opin. Emerg. Drugs* 2003, 8, 239-50; Gao, B. B.; Clermont, A.; Rook, S.; Fonda, S. J.; Srinivasan, V. J.; Wojtkowski, M.; Fujimoto, J. G.; Avery, R. L.; Arrigg, P. G.; Bursell, S. E.; Aiello, L. P.; Feener, E. P. *Nat. Med.* 2007, 13, 181-8; Tranos, P. G.; Wickremasinghe, S. S.; Stangos, N. T.; Topouzis, F.; Tsinopoulos, I.; Pavesio, C. E. *Surv. Ophthalmol* 2004, 49, 470-90), diabetic nephropathy and diabetic neuropathy, insulin resistance and diabetic ulceration, diseases of the proteo- and purine metabolism such as gout and disorder of lipometabolism, hypoglycemia.

Cardiovascular diseases: Within the present application the term "cardiovascular diseases" encompasses, but is not limited to, disorders including vascular permeability, vasodilation, peripheral circulatory disorders, arterial circulatory disorders including aortic aneurysm, abdominal aortic aneurysm, brain aortic aneurysm, hypertension and hypotension associated with sepsis, restenosis after percutaneous transluminal coronary angioplasty, atherosclerosis including atherosclerotic plaque rupture (Fernando, A. N.; Fernando, L. P.; Fukuda, Y.; Kaplan, A. P. *Am J Physiol Heart Circ Physiol.* 2005 July; 289(1):H251-7) hemangioma, angiofibroma, venous disorders such as thrombosis, varicosity, phlebitis, thrombophlebitis, phlebothrombosis, cardiopathy, congestive heart failure, coronary heart disease, carcinoid syndrome, angina pectoris, cardiac dysrhythmias, inflammatory heart diseases including endocarditis, pericarditis and constrictive pericarditis, myocarditis, myocardial infarct, postmyocardial infarction syndrome, left ventricular dilation, post ischemic reperfusion injury, shock and collapse including septic, allergic, post traumatic and hemodynamic shock, amniotic fluid embolism (Robillard, J.; Gauvin, F.; Molinaro, G.; Leduc, L.; Adam, A.; Rivard, G. E. *Am J Obstet Gynecol.* 2005 October; 193(4):1508-12). systemic inflammatory response syndrome (SIRS) including SIRS caused by heartlung bypass during surgery, sepsis and internal and external complications during cardiopulmonary bypass surgery (including but not limited to adverse hemodynamic effects following protamine sulfate reversal of heparine (Pretorius, M.; Scholl, F. G.; McFarlane, J. A.; Murphey, L. J.; Brown, N. J. *Clin Pharmacol Ther.* 2005 November; 78(5):477-85).

Blood diseases: Within the present application the term "blood diseases" encompasses, but is not limited to, disorders such as coagulation, disseminated intravascular coagulopathy, hemorrhage, hemorrhagic diathesis, hypercholesterolemia and hyperlipemia, hypovolemic shock, paroxysmal nocturnal haemoglobinuria.

Lymphatic diseases: Within the present application the term "Lymphatic diseases" as used herein encompasses, but is not limited to, splenomegaly, lymphangitis, lymphadenitis and hyperplastic adenoids.

Disorders of the central nervous system: Within the present application the term "disorders of the central nervous system" encompasses, but is not limited to, disorders such as inflammatory diseases of the central nervous system including encephalitis, meningitis, encephalomyelitis, meningoencephalitis, hydrocephalus, amyotrophic lateral sclerosis, spinal cord trauma, spinal cord edema, demyelinating diseases of the nervous system, multiple sclerosis, acute and chronic neuro-degenerative disorders including aging, Alzheimer's disease and Parkinson's disease, neuritis, and peripheral neuropathy, depressions, anorexia, anxiety and schizophrenia, sleep disorders.

Brain disorders: Within the present application the term "brain disorders" encompasses, but is not limited to, disorders including nootropic or cognition enhancement, cerebral amyloid angiopathy, stroke, head and brain trauma, traumatic brain injury (Marmarou, A.; Guy, M.; Murphey, L.; Roy, F.; Layani, L.; Combal, J. P.; Marquer, C.; American Brain Injury Consortium *J Neurotrauma* 2005 December; 22(12):1444-55), brain tumor, cerebral heat damage, cerebral ischemia, cerebral hemorrhage, post traumatic and post ischemic cerebral edema, general brain edema, acute mountain sickness and preferably high altitude cerebral edema (HACE), cytotoxic brain edema, vasogenic brain edema, post-surgical brain edema, brain edema associated with metabolic diseases, increase of permeability of blood-brain barrier or blood-brain tumor barrier.

Musculoskeletal system diseases: Within the present application the term "musculoskeletal system diseases" encompasses, but is not limited to, disorders such as inflammatory musculoskeletal disorders, arthrosis, osteoarthrosis, osteoarthritis, chondroporosis after joint trauma or relatively long immobilization of a joint after meniscus or patella injuries or torn ligaments, rheumatoid arthritis of whatever type, etiology, or pathogenesis including acute arthritis, acute gouty arthritis, chronic inflammatory arthritis, degenerative arthritis, infectious arthritis, Lyme arthritis, proliferative arthritis, vertebral arthritis, septic arthritis, psoriatic arthritis, chronic polyarthritis, rheumatism, Sjogren's syndrome, lumbago, spondylitis, spondylarthritis, ankylosing spondylitis, osteomyelitis, sprain, teno-synovitis, inflammation-induced bone resorption, fracture or the like, osteoporosis, musculoskeletal pain and hardening, spinal disk syndrome.

Allergy disorders: Within the present application the term "allergy disorders" encompasses, but is not limited to, disorders such as general allergic reactions, food allergy, anaphylactic shock, allergic contact hypersensitivity, allergic skin reactions, allergic asthma, vernal conjunctivitis and seasonal or perennial allergic rhinitis (Summers, C. W.; Pumphrey, R. S.; Woods, C. N.; McDowell, G.; Pemberton, P. W.; Arkwright, P. D. *J Allergy Clin Immunol.* 2008, 121(3), 632-638)

Pain: Within the present application the term "pain" encompasses, but is not limited to, centrally and peripherally mediated pain, vascular pain, visceral pain, inflammatory mediated pain, neuralgic pain, referred pain, nociceptive pain, reflectory pain, psychosomatic pain, acute pain such as caused by acute injury, trauma or surgery of bones, muscle, tissue, soft tissue, organs, pain after insect bites, post-stroke pain syndrome, post-surgery pain, progressive disease related pain, chronic pain such as caused by neuropathic pain conditions (including but not limited to complex regional pain syndrome (WO00/75107 A2; Yamaguchi-Sase, S.; Hayashi, I.; Okamoto, H.; Nara, Y.; Matsuzaki, S.; Hoka, S.; Majima, M. *Inflamm. Res.* 2003, 52, 164-9; Petersen, M.; Eckert, A. S.; Segond von Banchet, G.; Heppelmann, B.; Klusch, A.; Kniffki, K. D. *Neuroscience* 1998, 83, 949-59; Birklein, F.; Schmelz, M.; Schifter, S.; Weber, M. *Neurology* 2001, 57, 2179-84; Weber, M.; Birklein, F.; Neundorfer, B.; Schmelz, M. *Pain* 2001, 91, 251-7), causalgia, morbus sudeck, reflex sympathetic dystrophy), diabetic peripheral neuropathy, post-herpetic neuralgia, trigeminal neuralgia, cancer-related pain, pain associated with rheumatoid arthritis, osteoarthritis (Bond, A. P.; Lemon, M.; Dieppe, P. A.; Bhoola, K. D. *Immunopharmacology* 1997, 36, 209-16; Cassim, B.; Naidoo, S.; Ramsaroop, R.; Bhoola, K. D. *Immunopharmacology* 1997, 36, 121-5; Calixto, J. B.; Cabrini, D. A.; Ferreira, J.; Campos, M. M. *Pain* 2000, 87, 1-5; Kaneyama, K.; Segami, N.; Sato, J.; Fujimura, K.; Nagao, T.; Yoshimura, H. *J. Oral. Maxillofac. Surg.* 2007, 65, 242-7), teno-synovitis, gout, menstruation and angina, fibromyalgia, ocular pain, back pain, headache, cluster headache, migraine (Ebersberger, A.; Ringkamp, M.; Reeh, P. W.; Handwerker, H. O. *J Neurophysiol.* 1997 June; 77(6):3122-33), inflammatory pain, which may be associated with acute inflammation or chronic inflammation. Inflammatory pain includes but is not limited to neuropathic pain, ischemic pain, pain induced by arthritis, muscle pain induced by acute or chronic inflammation, neuralgia caused by acute or chronic inflammation, hyperalgesia. Also chemotherapy-induced peripheral neuropathy, hyperalgesia, opioid-induced hyperalgesia and fever. Furthermore, compounds of the invention are useful as analgesic agent for use during general and monitored anesthesia.

Infectious diseases: Within the present application the term "infectious diseases" encompasses, but is not limited to, diseases including those mediated by bacteria, viruses, fungi, parasites, protozoa, prions or mycobacterial infections. Particularly, the present invention is useful for the treatment of bacterial infections caused by *Streptococcus, Escherichia, Salmonella, Staphylococcus, Klebsiella, Moracella, Haemophilus* and *Yersinia*. Examples of bacterial infections intended to be within the scope of the present invention include, but are not limited to diseases such as pestis, sepsis, epidemic typhus, food poisoning, tetanus, scarlet red, whooping cough, diphtheria. Examples of viral infections intended to be within the scope of the present invention include, but are not limited to diseases such chickenpox and herpes zoster, AIDS, influenza, small pox, and children diseases such as measles, rubella, mumps, acute anterior poliomyelitis. The present invention is useful for the treatment of protozoa and parasites infections caused by *Schistosoma mansoni, Dermatofagoides farinae*, and *Plasmodium* inducing Malaria. Examples of prion infections intended to be within the scope of the present invention include, but are not limited to diseases such bovine spongiform encephalopathy (BSE), Creutzfeldt Jacob disease and kuru, dengue fever, hemorrhagic fever.

Inflammatory disorders: Within the present application the term "inflammatory disorders" encompasses, but is not limited to, disorders such as acute-phase reaction, local and systemic inflammation and inflammation caused by other diseases whatever type, etiology or pathogenesis and caused by those inflammatory diseases specified within this application.

Injuries: Within the present application the term "injuries" encompasses, but is not limited to, multiple trauma, head trauma, lung injuries, external, internal and surgery wounds.

Immunology disorders: Within the present application the term "immunology disorders" encompasses, but is not limited to, disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, vasculitis, delayed graft function, lupus.

Cancers: Within the present application the term "cancers" encompasses, but is not limited to, disorders such as solid tumor cancer including breast cancer, lung cancer (non-small-cell lung cancer and small-cell lung cancer), prostate cancer, cancers of the oral cavity and pharynx (lip, tongue, mouth, pharynx), esophagus, stomach, small intestine, large intestine, colon, rectum, gallbladder and biliary passages, pancreas, larynx, lung, bone, osteosarcoma, connective tissue, skin cancer including Kaposi's syndrome, melanoma and skin metastasis, epidermoid cancer, basal cell carcinoma, cervix uteri, corpus endometrium, cancer of ovary, testis, bladder, ureter and urethra, kidney, eye, brain and central nervous system, pseudotumor cerebri, sarcoma, sarcoid, thyroid and other endocrine glands (including but not limited to carcinoid tumors), Hodgkin's disease, non-Hodgkin's lymphomas, multiple myeloma, hematopoetic malignancies including leukemias and lymphomas including lymphocytic, granulocytic and monocytic lymphomas, tumor invasion, metastasis, ascites, tumor growth and angiogenesis.

Hereditary diseases: Within the present application the term "hereditary diseases" encompasses, but is not limited to, disorders such as hereditary angioedema (Davis, A. E. et al., 3rd *Transfus. Apher. Sci.* 2003, 29, 195-203; Zuraw, B. L. *Immunol. Allergy Clin. North Am.* 2006, 26, 691-708; Bas, M. et al. *Allergy* 2006, 61, 1490-2) and angioneurotic edema, chondrocalcinosis, Huntington's disease, mucoviscidosis.

Edema: Within the present application the term "edema" encompasses, but is not limited to, general edema and edema caused by inflammation, Factor XII deficiency-induced edema, other drugs, e.g. drug induced angioedema, including but not limited to angiotensin-converting enzyme inhibitor-induced angioedema (Mathelier-Fusade, P. *Clin. Rev. Allergy Immunol.* 2006, 30, 19-23; Finley, C. J. et al. *Am. J. Emerg. Med.* 1992, 10, 550-2; Bielory, L. et al. *Allergy Proc.* 1992, 13, 85-7), infection, burns, injuries, trauma, frostbite, surgery, distorsions, fractures, exposure to high altitude (e.g. high altitude pulmonary edema (HAPE) and high altitude cerebral edema (HACE)), hereditary, autoimmune and other diseases and disorders, particularly but not limited to those disorders specified in this application, stress-induced edema (pronounced swelling) of gut.

Capillary leak syndrome(s): Within the present application the term "capillary leak syndrome(s)" encompasses, but is not limited to, systemic capillary leak syndrome in sepsis (Marx, G. *Eur J Anaesthesiol.* 2003 20(6):429-42; Traber, D. L. *Crit Care Med.* 2000, 28(3):882-3), burn (Jonkam, C. C.; Enkhbaatar, P.; Nakano, Y.; Boehm, T.; Wang, J.; Nussberger, J. Esechie, A.; Traber, L. D.; Herndon, D.; Traber, D. L. *Shock.* 2007 December; 28(6):704-9), allergy, drug/toxin-induced conditions, organ transplantation and IL-2 cytokine therapy.

The compound according to the present invention can also be used as or for the manufacture of a diagnostic agent. Such a diagnostic agent is particularly useful in the diagnosis of the diseases and conditions disclosed herein, which can be addressed by the compound of the present invention for therapeutic and or prophylactic purposes. The compound according to the present invention has also utility in specific methodology and diagnostics as disclosed herein below.

Methodology and diagnostics: Compounds of the invention can be labeled by isotopes, fluorescence or luminescence markers, antibodies or antibody fragments, any other affinity label like nanobodies, aptamers, peptides etc., enzymes or enzyme substrates. These labeled compounds of this invention are useful for mapping the location of bradykinin receptors in vivo, ex vivo, in vitro and in situ (e.g. in tissue sections via autoradiography) and as radiotracers for positron emission tomography (PET) imaging, single photon emission computerized tomography (SPECT) and the like to characterize those receptors in living subjects or other materials.

The present invention also pertains to methods for altering the signal-transducing activity of bradykinin receptors in vitro and in vivo. For instance, compounds of the present invention and labeled derivatives thereof can be used as standard and reagent in determining the ability of a potential pharmaceutical to bind to the BK B2 receptor.

The present invention also provides methods for localizing or detecting a BK B2 receptor in a tissue, preferably a tissue section, which methods involve contacting the tissue sample containing BK B2 receptor with a detectably labeled compound according to the present invention under conditions that permit binding of the compound to the BK B2 receptor and detecting the bound compound. Such methods and their respective conditions are known to those skilled in the art and include, for example, the binding assay disclosed in Example 14.

The present invention further provides a method for treating a patient suffering from a condition or disease responsive to BK B2 receptor modulation as mentioned above. The method for the treatment of a subject which is in need of such treatment comprises the administration of a compound according to the invention, e.g. according to any of [1] to [25], a pharmaceutically acceptable salt thereof, a pharmaceutical composition as disclosed herein, or a combination preparation as disclosed herein. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to BK B2 receptor modulation" if modulation of BK B2 receptor activity results in alleviation of the condition or a symptom thereof. Patients may include but are not limited to primates (especially humans), domesticated companion animals (such as dogs, cats, horses) and livestock (such as cattle, pigs, sheep), with dosages as described herein.

The compounds of general formula (I) according to the present invention have improved properties when compared to BK B2 receptor antagonists known in the state of the art, especially, one or more improved pharmacokinetic and/or physiochemical properties, including, for example, bioavailability, metabolic stability, improved activity/selectivity, low toxicity, and low drug interaction. Accordingly, the compound (or pharmaceutically acceptable salt thereof), the pharmaceutical composition, or the combination preparation disclosed herein can be used as medicament. For instance, the compound (or pharmaceutically acceptable salt thereof), the pharmaceutical composition, or the combination preparation disclosed herein can be used in the treatment and/or prevention of a condition responsive to BK B2 receptor modulation, including, for example, the conditions listed above.

The present invention is now further illustrated by the following examples from which further features, embodiments and advantages of the present invention may be taken. However, the invention should not be construed to be limited to the examples, but encompasses the subject-matter defined in the claims.

EXAMPLES

Abbreviations used in the following synthesis examples are as follows:

ACN is acetonitrile
Boc is tert-Butyloxycarbonyl
DCM is dichloromethane
DIPEA is ethyl-diisopropyl-amine
DMF is dimethylformamide
EA is ethyl acetate
HATU is (1-[bis(dimethylamino)methylene]-1H-1,2,3-triazolo[4,5-b]pyridinium 3-oxide hexafluorophosphate
HPLC is high performance liquid chromatography
$R_f$ is retention factor
NMP is N-methylpyrrolidone
RT is room temperature
TBAF is tetrabutylammonium fluoride
THF is tetrahydrofurane
TLC is thin layer chromatography
sat. is saturated Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention.

Example 1: Preparation of Compound No. 1

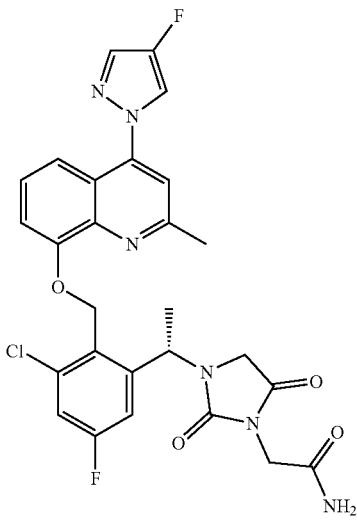 [SMILES: Cc1cc(-n2cc(F)cn2)c2cccc(OCc3c(Cl)cc(F)cc3[C@H](C)N3CC(=O)N(CC(N)=O)C3=O)c2n1]

(S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide Step A. Synthesis of methyl 3-amino-5-fluoro-2-methylbenzoate Methyl 5-fluoro-2-methyl-3-nitrobenzoate [Gillmore, A. T. et al. Org. Process Res. Dev. 2012, 16, 1897-1904] (4.69 g; 22 mmol) was dissolved in MeOH (100 mL) and palladium on activated charcoal—10% Pd (200 mg) was added. The solution was flushed and evacuated three times with nitrogen before it was flushed with hydrogen. The reaction mixture was vigorously stirred under 1 atm of hydrogen. After completion of the reaction as indicated by TLC (21 h) the solution was filtered over silica gel. The filter cake was washed with methanol (5×20 mL). The filtrate was concentrated under reduced pressure and the residue was purified by flash chromatography on silica gel (elution with EA/heptane) to yield the title compound. MS (m/z): 184.0 [M+H$^+$].

Step B. Synthesis of methyl 3-chloro-5-fluoro-2-methylbenzoate

NaNO$_2$ (1.68 g, 24.4 mmol) was added to a solution of methyl 3-amino-5-fluoro-2-methylbenzoate (4.00 g, 18.8 mmol) in half-concentrated aqueous HCl (400 mL) at 0° C. After stirring for 5 min at 0° C., CuCl (3.72 g, 37.5 mmol) was added to the reaction mixture. After stirring for 2 h at 0° C., the reaction mixture was extracted with DCM (2×100 mL). The combined organic layers were washed with concentrated aqueous NaHCO$_3$-solution (1×), dried over Na$_2$SO$_4$, filtered, and concentrated in vacuo. The residue was purified by flash chromatography on silica gel (elution with DCM/heptane) to give the title compound.

Step C. Synthesis of methyl 2-(bromomethyl)-3-chloro-5-fluorobenzoate

Benzoyl peroxide (26 mg, 0.11 mmol) and N-bromosuccinimide (210 mg, 1.18 mmol) were added to a stirred solution of methyl 3-chloro-5-fluoro-2-methylbenzoate (200 mg, 0.99 mmol) in benzene (7.0 mL). After stirring at reflux for 1.5 h, the reaction mixture was diluted with EA (20 mL) and washed with 10% aqueous $Na_2S_2O_3$ (1×5 mL) solution. The organic layer was dried over $Na_2SO_4$, filtered, and concentrated in vacuo to give the title compound.

Step D. Synthesis of methyl 3-chloro-5-fluoro-2-((4-methoxyphenoxy)methyl)benzoate $Cs_2CO_3$ (617 mg, 3.20 mmol) was added to a stirred solution of 2-(bromomethyl)-3-chloro-5-fluorobenzoate (300 mg, 1.07 mmol) and 4-methoxyphenol (172 mg, 1.39 mmol) in ACN (7.0 mL). After stirring overnight at RT, the reaction mixture was filtered and concentrated in vacuo. The residue was purified by flash chromatography on silica gel (elution with EA/heptane) to give the title compound. MS (m/z): 342.1 [M+$NH_4^+$].

Step E. Synthesis of 3-chloro-5-fluoro-2-((4-methoxyphenoxy)methyl)benzoic Acid

A solution of LiOH (2.37 g, 57 mmol) in water (50 mL) was added to a stirred solution of methyl 3-chloro-5-fluoro-2-((4-methoxyphenoxy)methyl)benzoate (9.16 g, 28 mmol) in dioxane (100 mL) at 0° C. After stirring for 2 h at RT the reaction mixture was concentrated in vacuo and the pH value adjusted to 1-2 by the addition of conc. aqueous HCl. The mixture was extracted with DCM (3×100 mL)), the combined organic layers were dried over $Na_2SO_4$, filtered, and concentrated in vacuo to give the title compound.

Step F. Synthesis of 1-(3-chloro-5-fluoro-2-((4-methoxyphenoxy)methyl)phenyl)ethanone A solution of methyllithium (1.6 M, 30.2 mL) in diethylether was added dropwise to a solution of 3-chloro-5-fluoro-2-((4-methoxyphenoxy)methyl)benzoic acid (5.00 g, 16 mmol) in anhydrous diethylether (110 mL) at 0° C. After stirring for 30 min at 0° C., the reaction was quenched by the addition of sat. aqueous $NH_4Cl$ (15 mL) at 0° C. The reaction mixture was diluted with water (15 mL), the organic layer was separated and the aqueous layer extracted with diethylether (3×50 mL). The combined organic layers were dried over $Na_2SO_4$, filtered, and concentrated in vacuo. The residue was purified by flash chromatography on silica gel (elution with EA/heptane) to give the title compound.

Step G. Synthesis of (R)—N—((S)-1-(3-chloro-5-fluoro-2-((4-methoxyphenoxy) methyl) phenyl) ethyl)-2-methylpropane-2-sulfinamide Titan(IV)ethoxide (2.53 mL, 12.1 mmol) was added dropwise under an argon atmosphere to a solution of 1-(3-chloro-5-fluoro-2-((4-methoxyphenoxy)methyl)phenyl)ethanone (1.24 g, 4.02 mmol) and (R)-(+)-2-methyl-2-propanesulfinamide (535.5 mg, 4.42 mmol) in anhydrous THF (10 mL). The mixture was heated under reflux until complete conversion (TLC). Subsequently, the mixture was cooled to 0° C. and L-Selectride (1 M solution, 12.05 mL, 12.05 mmol) was added dropwise. The mixture was stirred at this temperature until complete conversion (TLC). Subsequently, methanol (~10 mL) was added until evolution of gas stopped. The solution was poured into sat. aqueous NaCl solution (30 mL). Then, the mixture was filtrated over a pad of Celite and carefully rinsed with DCM. The filtrate was washed with sat. aqueous NaCl solution. The aqueous layer was extracted with DCM. The combined organic layers were dried over $Na_2SO_4$, filtrated, and evaporated to dryness. The remaining residue was purified by flash chromatography on silica gel (elution with EA/heptane) to give the title compound. MS (m/z): 458.2 [M+$HCO_2^-$].

Step H. Synthesis of (S)-1-(3-chloro-5-fluoro-2-((4-methoxyphenoxy) methyl) phenyl) ethanamine A solution of (R)—N—((S)-1-(3-chloro-5-fluoro-2-((4-methoxyphenoxy)methyl)phenyl)ethyl)-2-methylpropane-2-sulfinamide (2.19 g, 5.29 mmol) in 3 M methanolic HCl (3.53 mL, 10.6 mmol) was stirred at room temperature until complete conversion (TLC). The solution was concentrated in vacuo. The remaining residue was dissolved in DCM (5 mL) and washed with sat. aqueous $NaHCO_3$ solution (6 mL) and water (6 mL). The organic layer was dried over $Na_2SO_4$, filtered and concentrated in vacuo to give the title compound. MS (m/z): 354.4 [M+$HCO_2^-$].

Step I. Synthesis of (S)-ethyl 2-(1-(3-chloro-5-fluoro-2-((4-methoxyphenoxy) methyl) phenyl) ethylamino)acetate (S)-1-(3-Chloro-5-fluoro-2-((4-methoxyphenoxy)methyl) phenyl)ethanamine (160 mg, 516.5 µmol), ethylglyoxalate solution, 50% in toluene (112.6 µl, 568.2 µmot) and borane-pyridine-complex (78.3 µl, 775 µmol) were dissolved in propan-2-ol (5 mL). A 0.5 M aqueous HCl-solution (approx. 10 µl) was added and the reaction mixture was stirred at RT overnight. After TLC indicated complete reaction the solution was poured over a SCX-cartridge (Phenomenex, Strata SCX, 0.6 mmol/g) and rinsed with methanol. Then, the resin was eluted with 8 M methanolic ammonia solution (3×) to yield the crude product after evaporation of the solvent. The residue was purified by flash chromatography on silica gel (elution with EA/heptane) to give the title compound. MS (m/z): 396.1 [M+$H^+$].

Step J. Synthesis of (S)-ethyl 2-(1-(1-(3-chloro-5-fluoro-2-((4-methoxyphenoxy) methyl) phenyl) ethyl)-3-(2-ethoxy-2-oxoethyl)ureido)acetate (S)-Ethyl 2-(1-(3-chloro-5-fluoro-2-((4-methoxyphenoxy)methyl)phenyl)ethylamino)acetate (53.50 mg, 135.4 µmol) was dissolved in pyridine (62.5 µL) and DCM (2.5 mL) and ethyl 2-isocyanatoacetate (33.4 µL, 149 µmol) was added. The reaction mixture was stirred at RT until TLC indicated complete reaction. Then the reaction was quenched with water and extracted with DCM (3×). The combined organic layers were dried over $Na_2SO_4$, filtered and evaporated to dryness under reduced pressure to give the title compound. MS (m/z): 547.3 [M+Na].

Step K. Synthesis of (S)-2-(3-(1-(3-chloro-5-fluoro-2-((4-methoxyphenoxy) methyl) phenyl) ethyl)-2,5-dioxoimidazolidin-1-yl)acetamide (S)-Ethyl 2-(1-(1-(3-chloro-5-fluoro-2-((4-methoxyphenoxy)methyl)phenyl)ethyl)-3-(2-ethoxy-2-oxoethyl)ureido) acetate (70.97 mg, 135.2 µmol) was dissolved in methanol (1 mL) and 8 M methanolic ammonia solution (1 mL) and stirred at RT overnight. The reaction was quenched with water and extracted with DCM (3×). The combined organic layers were dried over $Na_2SO_4$, filtered and evaporated to dryness under reduced pressure to give the title compound. MS (m/z): 450.4 [M+$H^+$].

Step L. Synthesis of (S)-2-(3-(1-(3-chloro-5-fluoro-2-(hydroxymethyl)phenyl)ethyl)-2,5-dioxoimidazolidin-1-yl)acetamide A solution of ammonium cerium(IV) nitrate (185 mg, 337 µmol) in H₂O (350 µl) was added to a stirred solution of (S)-2-(3-(1-(3-chloro-5-fluoro-2-((4-methoxyphenoxy)methyl) phenyl) ethyl)-2,5-dioxoimidazolidin-1-yl)acetamide (60.7 mg, 135 µmol) in ACN (1.4 mL) at 0° C. After stirring for 10 min at 0° C., the reaction was quenched by the addition of brine (1.7 mL) and H₂O (0.7 mL). The mixture was extracted with EA (3×5 mL), the combined organic layers were dried over Na₂SO₄, filtered, and concentrated in vacuo. The residue was purified by flash chromatography on silica gel (elution with EA/heptane) to give the title compound. MS (m/z): 366.1 [M+Na].

Step M. Synthesis of (S)-2-(3-(1-(3-chloro-2-(chloromethyl)-5-fluorophenyl)ethyl)-2,5-dioxoimidazolidin-1-yl)acetamide SOCl₂ (20.21 mg, 12.32 µl) and water (1 µL) were added to a stirred solution of (S)-2-(3-(1-(3-chloro-5-fluoro-2-(hydroxymethyl)phenyl)ethyl)-2,5-dioxoimidazolidin-1-yl) acetamide (29 mg, 85 µmol) in DCM (1 mL) at RT. After complete reaction (TLC) the solvent was removed in vacuo to give the title compound. MS (m/z): 384.4 [M+Na].

Step N. Synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide Cs₂CO₃ (73.4 mg, 225 µmol) was added to a stirred solution of (S)-2-(3-(1-(3-chloro-2-(chloromethyl)-5-fluorophenyl)ethyl)-2,5-dioxoimidazolidin-1-yl)acetamide (27.2 mg, 75 µmol) and 4-(4-fluoro-1H-pyrazol-1-yl)-2-methylquinolin-8-ol (18.27 mg, 75 µmol) in ACN (1 mL). After stirring overnight at RT, the reaction mixture was filtered and concentrated in vacuo. Purification of the residue by HPLC afforded the title compound. MS (m/z): 569.1 [M+H⁺].

Step O. Synthesis 4-(4-fluoro-1H-pyrazol-1-yl)-8-methoxy-2-methylquinoline

K₂CO₃ (4.99 g, 36.1 mmol) was added to a stirred mixture of 4-chloro-8-methoxy-2-methylquinoline (5.00 g, 24.0 mmol) and 4-fluoro-1H-pyrazole (3.85 g, 28.8 mmol) in anhydrous NMP (12 mL). After stirring for 48 h at 140° C. the reaction mixture was cooled to RT and filtered. The residue was rinsed with DMF (13 mL). Then, water (90 mL) was added to the combined filtrates. The precipitate was filtered off and purified by flash chromatography on silica gel (elution with DCM/methanol) to give the title compound. MS (m/z): 258.0 [M+H⁺].

Step P. Synthesis of 4-(4-fluoro-1H-pyrazol-1-yl)-2-methylquinolin-8-ol

A solution of 4-(4-fluoro-1H-pyrazol-1-yl)-8-methoxy-2-methylquinoline (5.51 g, 21.4 mmol) in anhydrous toluene (37.8 mL) was warmed to 80° C. and added dropwise to a vigorously stirred mixture of AlCl₃ (8.58 g, 64.3 mmol) in anhydrous toluene (32.4 mL). After stirring for 8 h at 80° C. the reaction mixture was cooled to 0° C. and quenched by the addition of water (106 mL) and conc. aqueous NH₃ (27 mL). After stirring overnight at RT, the mixture was centrifuged. The supernatant was extracted with EA (3×200 mL) and the combined organic layers were dried over Na₂SO₄, filtered, and concentrated in vacuo. The residue was purified by flash chromatography on silica gel (elution with DCM/methanol) to give the title compound. MS (m/z): 244.3 [M+H⁺].

Example 2: Preparation of Compound No. 2

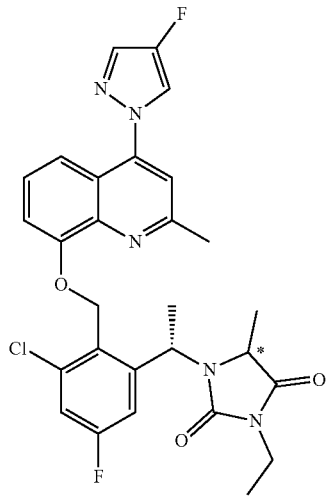 [SMILES: CCN1C(=O)C(C)N([C@@H](C)c2cc(F)cc(Cl)c2COc2cccc3c(-n4cc(F)cn4)cc(C)nc23)C1=O]

Diastereomer B of 1-((S)-1-(3-chloro-5-fluoro-2-((4-(4-fluoro-1H-pyrazol-1-yl)-2-methylquinolin-8-yloxy)methyl)phenyl)ethyl)-3-ethyl-5-methylimidazolidine-2,4-dione

Step A. Synthesis of diasteromers A and B of methyl 2-((S)-1-(3-chloro-5-fluoro-2-((4-methoxyphenoxy)methyl)phenyl)ethylamino)propanoate (S)-1-(3-Chloro-5-fluoro-2-((4-methoxyphenoxy)methyl) phenyl)ethanamine (220 mg, 710 µmol), methyl pyruvate (72.0 µL, 79.8 mg, 781 µmol) and borane-pyridine-complex (107.6 µl, 1.06 mmol) were dissolved in propan-2-ol (5 mL). Ca. 10 µL 0.5 M aqueous HCl-solution were added and the reaction mixture was stirred at RT overnight. After completion of the reaction (TLC) the solution was poured over a SCX-cartridge (Phenomenex, Strata SCX, 0.6 mmol/g) and eluted with methanol. Then the resin was washed with ca. 8M methanolic ammonia solution to get the crude product after evaporation of the solvent. The remaining residue was purified by flash chromatography on silica gel (elution with EA/heptane) to give the pure isomeric title compounds.

Diastereomer A: MS (m/z): 396.1 [M+H⁺], R_f (TLC, EA/heptane 1:1)=0.55.

Diastereomer B: MS (m/z): 418.3 [M+Na], R_f (TLC, EA/heptane 1:1)=0.51.

Step B. Synthesis of diastereomer B of methyl 2-(1-((S)-1-(3-chloro-5-fluoro-2-((4-methoxyphenoxy)methyl)phenyl)ethyl)-3-ethylureido)propanoate Diastereomer B of methyl 2-((S)-1-(3-chloro-5-fluoro-24 (4-methoxyphenoxy)methyl)phenyl) ethylamino)propanoate (37.15 mg, 94.0 µmol) was dissolved in a mixture of pyridine (62.5 µL) and DCM (2.5 mL) and reacted with ethyl isocyanate (205.0 µl, 2.35 mmol) according to the synthesis of (S)-ethyl 2-(1-(1-(3-chloro-5-fluoro-2-((4-methoxyphenoxy)methyl)phenyl)ethyl)-3-(2-ethoxy-2-oxoethyl)ureido) acetate to give the title compound. MS (m/z): 387.0 [M+H$^+$].

Step C. Synthesis of Diastereomer B of 1-((S)-1-(3-chloro-5-fluoro-2-((4-methoxyphenoxy)methyl)phenyl)ethyl)-3-ethyl-5-methylimidazolidine-2,4-dione Diastereomer B of methyl 2-(1-((S)-1-(3-chloro-5-fluoro-2-((4-methoxyphenoxy)methyl) phenyl)ethyl)-3-ethylureido)propanoate (42.3 mg, 90.6 µmol) was dissolved in methanol (1 mL) and reacted with ca. 8M methanolic ammonia solution (1 mL) according to the synthesis of (S)-2-(3-(1-(3-chloro-5-fluoro-2-((4-methoxyphenoxy)methyl)phenyl)ethyl)-2,5-dioxoimidazolidin-1-yl)acetamide to give the title compound. MS (m/z): 435.0 [M+H$^+$].

Step D. Synthesis of diastereomer B of 1-((S)-1-(3-chloro-5-fluoro-2-(hydroxymethyl) phenyl)ethyl)-3-ethyl-5-methylimidazolidine-2,4-dione Diastereomer B of 1-((S)-1-(3-chloro-5-fluoro-2-((4-methoxyphenoxy)methyl)phenyl)ethyl)-3-ethyl-5-methylimidazolidine-2,4-dione (38 mg, 88 µmol) was reacted with ammonium cerium(IV) nitrate (120 mg, 219 µmol) according to the synthesis of (S)-2-(3-(1-(3-chloro-5-fluoro-2-(hydroxymethyl)phenyl)ethyl)-2,5-dioxoimidazolidin-1-yl)acetamide to give the title compound. MS (m/z): 329.0 [M+H$^+$].

Step E. Synthesis of diastereomer B of 1-((S)-1-(3-chloro-2-(chloromethyl)-5-fluorophenyl)ethyl)-3-ethyl-5-methylimidazolidine-2,4-dione Diastereomer B of 1-((S)-1-(3-chloro-5-fluoro-2-(hydroxymethyl)phenyl)ethyl)-3-ethyl-5-methylimidazolidine-2,4-dione (29.2 mg, 85 µmol) was reacted with SOCl$_2$ (12.32 µL, 20.21 mg, 170 µmol) according to the synthesis of (S)-2-(3-(1-(3-chloro-2-(chloromethyl)-5-fluorophenyl)ethyl)-2,5-dioxoimidazolidin-1-yl)acetamide to give the title compound. MS (m/z): 347.0 [M+H$^+$].

Step F. Synthesis of Diastereomer B of 1-((S)-1-(3-chloro-5-fluoro-2-((4-(4-fluoro-1H-pyrazol-1-yl)-2-methylquinolin-8-yloxy)methyl)phenyl)ethyl)-3-ethyl-5-methylimidazolidine-2,4-dione Diastereomer B of 1-((S)-1-(3-chloro-2-(chloromethyl)-5-fluorophenyl)ethyl)-3-ethyl-5-methylimidazolidine-2,4-dione (10 mg, 29 µmol) was reacted with 4-(4-fluoro-1H-pyrazol-1-yl)-2-methylquinolin-8-ol (7.0 mg, 29 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 554.0 [M+H$^+$].

Example 3: Preparation of Compound No. 3

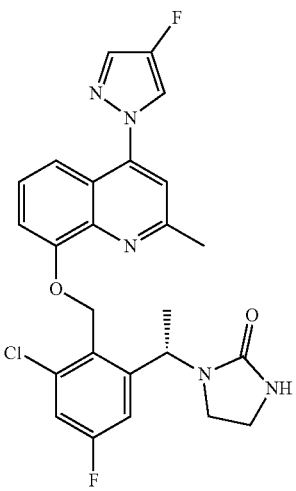 [SMILES: Cc1cc(-n2cc(F)cn2)c2cccc(OCc3c(Cl)cc(F)cc3[C@H](C)N3CCNC3=O)c2n1]

(S)-1-(1-(3-chloro-5-fluoro-2-((4-(4-fluoro-1H-pyrazol-1-yl)-2-methylquinolin-8-yloxy)methyl)phenyl)ethyl)imidazolidin-2-one Step A. Synthesis of (S)-tert-butyl 2-(1-(3-chloro-5-fluoro-2-((4-methoxyphenoxy) methyl) phenyl) ethylamino)ethylcarbamate (S)-1-(3-Chloro-5-fluoro-2-((4-methoxyphenoxy)methyl) phenyl)ethanamine (100 mg, 323 µmol), N-Boc-2-aminoacetaldehyde (113.1 µl, 355 µmol) and borane-pyridine-complex (48.9 µl, 484 µmol) were dissolved in 2-propanol (4 mL). Approx. 10 µL 0.5 M HCl-solution were added and the reaction mixture was stirred at RT overnight. After completion of the reaction (TLC), sat. aqueous NaHCO$_3$-solution was added and the aqueous phase was extracted with DCM (3×). The combined organic layers were dried over Na$_2$SO$_4$ and, after filtration, evaporated to dryness under reduced pressure. The crude product was purified by flash chromatography on silica gel (elution with EA/heptane) to give the title compound. MS (m/z): 453.7 [M+H$^+$].

Step B. Synthesis of (S)-tert-butyl 2-(1-(3-chloro-5-fluoro-2-((4-methoxyphenoxy)methyl) phenyl)ethylamino)ethylcarbamate (S)-tert-Butyl 2-(1-(3-chloro-5-fluoro-2-((4-methoxyphenoxy)methyl)phenyl) ethylamino) ethylcarbamate (45 mg, 99 µmol) and triethylamine (13.8 µl, 99 µmol) were dissolved in DCM (2 mL). The solution was cooled to 0° C. Under an atmosphere of argon triphosgene (11.8 mg, 40 µmol), dissolved in DCM (1 mL), was added. The reaction mixture was stirred at RT until complete conversion; then quenched with sat. aqueous NH$_4$Cl-solution and extracted with DCM (3×). The combined organic layers were dried over Na$_2$SO$_4$ and, after filtration, evaporated to dryness under reduced pressure. The crude product was purified by flash chromatography on silica gel (elution with EA/heptane) to give the title compound. MS (m/z): 479.2 [M+H$^+$].

Step C. Synthesis of (S)-tert-butyl 3-(1-(3-chloro-5-fluoro-2-(hydroxymethyl)phenyl)ethyl)-2-oxoimidazolidine-1-carboxylate (S)-tert-Butyl 2-(1-(3-chloro-5-fluoro-2-((4-methoxyphenoxy)methyl)phenyl)ethylamino) ethylcarbamate (27.0 mg, 56 µmol) was reacted with ammonium cerium(IV) nitrate (77.3 mg, 141 µmol) according to the synthesis of (S)-2-(3-(1-(3-chloro-5-fluoro-2-(hydroxymethyl)phenyl) ethyl)-2,5-dioxoimidazolidin-1-yl)acetamide to give the title compound. MS (m/z): 395.5 [M+Na$^+$].

Step D. Synthesis of (S)-1-(1-(3-chloro-2-(chloromethyl)-5-fluorophenyl)ethyl)imidazolidin-2-one ((S)-tert-Butyl 3-(1-(3-chloro-5-fluoro-2-(hydroxymethyl)phenyl)ethyl)-2-oxoimidazolidine-1-carboxylate (11.1 mg, 30 µmol) was reacted with SOCl$_2$ (4.32 µL, 7.09 mg, 60 µmol) according to the synthesis of (S)-2-(3-(1-(3-chloro-2-(chloromethyl)-5-fluorophenyl)ethyl)-2,5-dioxoimidazolidin-1-yl)acetamide to give the title compound.

Step E. Synthesis of (S)-1-(1-(3-chloro-5-fluoro-2-((4-(4-fluoro-1H-pyrazol-1-yl)-2-methylquinolin-8-yloxy)methyl)phenyl)ethyl)imidazolidin-2-one (S)-1-(1-(3-Chloro-2-(chloromethyl)-5-fluorophenyl)ethyl)imidazolidin-2-one (9.2 mg, 32 µmol) was reacted with 4-(4-fluoro-1H-pyrazol-1-yl)-2-methylquinolin-8-ol (7.7 mg, 32 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 498.5 [M+H$^+$].

Example 4: Preparation of Compound No. 4

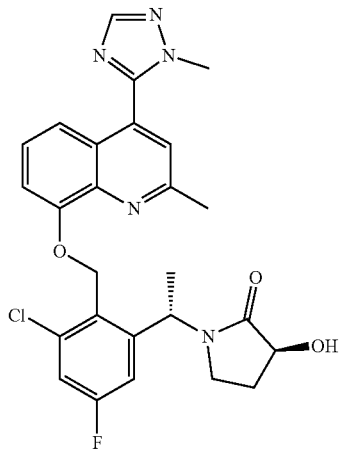 [SMILES: Cc1cc(-c2ncnn2C)c2cccc(OCc3c(Cl)cc(F)cc3[C@H](C)N3CC[C@H](O)C3=O)c2n1]

(S)-1-((S)-1-(3-chloro-5-fluoro-2-((2-methyl-4-(1-methyl-1H-1,2,4-triazol-5-yl)quinolin-8-yloxy)methyl)phenyl)ethyl)-3-hydroxypyrrolidin-2-one Step A. Synthesis of 8-methoxy-2-methyl-4-(1-methyl-1H-1,2,4-triazol-5-yl)quinoline 4-Chloro-8-methoxy-2-methylquinoline (5.00 g, 24.15 mmol), 1-methyl-1,2,4-triazole (42.74 mL, 48.30 mmol), K$_2$CO$_3$ (6.67 g, 48.30 mmol), Pd(OAc)$_2$ (0.54 g, 2.41 mmol), tricyclohexylphosphine tetrafluoroborate (1.87 g, 5.07 mmol), and trimethylacetic acid (2.47 g, 24.15 mmol) were suspended in dry xylene (20 mL). The flask was evacuated and subsequently ventilated with nitrogen. The degassing procedure was repeated twice. The mixture was heated to 140° C. for 18 h. After complete conversion the mixture was evaporated and purified by flash chromatography on silica gel (elution with DCM/methanol) to give the title compound. MS (m/z): 255.4 [M+H$^+$].

Step B. Synthesis of 2-methyl-4-(1-methyl-1H-1,2,4-triazol-5-yl)quinolin-8-ol

A solution of 8-methoxy-2-methyl-4-(1-methyl-1H-1,2,4-triazol-5-yl)quinoline (3.14 g, 12.35 mmol) in anhydrous toluene (25 mL) was warmed to 80° C. and added dropwise to a vigorously stirred mixture of AlCl$_3$ (4.94 g, 37.06 mmol) in anhydrous toluene (25 mL). After stirring for 8 h at 80° C. the reaction mixture was cooled to 0° C. and quenched by the addition of water (68 mL) and subsequently conc. aqueous NH$_3$ until pH 10 (~1.7 mL). The mixture was centrifuged. The supernatant was extracted with EA and the combined organic layers were dried over Na$_2$SO$_4$, filtered, and concentrated in vacuo. The residue was purified by flash chromatography on silica gel (elution with DCM/methanol) to give the title compound. MS (m/z): 239.2 [M–H$^+$].

Step C. Synthesis of (S)-methyl 2-(tert-butyldimethylsilyloxy)-4-oxobutanoate (S)-Methyl 2-(tert-butyldimethylsilyloxy)-4-hydroxybutanoate [Dauben, W. G. et al. *Tetrahedron Letters* 1995, 36, 2385-2388] (195.3 mg, 787.0 µmol) was dissolved in anhydrous dichloromethane (5 mL), then Dess-Martin Periodinane (400.8 mg, 944.6 µcool) was added and the reaction mixture was stirred at RT overnight. The mixture was diluted with DCM and saturated aqueous sodium thiosulfate-solution (5 mL) and saturated aqueous NaHCO$_3$-solution (5 mL). The resulting mixture was vigorously stirred for 1 h. The organic layer was separated and the aqueous layer was extracted with DCM (2×). The combined organic layers were washed with water several times and then dried over Na$_2$SO$_4$. After filtration the solvent was evaporated under reduced pressure and the remaining residue was purified by flash chromatography on silica gel (elution with EA/heptane) to give the title compound.

Step D. Synthesis of (S)-methyl 2-(tert-butyldimethylsilyloxy)-4-((S)-1-(3-chloro-5-fluoro-2-((4-methoxyphenoxy)methyl)phenyl)ethylamino)butanoate (S)-1-(3-Chloro-5-fluoro-2-((4-methoxyphenoxy)methyl)phenyl)ethanamine (50 mg, 161 µmol) was reacted with (S)-methyl 2-(tert-butyldimethylsilyloxy)-4-oxobutanoate (43.7 mg, 178 µmol) and borane-pyridine-complex (24.5 µl, 242.1 µmol) according to the synthesis of (S)-ethyl 2-(1-(3-chloro-5-fluoro-2-((4-methoxyphenoxy)methyl)phenyl)ethylamino)acetate to give the title compound. MS (m/z): 540.4 [M+H$^+$].

Step E. Synthesis of (S)-2-(tert-butyldimethylsilyloxy)-4-((S)-1-(3-chloro-5-fluoro-2-((4-methoxyphenoxy)methyl)phenyl)ethylamino)butanoic Acid A solution of LiOH (10.7 mg, 254.5 µmol) in water (0.5 mL) was added to a stirred solution of (S)-methyl 2-(tert-butyldimethylsilyloxy)-4-((S)-1-(3-chloro-5-fluoro-2-((4-methoxyphenoxy) methyl)phenyl)ethylamino)butanoate (55.0 mg, 101.8 µmol) in THF (1 mL) at 0° C. After stirring for 5 h at RT the reaction mixture was concentrated in vacuo and the pH value adjusted to 1-2 by the addition of conc.

aqueous HCl. The mixture was extracted with EA (3×10 mL)), the combined organic layers were dried over Na$_2$SO$_4$, filtered and concentrated in vacuo to give the title compound. MS (m/z): 526.3 [M+H$^+$].

Step F. Synthesis of (S)-3-(tert-butyldimethylsilyloxy)-1-((S)-1-(3-chloro-5-fluoro-2-((4-methoxyphenoxy)methyl)phenyl)ethyl)pyrrolidin-2-one (S)-2-(tert-Butyldimethylsilyloxy)-4-((S)-1-(3-chloro-5-fluoro-2-((4-methoxyphenoxy) methyl) phenyl) ethylamino) butanoic acid (50.0 mg, 95.0 μmol) was dissolved in anhydrous DMF (5 mL). HATU (72.3, 190.0 μmol) and DIPEA (32.54 μl, 190.0 μmol) were added and the reaction mixture was stirred at room temperature overnight. The reaction was quenched by the addition of saturated aqueous NH$_4$Cl solution and the aqueous layer was extracted with DCM several times. The combined organic layers were washed with saturated aqueous NH$_4$Cl solution, brine and dried over Na$_2$SO$_4$. After filtration the filtrate was evaporated to dryness under reduced pressure and the remaining residue was purified by flash chromatography (eluent: heptane/EA). MS (m/z): 530.2 [M+Na$^+$].

Step G. Synthesis of (S)-1-((S)-1-(3-chloro-5-fluoro-2-((4-methoxyphenoxy)methyl) phenyl)ethyl)-3-hydroxypyrrolidin-2-one (S)-3-(tert-Butyldimethylsilyloxy)-1-((S)-1-(3-chloro-5-fluoro-2-((4-methoxyphenoxy) methyl) phenyl)ethyl)pyrrolidin-2-one (48.3 mg, 95.0 μmol) was dissolved in 5 ml THF and the solution was cooled to 0° C. Tetrabutylammonium fluoride solution (1 M in THF, 104.5 μl, 104.5 μmol) was added dropwise. After completion of the reaction the reaction mixture was diluted with EA. After extraction with brine, drying over Na$_2$SO$_4$ and filtration, the filtrate was evaporated to dryness under reduced pressure and the remaining residue was purified by flash chromatography (eluent: heptane/EA). MS (m/z): 416.2 [M+Na$^+$].

Step H. Synthesis of (S)-1-((S)-1-(3-chloro-5-fluoro-2-(hydroxymethyl)phenyl)ethyl)-3-hydroxypyrrolidin-2-one (S)-1-((S)-1-(3-Chloro-5-fluoro-2-((4-methoxyphenoxy)methyl)phenyl)ethyl)-3-hydroxypyrrolidin-2-one (36.0 mg, 91.4 μmol) was reacted with ammonium cerium(IV) nitrate (125.3 mg, 228.5 μmol) according to the synthesis of (S)-2-(3-(1-(3-chloro-5-fluoro-2-(hydroxymethyl)phenyl) ethyl)-2,5-dioxoimidazolidin-1-yl)acetamide to give the title compound. MS (m/z): 332.2 [M+HCO$_2^-$].

Step I. Synthesis of (S)-1-((S)-1-(3-chloro-2-(chloromethyl)-5-fluorophenyl)ethyl)-3-hydroxypyrrolidin-2-one (S)-1-((S)-1-(3-Chloro-5-fluoro-2-(hydroxymethyl)phenyl)ethyl)-3-hydroxypyrrolidin-2-one (13.0 mg, 45.0 μmol) was reacted with SOCl$_2$ (16.4 μL, 26.9 mg, 226.0 μmol) according to the synthesis of (S)-2-(3-(1-(3-chloro-2-(chloromethyl)-5-fluorophenyl)ethyl)-2,5-dioxoimidazolidin-1-yl)acetamide to give the title compound. MS (m/z): 328.3 [M+Na$^+$].

Step J. Synthesis of (S)-1-((S)-1-(3-chloro-5-fluoro-2-((2-methyl-4-(1-methyl-1H-1,2,4-triazol-5-yl)quinolin-8-yloxy)methyl)phenyl)ethyl)-3-hydroxypyrrolidin-2-one Cs$_2$CO$_3$ (44.0 mg, 135.0 μmol) was added to a stirred solution of (S)-1-((S)-1-(3-chloro-2-(chloromethyl)-5-fluorophenyl)ethyl)-3-hydroxypyrrolidin-2-one (13.8 mg, 45.0 μmol) and 2-methyl-4-(1-methyl-1H-1,2,4-triazol-5-yl)quinolin-8-ol (10.8 mg, 45.0 μmol) in ACN (1.0 mL). After stirring overnight at RT, the reaction mixture was filtered and concentrated in vacuo. Purification of the residue by reverse HPLC afforded the title compound. MS (m/z): 507.9 [M+H$^+$].

Example 5: Preparation of Compound No. 5

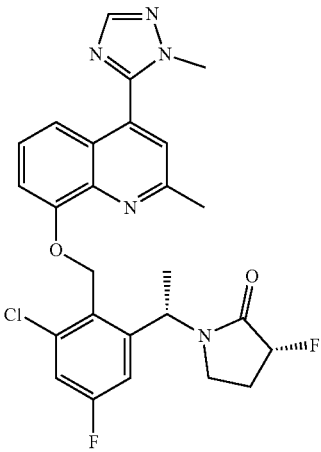 [SMILES: Cc1cc(-c2ncnn2C)c2cccc(OCc3c(Cl)cc(F)cc3[C@H](C)N3CC[C@@H](F)C3=O)c2n1]

(R)-1-((S)-1-(3-chloro-5-fluoro-2-((2-methyl-4-(1-methyl-1H-1,2,4-triazol-5-yl)quinolin-8-yloxy) methyl)phenyl)ethyl)-3-fluoropyrrolidin-2-one Synthesis. (S)-1-((S)-1-(3-Chloro-5-fluoro-2-((2-methyl-4-(1-methyl-1H-1,2,4-triazol-5-yl) quinolin-8-yloxy) methyl)phenyl)ethyl)-3-hydroxypyrrolidin-2-one (8.75 mg, 17.2 μmol) was dissolved in 1 ml toluene and the solution was cooled to 0° C. DBU (3.8 μL, 25.7 μmol) and nonafluoro-1-butanesulfonylfluoride (4.5 μL, 25.5 μmol) were added dropwise. Stirring was continued at 0° C. for another 30 min before the cooling bath was removed. After completion of the reaction, the mixture was poured onto ice/water and the aqueous phase was extracted with ethyl acetate several times. The combined organic layers were washed with brine and dried over Na$_2$SO$_4$. After filtration the solvent was removed in in vacuo and the remaining residue was purified by flash chromatography (eluent: dichloromethane/methanol) to yield the title compound. MS (m/z): 512.0 [M+H$^+$].

Example 6: Preparation of Compound No. 6

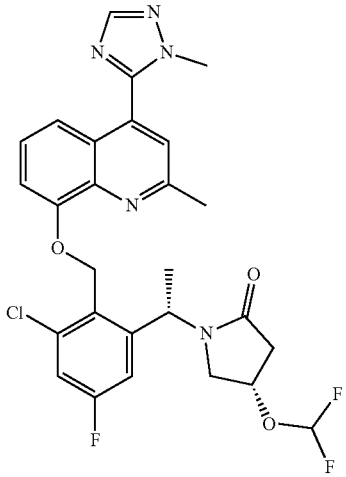

(S)-1-((S)-1-(3-chloro-5-fluoro-2-((2-methyl-4-(1-methyl-1H-1,2,4-triazol-5-yl)quinolin-8-yloxy)methyl)phenyl)ethyl)-4-(difluoromethoxy)pyrrolidin-2-one

Step A. Synthesis of (S)-methyl 3-(tert-butyldimethylsilyloxy)-4-((S)-1-(3-chloro-5-fluoro-2-((4-methoxyphenoxy)methyl)phenyl)ethylamino)butanoate (S)-1-(3-Chloro-5-fluoro-2-((4-methoxyphenoxy)methyl)phenyl)ethanamine (160.0 mg, 516.5 μmol) was reacted with (S)-methyl 3-(tert-butyldimethylsilyloxy)-4-oxobutanoate [Si, Chang-Mei. et al. *Org. Chem. Front.* 2015, 2, 1485-1499] (140.0 mg, 568.2 μmol) according to the synthesis of ((S)-ethyl 2-(1-(3-chloro-5-fluoro-2-((4-methoxyphenoxy)methyl)phenyl) ethylamino)acetate to give the title compound. MS (m/z): 540.4 [M+H$^+$].

Step B. Synthesis of (S)-3-(tert-butyldimethylsilyloxy)-4-((S)-1-(3-chloro-5-fluoro-2-((4-methoxyphenoxy)methyl)phenyl)ethylamino)butanoic Acid (S)-Methyl 3-(tert-butyldimethylsilyloxy)-4-((S)-1-(3-chloro-5-fluoro-2-((4-methoxy-phenoxy)methyl) phenyl) ethylamino)butanoate (195.0 mg, 361.0 μmol) was reacted with lithium hydroxide monohydrate (37.88 mg, 902.54 μmol) according to the synthesis of ((S)-2-(tert-butyldimethylsilyloxy)-4-((S)-1-(3-chloro-5-fluoro-2-((4-methoxyphenoxy)methyl)phenyl) ethylamino)butanoic acid to give the title compound. MS (m/z): 526.3 [M+H$^+$].

Step C. Synthesis of (S)-4-(tert-butyldimethylsilyloxy)-1-((S)-1-(3-chloro-5-fluoro-2-((4-methoxyphenoxy)methyl)phenyl)ethyl)pyrrolidin-2-one (S)-3-(tert-Butyldimethylsilyloxy)-4-((S)-1-(3-chloro-5-fluoro-2-((4-methoxyphenoxy) methyl)phenyl)ethylamino) butanoic acid (182.0 mg, 345.9 μmol) was reacted with HATU (263.0 mg, 691.87 μmol) and DIPEA (89.4 mg, 118 μL, 691.87 μmol) according to the synthesis of (S)-3-(tert-butyldimethylsilyloxy)-1-((S)-1-(3-chloro-5-fluoro-2-((4-methoxyphenoxy)methyl) phenyl)ethyl)pyrrolidin-2-one to give the title compound. MS (m/z): 508.6 [M+H$^+$].

Step D. Synthesis of (S)-1-((S)-1-(3-chloro-5-fluoro-2-((4-methoxyphenoxy)methyl) phenyl)ethyl)-4-hydroxypyrrolidin-2-one (S)-4-(tert-Butyldimethylsilyloxy)-1-((S)-1-(3-chloro-5-fluoro-2-((4-methoxyphenoxy) methyl)phenyl)ethyl)pyrrolidin-2-one (80.0 mg, 157.5 μmol) was reacted with TBAF (1M solution in THF, 173 μl, 173 μmol) according to the synthesis of (S)-1-((S)-1-(3-chloro-5-fluoro-2-((4-methoxyphenoxy)methyl)phenyl)ethyl)-3-hydroxypyrrolidin-2-one to give the title compound. MS (m/z): 416.2 [M+Na$^+$].

Step E. (S)-1-((S)-1-(3-chloro-5-fluoro-2-((4-methoxyphenoxy)methyl)phenyl)ethyl)-4-(difluoromethoxy)pyrrolidin-2-one (S)-1-((S)-1-(3-Chloro-5-fluoro-2-((4-methoxyphenoxy)methyl)phenyl)ethyl)-4-hydroxypyrrolidin-2-one (34.5 mg, 87.6 mmol) was dissolved in ACN (5 mL) and CuI (3.34 mg, 17.52 μmol) was added. The mixture was degassed several times and heated to 50° C. Under an Argon atmosphere 2-(fluorosulfonyl)difluoro-acetic acid (78.0 mg, 45.27 mL, 438.0 μmol) was added to the mixture within 1 h. Stirring was continued at 50° C. overnight. For work up, the mixture was cooled to room temperature and aqueous NaHCO$_3$ solution was added. The aqueous layer was extracted with EA several times. The combined organic layers were dried over Na$_2$SO$_4$ and after filtration evaporated in vacuo. The remaining residue was purified by flash chromatography (eluent: heptane/EA) to give the title compound. MS (m/z): 466.3 [M+Na$^+$].

Step F Synthesis of (S)-1-((S)-1-(3-chloro-5-fluoro-2-(hydroxymethyl)phenyl)ethyl)-4-(difluoromethoxy)pyrrolidin-2-one (S)-1-((S)-1-(3-Chloro-5-fluoro-2-((4-methoxyphenoxy)methyl)phenyl)ethyl)-4-(difluoromethoxy)pyrrolidin-2-one (12 mg, 27.0 μmol) was reacted with ammonium cerium(IV) nitrate (37.0 mg, 67.6 μmol) according to the synthesis of (S)-2-(3-(1-(3-chloro-5-fluoro-2-(hydroxymethyl)phenyl)ethyl)-2,5-dioxoimidazolidin-1-yl)acetamide to give the title compound. MS (m/z): 360.4 [M+Na$^+$].

Step G. Synthesis of (S)-1-((S)-1-(3-chloro-2-(chloromethyl)-5-fluorophenyl)ethyl)-4-(difluoromethoxy)pyrrolidin-2-one (S)-1-((S)-1-(3-Chloro-5-fluoro-2-(hydroxymethyl)phenyl)ethyl)-4-(difluoromethoxy) pyrrolidin-2-one (8.3 mg, 25 μmol) was reacted with SOCl$_2$ (8.91 μL, 14.62 mg, 123 μmol) according to the synthesis of (S)-2-(3-(1-(3-chloro-2-(chloromethyl)-5-fluorophenyl)ethyl)-2,5-dioxoimidazolidin-1-yl)acetamide to give the title compound. MS (m/z): 477.1 [M+Na$^+$].

Step H Synthesis of (S)-1-((S)-1-(3-chloro-5-fluoro-2-((2-methyl-4-(1-methyl-1H-1,2,4-triazol-5-yl)quinolin-8-yloxy)methyl)phenyl)ethyl)-4-(difluoromethoxy)pyrrolidin-2-one (S)-1-((S)-1-(3-Chloro-2-(chloromethyl)-5-fluorophenyl)ethyl)-4-(difluoromethoxy) pyrrolidin-2-one (20.0 mg, 65 μmol) was reacted with 2-methyl-4-(1-methyl-1H-1,2,4-triazol-5-yl)quinolin-8-ol (15.7 mg, 65 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 560.0 [M+H$^+$].

Example 7: Preparation of Compound No. 7

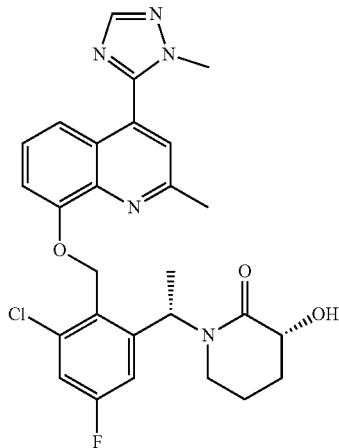 [SMILES: Cc1cc(-c2ncnn2C)c2cccc(OCc3c(Cl)cc(F)cc3[C@H](C)N3CCC[C@@H](O)C3=O)c2n1]

(R)-1-((S)-1-(3-chloro-5-fluoro-2-((2-methyl-4-(1-methyl-1H-1,2,4-triazol-5-yl)quinolin-8-yloxy)methyl)phenyl)ethyl)-3-hydroxypiperidin-2-one Step A. Synthesis of (R)-tert-butyl 2-(tert-butyldimethylsilyloxy)-5-hydroxypentanoate (R)-1-tert-Butyl 5-methyl 2-(tert-butyldimethylsilyloxy) pentanedioate [Kulkarni, S. S. et al. *Organic Letters* 2014, 16, 4336-4339] (3.42 g, 10.3 mmol) was dissolved in toluene (100 mL) and the solution was cooled to −78° C. Dibutylaluminiumhydride (25% in toluene, ca. 1.5 M, 10.29 mL, 15.44 mmol) was dropped to the solution. After the addition the cooling bath was removed and stirring was continued overnight. Water was added cautiously and stirring was continued for another hour. The toluene layer was separated and dried over Na$_2$SO$_4$. After filtration and evaporation in vacuo the remaining residue was purified by flash chromatography (eluent: heptane/EA) to give the title compound.

Step B. Synthesis of (R)-tert-butyl 2-(tert-butyldimethylsilyloxy)-5-oxopentanoate (R)-tert-Butyl 2-(tert-butyldimethylsilyloxy)-5-hydroxypentanoate (435.10 mg, 1.43 mmol) was reacted with Dess-Martin-Periodinane (237 mg, 1.71 mmol) according to the synthesis of (S)-methyl 2-(tert-butyldimethylsilyloxy)-4-oxobutanoate to give the title compound.

Step C. Synthesis of (R)-tert-butyl 2-(tert-butyldimethylsilyloxy)-5-((S)-1-(3-chloro-5-fluoro-2-((4-methoxyphenoxy)methyl)phenyl)ethylamino)pentanoate (S)-1-(3-Chloro-5-fluoro-2-((4-methoxyphenoxy)methyl) phenyl)ethanamine (248.8 mg, 803.2 µmol) was reacted with (R)-tert-butyl 2-(tert-butyldimethylsilyloxy)-5-oxopentanoate (267.25 mg, 883.5 µmol) according to the synthesis of ((S)-ethyl 2-(1-(3-chloro-5-fluoro-2-((4-methoxyphenoxy)methyl)phenyl)ethylamino)acetate to give the title compound. MS (m/z): 596.5 [M+H$^+$].

Step D. Synthesis of (R)-5-((S)-1-(3-chloro-5-fluoro-2-((4-methoxyphenoxy) methyl) phenyl) ethylamino)-2-hydroxypentanoic Acid (R)-tert-Butyl 2-(tert-butyldimethylsilyloxy)-5-((S)-1-(3-chloro-5-fluoro-2-((4-methoxy-phenoxy) methyl)phenyl) ethylamino)pentanoate (400.0 mg, 671.0 µmol) was dissolved in HCl solution in dioxane (3 N, 15 mL) and stirred overnight. Evaporation of the solvent gave the title compound. MS (m/z): 426.4 [M+H$^+$].

Step E. Synthesis of (R)-1-((S)-1-(3-chloro-5-fluoro-2-((4-methoxyphenoxy) methyl) phenyl) ethyl)-3-hydroxypiperidin-2-one (R)-5-((S)-1-(3-Chloro-5-fluoro-2-((4-methoxyphenoxy) methyl)phenyl)ethylamino)-2-hydroxypentanoic acid (321.1 mg, 754.0 µmol) was reacted with HATU (573.36 mg, 1.5 mmol) and DIPEA (292.3 mg, 387.2 µL, 2.26 mmol) according to the synthesis of (S)-3-(tert-butyldimethylsilyloxy)-1-((S)-1-(3-chloro-5-fluoro-2-((4-methoxyphenoxy) methyl)phenyl) ethyl) pyrrolidin-2-one to give the title compound. MS (m/z): 430.6 [M+Na$^+$].

Step F Synthesis of (R)-1-((S)-1-(3-chloro-5-fluoro-2-(hydroxymethyl)phenyl)ethyl)-3-hydroxypiperidin-2-one (R)-1-((S)-1-(3-Chloro-5-fluoro-2-((4-methoxyphenoxy) methyl)phenyl)ethyl)-3-hydroxypiperidin-2-one (135.2 mg, 331.5 µmol) was reacted with ammonium cerium(IV) nitrate (454.3 mg, 828.7 µmol) according to the synthesis of (S)-2-(3-(1-(3-chloro-5-fluoro-2-(hydroxymethyl)phenyl) ethyl)-2,5-dioxoimidazolidin-1-yl)acetamide to give the title compound. MS (m/z): 324.4 [M+Na$^+$].

Step G. Synthesis of (R)-1-((S)-1-(3-chloro-2-(chloromethyl)-5-fluorophenyl)ethyl)-3-hydroxypiperidin-2-one (R)-1-((S)-1-(3-Chloro-5-fluoro-2-(hydroxymethyl)phenyl)ethyl)-3-hydroxypiperidin-2-one (53.3 mg, 176.6 µmol) was reacted with SOCl$_2$ (25.63 µL, 42.03 mg, 353.3 µmol) according to the synthesis of (S)-2-(3-(1-(3-chloro-2-(chloromethyl)-5-fluorophenyl)ethyl)-2,5-dioxoimidazolidin-1-yl)acetamide to give the title compound.

Step H. Synthesis of (R)-1-((S)-1-(3-chloro-5-fluoro-2-((2-methyl-4-(1-methyl-1H-1,2,4-triazol-5-yl)quinolin-8-yloxy)methyl)phenyl)ethyl)-3-hydroxypiperidin-2-one (R)-1-((S)-1-(3-Chloro-2-(chloromethyl)-5-fluorophenyl) ethyl)-3-hydroxypiperidin-2-one (28.3 mg, 88.32 µmot) was reacted with 2-methyl-4-(1-methyl-1H-1,2,4-triazol-5-yl) quinolin-8-ol (21.22 mg, 88.32 µmol) in ACN (2 mL) according to the synthesis of ((S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl) acetamide to give the title compound. MS (m/z): 524.2 [M+H$^+$].

Example 8: Preparation of Compound No. 8

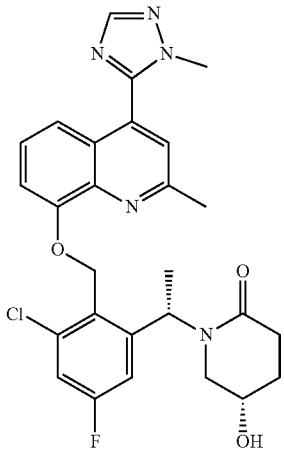 [SMILES: Cc1cc(-c2ncnn2C)c2cccc(OCc3c(Cl)cc(F)cc3[C@H](C)N3C[C@@H](O)CCC3=O)c2n1]

(S)-1-((S)-1-(3-chloro-5-fluoro-2-((2-methyl-4-(1-methyl-1H-1,2,4-triazol-5-yl)quinolin-8-yloxy)methyl)phenyl)ethyl)-5-hydroxypiperidin-2-one

Step A. Synthesis of (R)-tert-butyl 2-(tert-butyldimethylsilyloxy)-5-((S)-1-(3-chloro-5-fluoro-2-((4-methoxyphenoxy)methyl)phenyl)ethylamino)pentanoate (S)-1-(3-Chloro-5-fluoro-2-((4-methoxyphenoxy)methyl)phenyl)ethanamine (80.0 mg, 258.3 μmol) was reacted with (S)-methyl 4-(tert-butyldimethylsilyloxy)-5-oxopentanoate [Petasis, N. A. et al. *Organic Letters* 2013, 15, 1424-1427] (73.98 mg, 284.1 μmol) according to the synthesis of ((S)-ethyl 2-(1-(3-chloro-5-fluoro-2-((4-methoxyphenoxy)methyl)phenyl)ethylamino)acetate to give the title compound. MS (m/z): 554.5 [M+H$^+$].

Step B. Synthesis of (S)-4-(tert-butyldimethylsilyloxy)-5-((S)-1-(3-chloro-5-fluoro-2-((4-methoxyphenoxy)methyl)phenyl)ethylamino)pentanoic Acid (R)-tert-Butyl 2-(tert-butyldimethylsilyloxy)-5-((S)-1-(3-chloro-5-fluoro-2-((4-methoxy-phenoxy)methyl)phenyl)ethylamino)pentanoate (82.7 mg, 149 μmol) was reacted with lithium hydroxide monohydrate (15.66 mg, 373.1 μmol) according to the synthesis of (S)-2-(tert-butyldimethylsilyloxy)-4-((S)-1-(3-chloro-5-fluoro-2-((4-methoxyphenoxy)methyl)phenyl) ethylamino)butanoic acid to give the title compound. MS (m/z): 540.4 [M+H$^+$].

Step C. Synthesis of (S)-5-(tert-butyldimethylsilyloxy)-1-((S)-1-(3-chloro-5-fluoro-2-((4-methoxyphenoxy)methyl)phenyl)ethyl)piperidin-2-one (S)-4-(tert-Butyldimethylsilyloxy)-5-((S)-1-(3-chloro-5-fluoro-2-((4-methoxyphenoxy) methyl)phenyl)ethylamino) pentanoic acid (72.7 mg, 134.6 μmol) was reacted with HATU (102.3 mg, 269.2 μmol) and DIPEA (34.8 mg, 46.1 μL, 269.2 μmol) according to the synthesis of (S)-3 (tert-butyldimethylsilyloxy)-1-((S)-1-(3-chloro-5-fluoro-2-((4-methoxyphenoxy)methyl) phenyl) ethyl)pyrrolidin-2-one to give the title compound. MS (m/z): 522.4 [M+H$^+$].

Step D Synthesis of (S)-5-(tert-butyldimethylsilyloxy)-1-((S)-1-(3-chloro-5-fluoro-2-(hydroxymethyl)phenyl)ethyl)piperidin-2-one (S)-5-(tert-Butyldimethylsilyloxy)-1-((S)-1-(3-chloro-5-fluoro-2-((4-methoxyphenoxy) methyl)phenyl)ethyl)piperidin-2-one (49.1 mg, 94.0 μmol) was reacted with ammonium cerium(IV) nitrate (128.9 mg, 235.1 μmol) according to the synthesis of (S)-2-(3-(1-(3-chloro-5-fluoro-2-(hydroxymethyl)phenyl)ethyl)-2,5-dioxoimidazolidin-1-yl)acetamide to give the title compound. MS (m/z): 438.4 [M+Na$^+$].

Step E. Synthesis of (S)-1-((S)-1-(3-chloro-2-(chloromethyl)-5-fluorophenyl)ethyl)-5-hydroxypiperidin-2-one ((S)-5-(tert-Butyldimethylsilyloxy)-1-((S)-1-(3-chloro-5-fluoro-2-(hydroxymethyl)phenyl) ethyl)piperidin-2-one (21.6 mg, 52.0 μmol) was reacted with SOCl$_2$ (18.83 μL, 30.9 mg, 259.6 μmol) according to the synthesis of (S)-2-(3-(1-(3-chloro-2-(chloromethyl)-5-fluorophenyl)ethyl)-2,5-dioxoimidazolidin-1-yl)acetamide to give the title compound. MS (m/z): 320.5 [M+H$^+$].

Step F Synthesis of (S)-1-((S)-1-(3-chloro-5-fluoro-2-((2-methyl-4-(1-methyl-1H-1,2,4-triazol-5-yl)quinolin-8-yloxy)methyl)phenyl)ethyl)-5-hydroxypiperidin-2-one (S)-1-((S)-1-(3-Chloro-2-(chloromethyl)-5-fluorophenyl) ethyl)-5-hydroxypiperidin-2-one (8.3 mg, 26.0 μmol) was reacted with 2-methyl-4-(1-methyl-1H-1,2,4-triazol-5-yl)quinolin-8-ol (6.24 mg, 26.0 μmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 524.2 [M+H$^+$].

Example 9: Preparation of Compound No. 9

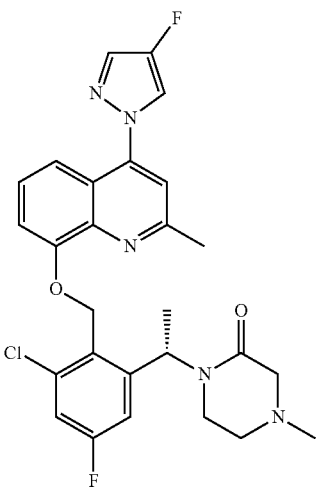 [SMILES: Cc1cc(-n2cc(F)cn2)c2cccc(OCc3c(Cl)cc(F)cc3[C@H](C)N3CCN(C)CC3=O)c2n1]

(S)-1-(1-(3-chloro-5-fluoro-2-((4-(4-fluoro-1H-pyrazol-1-yl)-2-methylquinolin-8-yloxy)methyl)phenyl)ethyl)-4-methylpiperazin-2-one

Step A. Synthesis of (S)—N¹-(1-(3-chloro-5-fluoro-2-((4-methoxyphenoxy) methyl) phenyl) ethyl)ethane-1,2-diamine (S)-tert-Butyl 2-(1-(3-chloro-5-fluoro-2-((4-methoxyphenoxy)methyl)phenyl)ethylamino) ethylcarbamate (1.17 g, 2.58 mmol) was dissolved in a mixture of methanol (5 mL) and HCl (3M in methanol, 5 mL). The solution was stirred for 2 h and then evaporated to dryness under reduced pressure. Ammonia in methanol was added and the solution evaporated to dryness under reduced pressure again. The remaining residue was purified by flash chromatography (eluent: DCM/MeOH/aqueous ammonia) to give the title compound. MS (m/z): 375.4 [M+Na⁺].

Step B Synthesis of (S)-ethyl 2-(2-(1-(3-chloro-5-fluoro-2-((4-methoxyphenoxy) methyl) phenyl)ethylamino)ethylamino)acetate (S)—N¹-(1-(3-Chloro-5-fluoro-2-((4-methoxyphenoxy)methyl)phenyl)ethyl)ethane-1,2-diamine (500 mg, 1.41 mmol) was reacted with ethylglyoxalate solution, 50% in toluene (309.0 µL, 1.56 mmol) and borane-pyridine-complex (214.7 µl, 2.12 mmol) according to the synthesis of (S)-ethyl 2-(1-(3-chloro-5-fluoro-2-((4-methoxyphenoxy)methyl)phenyl)ethylamino)acetate to give the title compound. MS (m/z): 439.6 [M+H⁺].

Step C. Synthesis of (S)-ethyl 2-(tert-butoxycarbonyl(2-(1-(3-chloro-5-fluoro-2-((4-methoxyphenoxy)methyl)phenyl)ethylamino)ethyl)amino)acetate ((S)-Ethyl 2-(2-(1-(3-chloro-5-fluoro-2-((4-methoxyphenoxy)methyl)phenyl) ethylamino) ethylamino)acetate (82.7 mg, 149.2 µmol) was dissolved in dioxane (5 mL) and sodium carbonate solution (79.1 mg, 746.4 µmol), dissolved in water (2.5 mL), was added. The suspension was cooled to 0° C. and di-tert-butylcarbonate (142.5 mg, 653.1 µmol) was added in several portions. Then, the cooling bath was removed and the mixture was stirred at room temperature for 2 hours. The dioxane was removed in vacuo and the aqueous phase was extracted with DCM (3×). The combined organic layers were dried over Na₂SO₄ and after filtration evaporated under reduced pressure. The remaining residue was purified by flash chromatography (eluent: heptane/EA) to give the title compound. MS (m/z): 561.7 [M+Na⁺].

Step D. Synthesis of (S)-2-(tert-butoxycarbonyl(2-(1-(3-chloro-5-fluoro-2-((4-methoxyphenoxy)methyl)phenyl)ethylamino)ethyl)amino)acetic Acid (S)-Ethyl 2-(tert-butoxycarbonyl(2-(1-(3-chloro-5-fluoro-2-((4-methoxyphenoxy)methyl) phenyl) ethylamino) ethyl)amino)acetate (258.0 mg, 478.6 µmol) was reacted with lithium hydroxide monohydrate (50.22 mg, 1.2 mmol) according to the synthesis of (S)-2-(tert-butyldimethylsilyloxy)-4-((S)-1-(3-chloro-5-fluoro-2-((4-methoxyphenoxy)methyl)phenyl) ethylamino)butanoic acid to give the title compound. 511.3 [M+H⁺].

Step E. Synthesis of (S)-tert-butyl 4-(1-(3-chloro-5-fluoro-2-((4-methoxyphenoxy) methyl) phenyl) ethyl)-3-oxopiperazine-1-carboxylate ((S)-2-(Tert-Butoxycarbonyl(2-(1-(3-chloro-5-fluoro-2-((4-methoxyphenoxy)methyl)phenyl) ethylamino)ethyl) amino)acetic acid (243.0 mg, 475.5 µmol) was reacted with HATU (361.6 mg, 951.1 µmol) and DIPEA (122.9 mg, 162.8 µL, 951.1 µmol) according to the synthesis of (S)-3-(tert-butyldimethylsilyloxy)-1-((S)-1-(3-chloro-5-fluoro-2-((4-methoxyphenoxy)methyl) phenyl) ethyl)pyrrolidin-2-one to give the title compound. MS (m/z): 515.5 [M+Na⁺].

Step F Synthesis of (S)-tert-butyl 4-(1-(3-chloro-5-fluoro-2-(hydroxymethyl)phenyl)ethyl)-3-oxopiperazine-1-carboxylate (S)-tert-Butyl 4-(1-(3-chloro-5-fluoro-2-((4-methoxyphenoxy)methyl)phenyl)ethyl)-3-oxopiperazine-1-carboxylate (202.0 mg, 409.7 µmol) was reacted with ammonium cerium (IV) nitrate (561.6 mg, 1.0 mmol) according to the synthesis of (S)-2-(3-(1-(3-chloro-5-fluoro-2-(hydroxymethyl)phenyl)ethyl)-2,5-dioxoimidazolidin-1-yl)acetamide to give the title compound. MS (m/z): 409.3 [M+Na⁺].

Step G. Synthesis of (S)-1-(1-(3-chloro-2-(chloromethyl)-5-fluorophenyl)ethyl)piperazin-2-one (S)-tert-Butyl 4-(1-(3-chloro-5-fluoro-2-(hydroxymethyl)phenyl)ethyl)-3-oxopiperazine-1-carboxylate (64.0 mg, 165.0 µmol) was reacted with SOCl₂ (60.0 µL, 98.4 mg, 827.0 µmol) according to the synthesis of (S)-2-(3-(1-(3-chloro-2-(chloromethyl)-5-fluorophenyl)ethyl)-2,5-dioxoimidazolidin-1-yl)acetamide to give the title compound. MS (m/z): 427.6 [M+Na⁺].

Step H. Synthesis of (S)-1-(1-(3-chloro-5-fluoro-2-((4-(4-fluoro-1H-pyrazol-1-yl)-2-methylquinolin-8-yloxy)methyl)phenyl)ethyl)piperazin-2-one (S)-1-(1-(3-Chloro-2-(chloromethyl)-5-fluorophenyl)ethyl)piperazin-2-one (50.3 mg, 165.0 µmol) was reacted with 4-(4-fluoro-1H-pyrazol-1-yl)-2-methylquinolin-8-ol (40.1 mg, 165 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 512.0 [M+H⁺].

Step I. Synthesis of (S)-1-(1-(3-chloro-5-fluoro-2-((4-(4-fluoro-1H-pyrazol-1-yl)-2-methylquinolin-8-yloxy)methyl)phenyl)ethyl)-4-methylpiperazin-2-one (S)-1-(1-(3-Chloro-5-fluoro-2-((4-(4-fluoro-1H-pyrazol-1-yl)-2-methylquinolin-8-yloxy)methyl)phenyl)ethyl)piperazin-2-one (15 mg, 29.3 µmol) was reacted with aqueous formaldehyde solution (37%, 150.5 µL, 3.96 mmol) and borane-pyridine-complex (5.9 µl, 58.6 µmol) according to the synthesis of (S)-ethyl 2-(1-(3-chloro-5-fluoro-2-((4-methoxyphenoxy)methyl)phenyl)ethylamino)acetate to give the title compound. MS (m/z): 526.2 [M+H⁺].

Example 10: Preparation of Compound No. 10

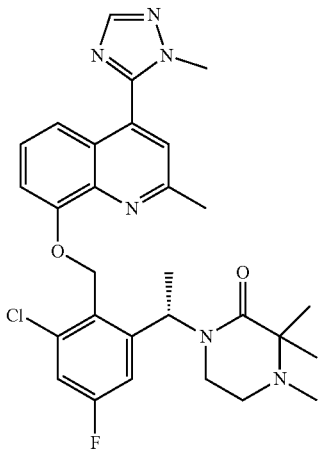 [SMILES: Cc1cc(-c2ncnn2C)c2cccc(OCc3c(Cl)cc(F)cc3[C@H](C)N3CCN(C)C(C)(C)C3=O)c2n1]

(S)-1-(1-(3-chloro-5-fluoro-2-((2-methyl-4-(1-methyl-1H-1,2,4-triazol-5-yl)quinolin-8-yloxy)methyl)phenyl)ethyl)-3,3,4-trimethylpiperazin-2-one

Step A. Synthesis of (S)-ethyl 2-(tert-butoxycarbonyl(1-(3-chloro-5-fluoro-2-((4-methoxy-phenoxy)methyl)phenyl)ethyl)amino)acetate (S)-Ethyl 2-(1-(3-chloro-5-fluoro-2-((4-methoxyphenoxy)methyl)phenyl)ethylamino)acetate (726.0 mg, 1.8 mmol) was reacted with di-tert-butyl dicarbonate (2.0 g, 9.17 mmol) according to the synthesis of (S)-ethyl 2-(tert-butoxycarbonyl(2-(1-(3-chloro-5-fluoro-2-((4-methoxyphenoxy)methyl)phenyl)ethylamino)ethyl)amino)acetate to give the title compound. MS (m/z): 518.3 [M+Na$^+$].

Step B. Synthesis of (9-tell-butyl 1-(3-chloro-5-fluoro-2-((4-methoxyphenoxy)methyl) phenyl)ethyl (2-hydroxyethyl)carbamate (S)-Ethyl 2-(tert-butoxycarbonyl(1-(3-chloro-5-fluoro-2-((4-methoxyphenoxy)methyl)phenyl) ethyl)amino)acetate (787.0 mg, 1.59 mmol) was reacted with dibutylaluminium-hydride 25% in toluene, (1.5 M, 1.59 mL, 2.38 mmol) according to the synthesis of (R)-tert-butyl 2-(tert-butyldimethylsilyloxy)-5-hydroxypentanoate to give the title compound MS (m/z): 476.5 [M+Na$^+$].

Step C. Synthesis of (S)-tert-butyl 1-(3-chloro-5-fluoro-2-((4-methoxyphenoxy) methyl) phenyl)ethyl (2-oxoethyl)carbamate (S)-tert-Butyl 1-(3-chloro-5-fluoro-2-((4-methoxyphenoxy)methyl)phenyl)ethyl(2-hydroxy-ethyl)carbamate (467.3 mg, 1.03 mmol) was reacted with Dess-Martin-Periodinane (170.7 mg, 1.23 mmol) according to the synthesis of (S)-methyl 2-(tert-butyldimethylsilyloxy)-4-oxobutanoate to give the title compound.

Step D. Synthesis of (S)-methyl 2-(2-(tert-butoxy-carbonyl(1-(3-chloro-5-fluoro-2-((4-methoxyphenoxy)methyl)phenyl)ethyl)amino)ethylamino)-2-methylpropanoate (S)-tert-Butyl 1-(3-chloro-5-fluoro-2-((4-methoxyphenoxy)methyl)phenyl)ethyl(2-oxoethyl)carbamate (148.3 mg, 328.7 μmol) was reacted with methyl 2-amino-2-methylpropanoate hydrochloride (55.5 mg, 361.6 μmol) and borane-pyridine complex (49.8 μL, 493.1 μmol) according to the synthesis of (S)-ethyl 2-(1-(3-chloro-5-fluoro-2-((4-methoxyphenoxy)methyl)phenyl)ethylamino)acetate to give the title compound. MS (m/z): 551.2 [M–H$^+$].

Step E. Synthesis of (S)-methyl 2-(2-(1-(3-chloro-5-fluoro-2-((4-methoxyphenoxy)methyl)phenyl)ethylamino)ethylamino)-2-methylpropanoate (S)-Methyl 2-(2-(tert-butoxycarbonyl(1-(3-chloro-5-fluoro-2-((4-methoxyphenoxy)methyl) phenyl) ethyl)amino)ethylamino)-2-methylpropanoate (205.8 mg, 372.1 μmol) was dissolved in dichloromethane (3 mL) and trifluoroacetic acid (0.75 mL) and the resulting mixture was stirred for 1 h. Then the solution was cooled to 0° C. and saturated aqueous sodium carbonate solution was added cautiously until gas evolution ceased and the pH value was adjusted to 9. The mixture was diluted with DCM and the aqueous layer was extracted with DCM (3×). The combined organic layers were dried over Na$_2$SO$_4$ and after filtration evaporated in vacuo to give the title compound.

Step F. Synthesis of (S)-2-(2-(1-(3-chloro-5-fluoro-2-((4-methoxyphenoxy) methyl) phenyl) ethyl-amino)ethylamino)-2-methylpropanoic Acid (S)-Methyl 2-(2-(1-(3-chloro-5-fluoro-2-((4-methoxyphenoxy)methyl)phenyl)ethylamino)ethylamino)-2-methylpropanoate (149.2 mg, 329.4 μmol) was reacted with lithium hydroxide monohydrate (34.5 mg, 823.5 μmol) according to the synthesis of (S)-2-(tert-butyldimethylsilyloxy)-4-((S)-1-(3-chloro-5-fluoro-2-((4-methoxy-phenoxy) methyl)phenyl)ethylamino)butanoic acid to give the title compound. MS (m/z): 453.4 [M+H$^+$].

Step G. Synthesis of (S)-1-(1-(3-chloro-5-fluoro-2-((4-methoxyphenoxy)methyl) phenyl) ethyl)-3,3-dimethylpiperazin-2-one (S)-2-(2-(1-(3-Chloro-5-fluoro-2-((4-methoxyphenoxy)methyl)phenyl)ethylamino) ethylamino)-2-methylpropanoic acid (129.3 mg, 294.6 μmol) was reacted with HATU (224.0 mg, 589.1 μmol) and DIPEA (76.1 mg, 100.8 μL, 589.1 μmol) according to the synthesis of (S)-3-(tert-butyldimethylsilyloxy)-1-((S)-1-(3-chloro-5-fluoro-2-((4-methoxyphenoxy)methyl) phenyl) ethyl)pyrrolidin-2-one to give the title compound. MS (m/z): 443.5 [M+Na$^+$].

Step H. Synthesis of (S)-1-(1-(3-chloro-5-fluoro-2-(hydroxymethyl)phenyl)ethyl)-3,3-dimethylpiperazin-2-one (S)-1-(1-(3-Chloro-5-fluoro-2-((4-methoxyphenoxy)methyl)phenyl)ethyl)-3,3-dimethylpiperazin-2-one (97.3 mg, 231.1 μmol) was reacted with ammonium cerium(IV) nitrate (316.8 mg, 577.9 μmol) according to the synthesis of (S)-2-(3-(1-(3-chloro-5-fluoro-2-(hydroxymethyl)phenyl)ethyl)-2,5-dioxoimidazolidin-1-yl)acetamide to give the title compound. MS (m/z): 337.3 [M+Na$^+$].

Step I. Synthesis of (S)-1-(1-(3-chloro-2-(chloromethyl)-5-fluorophenyl)ethyl)-3,3-dimethylpiperazin-2-one (S)-1-(1-(3-Chloro-5-fluoro-2-(hydroxymethyl)phenyl)ethyl)-3,3-dimethylpiperazin-2-one (31.8 mg, 101.0 μmol)

was reacted with SOCl$_2$ (22.0 µL, 36.0 mg, 303.0 µmol) according to the synthesis of (S)-2-(3-(1-(3-chloro-2-(chloromethyl)-5-fluorophenyl)ethyl)-2,5-dioxoimidazolidin-1-yl)acetamide to give the title compound.

Step J. Synthesis of (S)-1-(1-(3-chloro-5-fluoro-2-((2-methyl-4-(1-methyl-1H-1,2,4-triazol-5-yl)quinolin-8-yloxy)methyl)phenyl)ethyl)-3,3-dimethylpiperazin-2-one (S)-1-(1-(3-Chloro-2-(chloromethyl)-5-fluorophenyl)ethyl)-3,3-dimethylpiperazin-2-one (16.8 mg, 50.5 µmol) was reacted with 2-methyl-4-(1-methyl-1H-1,2,4-triazol-5-yl)quinolin-8-ol (12.13 mg, 50.5 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 537.4 [M+H$^+$].

Step K. (S)-1-(1-(3-chloro-5-fluoro-2-((2-methyl-4-(1-methyl-1H-1,2,4-triazol-5-yl)quinolin-8-yloxy)methyl)phenyl)ethyl)-3,3,4-trimethylpiperazin-2-one (S)-1-(1-(3-Chloro-5-fluoro-2-((2-methyl-4-(1-methyl-1H-1,2,4-triazol-5-yl)quinolin-8-yloxy)methyl)phenyl)ethyl)-3,3-dimethylpiperazin-2-one (3.7 mg, 6.9 µmol) was reacted with aqueous formaldehyde solution (37%, 35.4 µL, 931.0 µmol) and borane-pyridine-complex (1.4 µl, 13.8 µmol) according to the synthesis of (S)-ethyl 2-(1-(3-chloro-5-fluoro-2-((4-methoxyphenoxy)methyl)phenyl)ethylamino)acetate to give the title compound. MS (m/z): 551.1 [M+H$^+$].

Example 11: Preparation of Compound No. 11

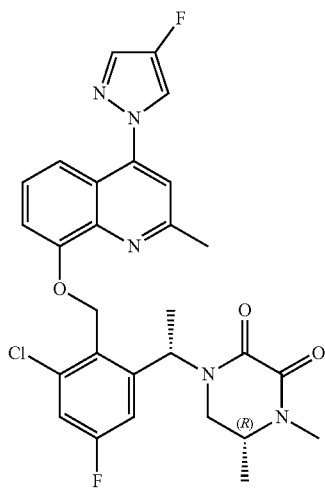

(R)-1-((S)-1-(3-chloro-5-fluoro-2-((4-(4-fluoro-1H-pyrazol-1-yl)-2-methylquinolin-8-yloxy)methyl)phenyl)ethyl)-4,5-dimethylpiperazine-2,3-dione Step A. Synthesis of Ethyl 2-(((R)-2-(tert-butoxycarbonyl(methyl)amino)propyl)((S)-1-(3-chloro-5-fluoro-2-((4-methoxyphenoxy)methyl)phenyl)ethyl)amino)acetate (S)-tert-Butyl 1-(3-chloro-5-fluoro-2-((4-methoxyphenoxy)methyl)phenyl)ethyl(2-oxoethyl) carbamate (74.0 mg, 130.5 µmol) was reacted with (R)-tert-butyl methyl(1-oxopropan-2-yl)carbamate (55.5 mg, 361.6 µmol) and borane-pyridine complex (49.8 µL, 493.1 µmmol) according to the synthesis of (S)-ethyl 2-(1-(3-chloro-5-fluoro-2-((4-methoxyphenoxy) methyl) phenyl)ethylamino)acetate to give the title compound. MS (m/z): 589.6 [M+Na$^+$].

Step B. Synthesis of 2-(((R)-2-(tert-butoxycarbonyl(methyl)amino)propyl)((S)-1-(3-chloro-5-fluoro-2-((4-methoxyphenoxy)methyl)phenyl)ethyl)amino) acetic Acid Ethyl 2-(((R)-2-(tert-butoxycarbonyl(methyl)amino)propyl)((S)-1-(3-chloro-5-fluoro-2-((4-methoxyphenoxy)methyl)phenyl)ethyl)amino)acetate (74.0 mg, 130.5 µmol) was reacted with lithium hydroxide monohydrate (13.7 mg, 326.2 µmol) according to the synthesis of (S)-2-(tert-butyldimethylsilyloxy)-4-((S)-1-(3-chloro-5-fluoro-2-((4-methoxyphenoxy)methyl)phenyl) ethylamino)butanoic acid to give the title compound. MS (m/z): 537.4 [M-W].

Step C. Synthesis of 2-(((S)-1-(3-chloro-5-fluoro-2-((4-methoxyphenoxy)methyl) phenyl) ethyl)((R)-2-(methylamino)propyl)amino)acetic Acid 2-(((R)-2-(tert-Butoxycarbonyl(methyl)amino)propyl)((S)-1-(3-chloro-5-fluoro-2-((4-methoxyphenoxy)methyl)phenyl)ethyl)amino)acetic acid (70.3 mg, 130.53 µmol) was treated in dichloromethane (1 mL) and trifluoroacetic acid (0.25 mL) according to the synthesis of (S)-methyl 2-(2-(1-(3-chloro-5-fluoro-2-((4-methoxyphenoxy)methyl)phenyl) ethylamino) ethylamino)-2-methylpropanoate to give the title compound. MS (m/z): 439.6 [M+H$^+$].

Step D. Synthesis of (R)-4-((S)-1-(3-chloro-5-fluoro-2-((4-methoxyphenoxy)methyl)phenyl) ethyl)-1,6-dimethylpiperazin-2-one 2-(((S)-1-(3-Chloro-5-fluoro-2-((4-methoxyphenoxy) methyl)phenyl)ethyl)((R)-2-(methylamino)propyl)amino) acetic acid (57.2 mg, 130.3 µmol) was reacted with HATU (99.1 mg, 260.6 µmol) and DIPEA (33.7 mg, 44.6 µL, 260.6 µmol) according to the synthesis of (S)-3-(tert-butyldimethylsilyloxy)-1-((S)-1-(3-chloro-5-fluoro-2-((4-methoxyphenoxy)methyl)phenyl)ethyl) pyrrolidin-2-one to give the title compound. MS (m/z): 421.6 [M+H$^+$].

Step E. Synthesis of (R)-1-((S)-1-(3-chloro-5-fluoro-2-(hydroxymethyl)phenyl)ethyl)-4,5-dimethylpiperazine-2,3-dione (R)-4-((S)-1-(3-Chloro-5-fluoro-2-((4-methoxyphenoxy) methyl)phenyl)ethyl)-1,6-dimethylpiperazin-2-one (46.5 mg, 110.5 µmol) was reacted with ammonium cerium(IV) nitrate (151.4 mg, 276.2 µmol) according to the synthesis of (S)-2-(3-(1-(3-chloro-5-fluoro-2-(hydroxymethyl)phenyl) ethyl)-2,5-dioxoimidazolidin-1-yl)acetamide to give the title compound. MS (m/z): 329.5 [M+H$^+$].

Step F. Synthesis of (R)-1-((S)-1-(3-chloro-2-(chloromethyl)-5-fluorophenyl)ethyl)-4,5-dimethylpiperazine-2,3-dione (R)-1-((S)-1-(3-Chloro-5-fluoro-2-(hydroxymethyl)phenyl)ethyl)-4,5-dimethylpiperazine-2,3-dione (17.0 mg, 52.0 µmol) was reacted with SOCl$_2$ (18.8 µL, 30.8 mg, 259.0 µmol) according to the synthesis of (S)-2-(3-(1-(3-chloro- 2-(chloromethyl)-5-fluorophenyl)ethyl)-2,5-dioxoimidazolidin-1-yl)acetamide to give the title compound. MS (m/z): 347.3 [M+H⁺].

Step G. Synthesis of (R)-1-((S)-1-(3-chloro-5-fluoro-2-((4-(4-fluoro-1H-pyrazol-1-yl)-2-methylquinolin-8-yloxy)methyl)phenyl)ethyl)-4,5-dimethylpiperazine-2,3-dione (R)-1-((S)-1-(3-Chloro-2-(chloromethyl)-5-fluorophenyl) ethyl)-4,5-dimethylpiperazine-2,3-dione (17.7 mg, 51.0 µmol) was reacted with 4-(4-fluoro-1H-pyrazol-1-yl)-2-methylquinolin-8-ol (12.4 mg, 51.0 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 554.1 [M+H⁺].

Example 12: Preparation of Compound No. 12

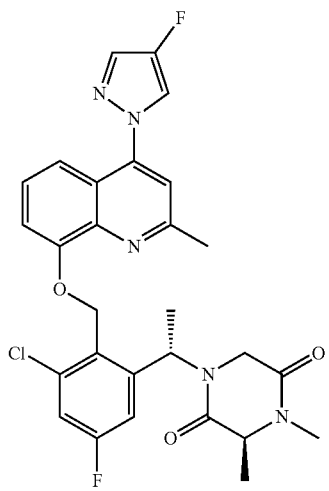 [SMILES: Cc1cc(-n2cc(F)cn2)c2cccc(OCc3c(Cl)cc(F)cc3[C@H](C)N3CC(=O)N(C)[C@@H](C)C3=O)c2n1]

(S)-1-((S)-1-(3-chloro-5-fluoro-2-((4-(4-fluoro-1H-pyrazol-1-yl)-2-methylquinolin-8-yloxy)methyl) phenyl)ethyl)-3,4-dimethylpiperazine-2,5-dione Step A. Synthesis of (S)-2-(tert-butoxycarbonyl(1-(3-chloro-5-fluoro-2-((4-methoxyphenoxy) methyl) phenyl)ethyl)amino)acetic Acid (S)-Ethyl 2-(tert-butoxycarbonyl(1-(3-chloro-5-fluoro-2-((4-methoxyphenoxy)methyl)phenyl) ethyl)amino)acetate (74.0 mg, 130.5 µmol) was reacted with lithium hydroxide monohydrate (13.7 mg, 326.2 µmol) according to the synthesis of (S)-2-(tert-butyldimethylsilyloxy)-4-((S)-1-(3-chloro-5-fluoro-2-((4-methoxyphenoxy)methyl)phenyl)ethylamino)butanoic acid to give the title compound. MS (m/z): 468.4 [M+H⁺].

Step B. Synthesis of (S)-methyl 2-(2-(tert-butoxycarbonyl((S)-1-(3-chloro-5-fluoro-2-((4-methoxyphenoxy)methyl)phenyl)ethyl)amino)-N-methylacetamido)propanoate (S)-2-(tert-Butoxycarbonyl(1-(3-chloro-5-fluoro-2-((4-methoxyphenoxy)methyl)phenyl) ethyl)amino)acetic acid (133.0, 284.2 µmol) and methyl(2S)-2-(methylamino)propanoate hydrochloride (50.2 mg, 326.9 µmol) were dissolved in DMF (5 mL) and the solution was cooled to 0° C. PyBOP (192.7 mg, 369.5 µmol) and DIPEA (84.1 µL, 483.2 µmol) were subsequently added. After stirring overnight at RT, the reaction mixture was concentrated in vacuo. The remaining residue was purified by flash chromatography (eluent: heptane/EA) to give the title compound. MS (m/z): 589.6 [M+Na⁺].

Step C. Synthesis of (S)-methyl 2-(2-((S)-1-(3-chloro-5-fluoro-2-((4-methoxyphenoxy) methyl) phenyl)ethylamino)-N-methylacetamido)propanoate (S)-Methyl 2-(2-(tert-butoxycarbonyl((S)-1-(3-chloro-5-fluoro-2-((4-methoxyphenoxy) methyl)phenyl)ethyl) amino)-N-methylacetamido)propanoate (135 mg, 238.0 µmol) was reacted in DCM (1 mL) with trifluoroacetic acid (0.25 mL) according to the synthesis of (S)-methyl 2-(2-(1-(3-chloro-5-fluoro-2-((4-methoxyphenoxy)methyl)phenyl) ethylamino)ethylamino)-2-methylpropanoate to give the title compound. MS (m/z): 467.5 [M+H⁺].

Step D. Synthesis of (S)-2-(2-((S)-1-(3-chloro-5-fluoro-2-((4-methoxyphenoxy)methyl) phenyl)ethylamino)-N-methylacetamido)propanoic Acid (S)-Methyl 2-(2-((S)-1-(3-chloro-5-fluoro-2-((4-methoxyphenoxy)methyl)phenyl) ethylamino)-N-methylacetamido)propanoate (109.0 mg, 233.4 µmol) was reacted with lithium hydroxide monohydrate (24.5 mg, 583.6.2 µmol) according to the synthesis of (S)-2-(tert-butyldimethylsilyloxy)-4-((S)-1-(3-chloro-5-fluoro-2-((4-methoxyphenoxy)methyl)phenyl) ethylamino)butanoic acid to give the title compound. MS (m/z): 451.0 [M–H⁺].

Step E. Synthesis of (S)-1-((S)-1-(3-chloro-5-fluoro-2-((4-methoxyphenoxy)methyl)phenyl) ethyl)-3,4-dimethylpiperazine-2,5-dione (S)-2-(2-((S)-1-(3-Chloro-5-fluoro-2-((4-methoxyphenoxy)methyl)phenyl)ethylamino)-N-methylacetamido)propanoic acid (105.8 mg, 233.6 µmol) was reacted with HATU (177.7 mg, 467.3 µmol) and DIPEA (60.4 mg, 80.0 µL, 467.3 µmol) according to the synthesis of (S)-3-(tert-butyldimethylsilyloxy)-1-((S)-1-(3-chloro-5-fluoro-2-((4-methoxyphenoxy)methyl)phenyl)ethyl) pyrrolidin-2-one to give the title compound. MS (m/z): 435.1 [M+H⁺].

Step F. Synthesis of (S)-1-((S)-1-(3-chloro-5-fluoro-2-(hydroxymethyl)phenyl)ethyl)-3,4-dimethylpiperazine-2,5-dione (S)-1-((S)-1-(3-Chloro-5-fluoro-2-((4-methoxyphenoxy) methyl)phenyl)ethyl)-3,4-dimethylpiperazine-2,5-dione (103.0 mg, 236.8 µmol) was reacted with ammonium cerium (IV) nitrate (324.6 mg, 592.1 µmol) according to the synthesis of (S)-2-(3-(1-(3-chloro-5-fluoro-2-(hydroxymethyl) phenyl)ethyl)-2,5-dioxoimidazolidin-1-yl)acetamide to give the title compound. MS (m/z): 351.4 [M+Na⁺].

Step G. Synthesis of (S)-1-((S)-1-(3-chloro-2-(chloromethyl)-5-fluorophenyl)ethyl)-3,4-dimethylpiperazine-2,5-dione (S)-1-((S)-1-(3-Chloro-5-fluoro-2-(hydroxymethyl)phenyl)ethyl)-3,4-dimethylpiperazine-2,5-dione (50.0 mg, 152.0 µmol) was reacted with SOCl$_2$ (55.2 µL, 90.5 mg, 760.4 µmol) according to the synthesis of (S)-2-(3-(1-(3-chloro-2-(chloromethyl)-5-fluorophenyl)ethyl)-2,5-dioxo-imidazolidin-1-yl)acetamide to give the title compound. MS (m/z): 347.4 [M+H$^+$].

Step H. Synthesis of (S)-1-((S)-1-(3-chloro-5-fluoro-2-((4-(4-fluoro-1H-pyrazol-1-yl)-2-methylquinolin-8-yloxy)methyl)phenyl)ethyl)-3,4-dimethylpiperazine-2,5-dione (S)-1-((S)-1-(3-Chloro-2-(chloromethyl)-5-fluorophenyl)ethyl)-3,4-dimethylpiperazine-2,5-dione (30.0 mg, 86.4 µmol) was reacted with 4-(4-fluoro-1H-pyrazol-1-yl)-2-methylquinolin-8-ol (21.0 mg, 86.4 µmol) according to the synthesis of (S)-2-(3-(1-(3-chloro-5-fluoro-2-((4-(4-fluoro-1H-pyrazol-1-yl)-2-methylquinolin-8-yloxy)methyl)phenyl)ethyl)-2,5-dioxoimidazolidin-1-yl)acetamide to give the title compound. MS (m/z): 554.2 [M+H$^+$].

Example 13: Compounds Nos. 13 to 107

The compounds Nos. 13 to 107 shown in the following Table 1 are further representative examples of compounds according to general formula (I) of the present invention. These compounds have been synthesized using the methods described above, together with synthetic methods disclosed in the references cited herein or known in the art of synthetic organic chemistry, and variations thereon as appreciated by those skilled in the art. Each of the references cited herein in relation to the routes of synthesis described in Examples 1 to 12 is hereby incorporated by reference in its entirety in the present specification. In any event, those skilled in the art of organic synthesis will recognize the starting materials and reaction conditions including variations to produce the compounds.

TABLE 1

Example Compounds Nos. 13 to 107

| Cpd No. | Structure | Mass[#] |
|---|---|---|
| 13. | | 497.5 |
| 14. | 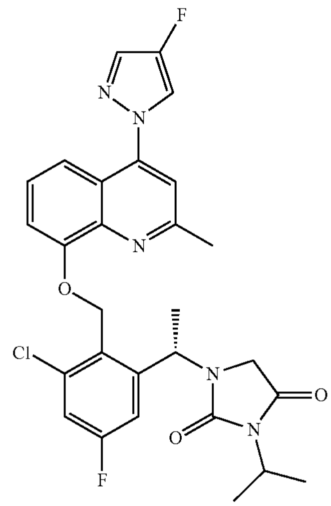 [SMILES: Cc1cc(-n2cc(F)cn2)c2cccc(OCc3c(Cl)cc(F)cc3[C@H](C)N3CC(=O)N(C(C)C)C3=O)c2n1] | 554.6 |
| 15. | 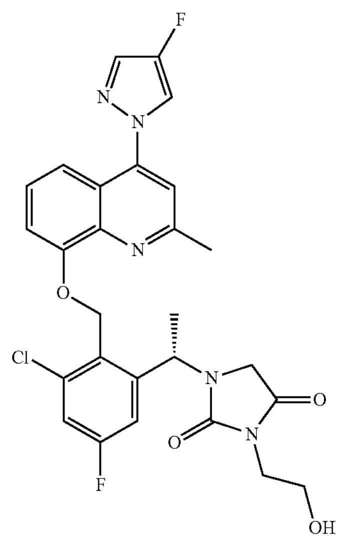 [SMILES: Cc1cc(-n2cc(F)cn2)c2cccc(OCc3c(Cl)cc(F)cc3[C@H](C)N3CC(=O)N(CCO)C3=O)c2n1] | 556.1 |
| 16. | 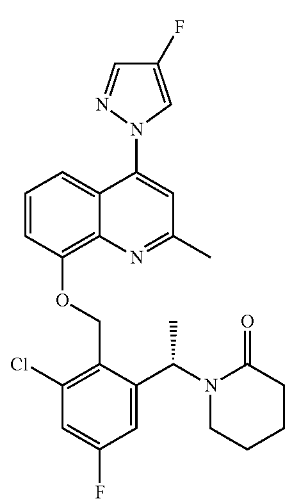 [SMILES: Cc1cc(-n2cc(F)cn2)c2cccc(OCc3c(Cl)cc(F)cc3[C@H](C)N3CCCCC3=O)c2n1] | 511.5 |

TABLE 1-continued

Example Compounds Nos. 13 to 107

| Cpd No. | Structure | Mass# |
|---|---|---|
| 17. | 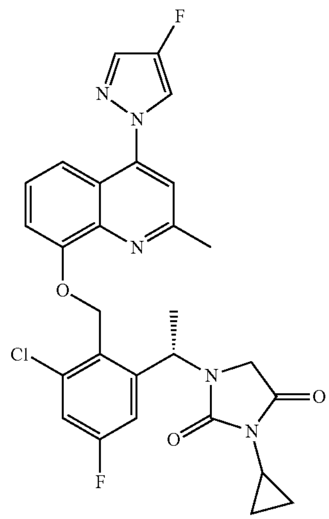 [SMILES: Cc1cc(-n2cc(F)cn2)c2cccc(OCc3c(Cl)cc(F)cc3[C@H](C)N3CC(=O)N(C4CC4)C3=O)c2n1] | 552.2 |
| 18. | 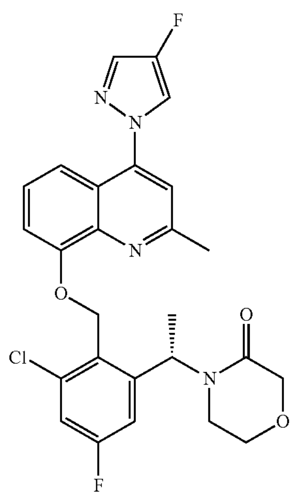 [SMILES: Cc1cc(-n2cc(F)cn2)c2cccc(OCc3c(Cl)cc(F)cc3[C@H](C)N3CCOCC3=O)c2n1] | 513.1 |
| 19. | 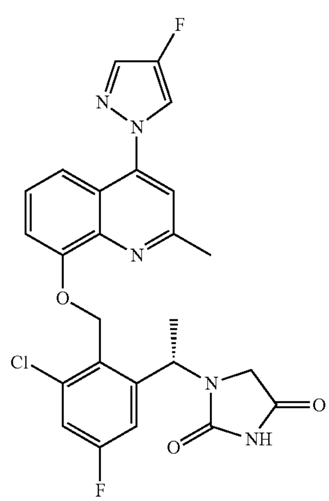 [SMILES: Cc1cc(-n2cc(F)cn2)c2cccc(OCc3c(Cl)cc(F)cc3[C@H](C)N3CC(=O)NC3=O)c2n1] | 512.1 |
| 20. | 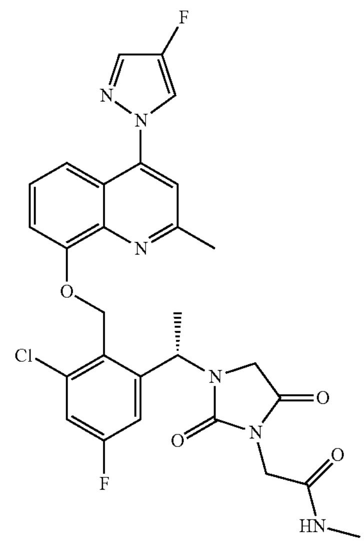 [SMILES: CNC(=O)CN1C(=O)CN([C@@H](C)c2cc(F)cc(Cl)c2COc2cccc3c(-n4cc(F)cn4)cc(C)nc23)C1=O] | 583.2 |
| 21. | 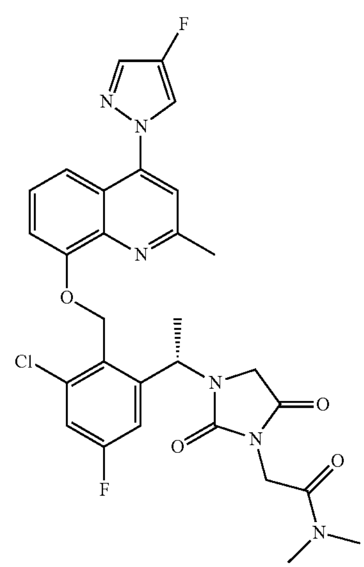 [SMILES: Cc1cc(-n2cc(F)cn2)c2cccc(OCc3c(Cl)cc(F)cc3[C@H](C)N3CC(=O)N(CC(=O)N(C)C)C3=O)c2n1] | 597.2 |

TABLE 1-continued

Example Compounds Nos. 13 to 107

| Cpd No. | Structure | Mass# |
|---|---|---|
| 22. | 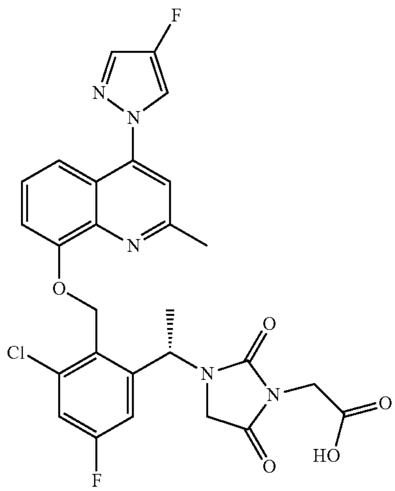 [SMILES: Cc1cc(-n2cc(F)cn2)c2cccc(OCc3c(Cl)cc(F)cc3[C@H](C)N3CC(=O)N(CC(=O)O)C3=O)c2n1] | 570.1 |
| 23. | 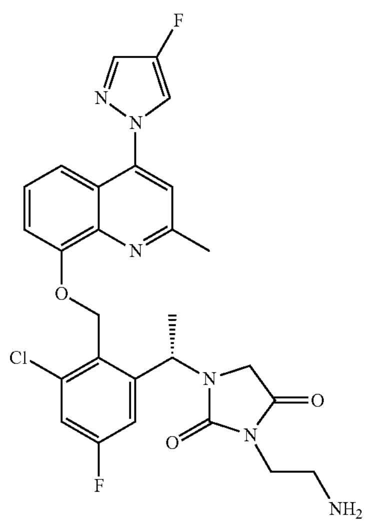 [SMILES: Cc1cc(-n2cc(F)cn2)c2cccc(OCc3c(Cl)cc(F)cc3[C@H](C)N3CC(=O)N(CCN)C3=O)c2n1] | 555.1 |
| 24. | 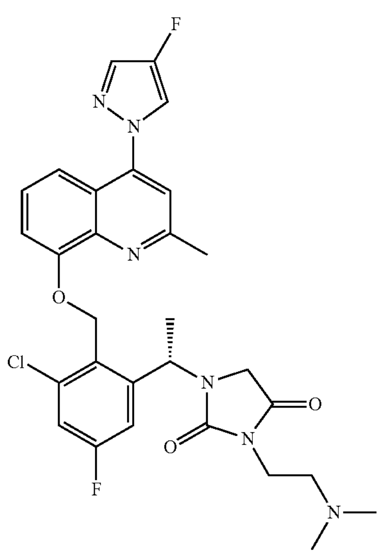 [SMILES: Cc1cc(-n2cc(F)cn2)c2cccc(OCc3c(Cl)cc(F)cc3[C@H](C)N3CC(=O)N(CCN(C)C)C3=O)c2n1] | 583.2 |
| 25. | | 526.1 |
| 26. | | 508.0 |
| 27. | | 494.4 |

TABLE 1-continued

Example Compounds Nos. 13 to 107

| Cpd No. | Structure | Mass# |
|---|---|---|
| 28. | 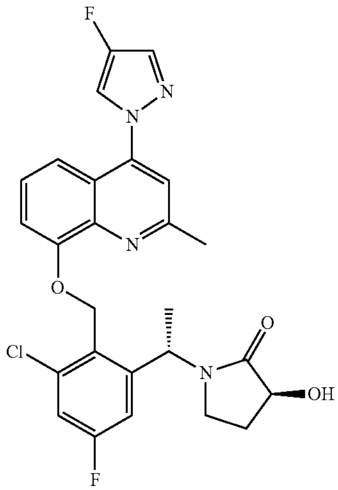 [SMILES: Cc1cc(-n2cc(F)cn2)c2cccc(OCc3c(Cl)cc(F)cc3[C@H](C)N3CC[C@H](O)C3=O)c2n1] | 513.0 |
| 29. | Diastereomer A | 554.2 |
| 30. | Diastereomer A | 566.1 |
| 31. | Diastereomer B | 566.2 |
| 32. | Diastereomer A | 527.3 |

TABLE 1-continued
Example Compounds Nos. 13 to 107
| Cpd No. | Structure | Mass# |
|---|---|---|
| 33. | 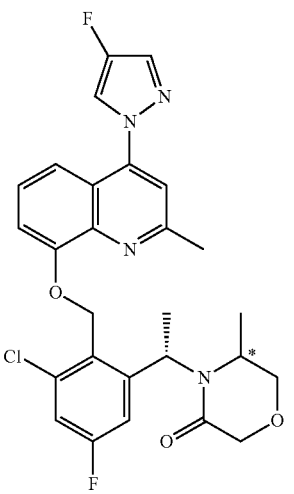 Diastereomer B | 527.3 |
| 34. | 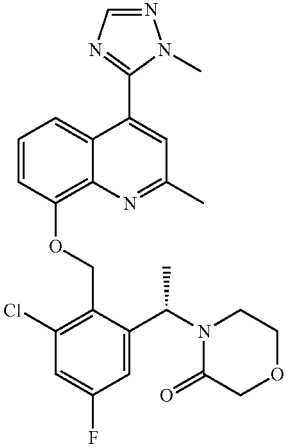 [SMILES: Cc1cc(-c2ncnn2C)c2cccc(OCc3c(Cl)cc(F)cc3[C@H](C)N3CCOCC3=O)c2n1] | 511.2 |
| 35. | 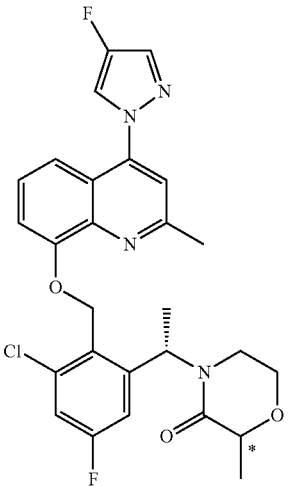 Diastereomer A | 528.1 |
| 36. | 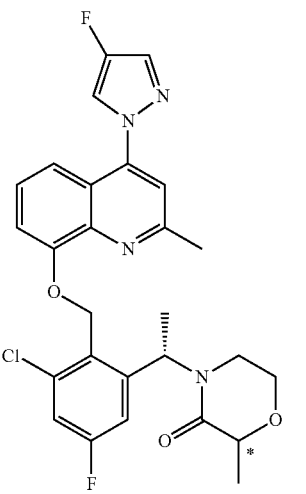 Diastereomer B | 528.1 |
| 37. | 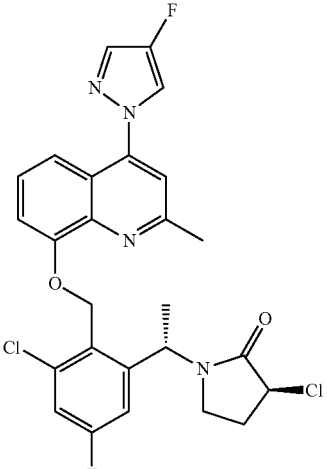 | 531.0 |
| 38. | 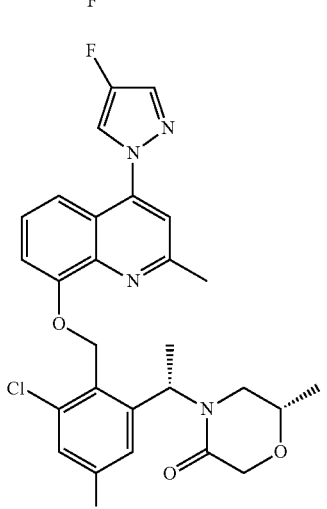 | 527.0 |

TABLE 1-continued

Example Compounds Nos. 13 to 107

| Cpd No. | Structure | Mass# |
|---|---|---|
| 39. | 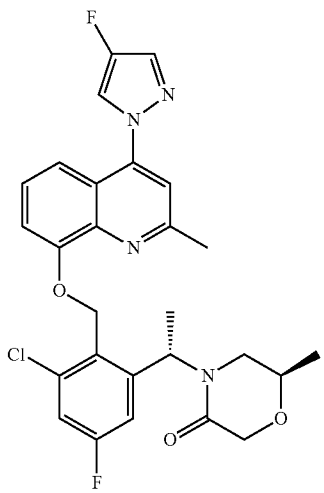 [SMILES: Cc1cc(-n2cc(F)cn2)c2cccc(OCc3c(Cl)cc(F)cc3[C@H](C)N3C[C@@H](C)OCC3=O)c2n1] | 527.9 |
| 40. | 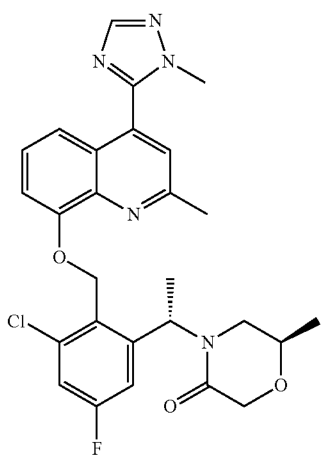 [SMILES: Cc1cc(-c2ncnn2C)c2cccc(OCc3c(Cl)cc(F)cc3[C@H](C)N3C[C@@H](C)OCC3=O)c2n1] | 524.9 |
| 41. | 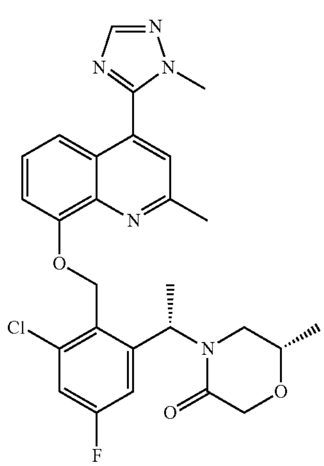 [SMILES: Cc1cc(-c2ncnn2C)c2cccc(OCc3c(Cl)cc(F)cc3[C@H](C)N3C[C@H](C)OCC3=O)c2n1] | 525.2 |
| 42. | | 513.3 |
| 43. | | 510.2 |
| 44. | | 528.1 |

TABLE 1-continued

Example Compounds Nos. 13 to 107

| Cpd No. | Structure | Mass# |
|---|---|---|
| 45. | 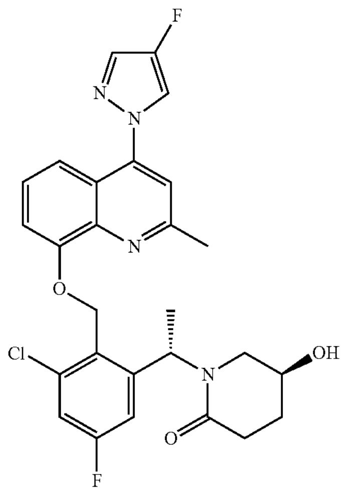 [SMILES: Cc1cc(-n2cc(F)cn2)c2cccc(OCc3c(Cl)cc(F)cc3[C@H](C)N3C[C@@H](O)CCC3=O)c2n1] | 527.2 |
| 46. | 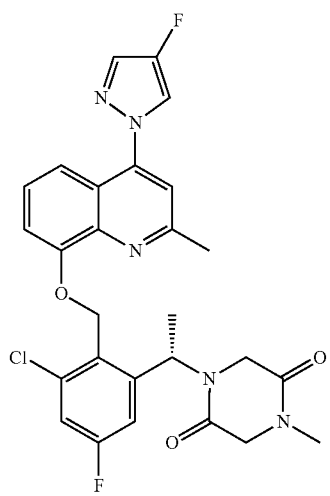 [SMILES: Cc1cc(-n2cc(F)cn2)c2cccc(OCc3c(Cl)cc(F)cc3[C@H](C)N3CC(=O)N(C)CC3=O)c2n1] | 540.1 |
| 47. | 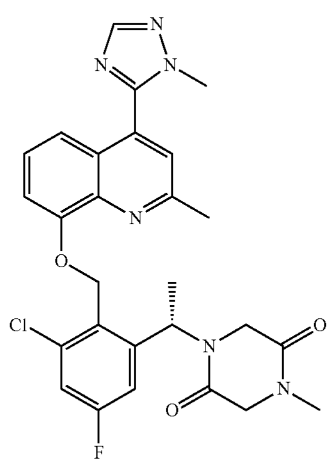 [SMILES: Cc1cc(-c2ncnn2C)c2cccc(OCc3c(Cl)cc(F)cc3[C@H](C)N3CC(=O)N(C)CC3=O)c2n1] | 537.2 |
| 48. | Diastereomer A | 524.4 |
| 49. | Diastereomer B | 524.9 |
| 50. | | 526.1 |

TABLE 1-continued

Example Compounds Nos. 13 to 107

| Cpd No. | Structure | Mass# |
|---|---|---|
| 51. | (Diastereomer A) | 529.0 |
| 52. | (Diastereomer B) | 529.0 |
| 53. | (Diastereomer A) | 551.9 |
| 54. | (Diastereomer B) | 552.0 |
| 55. | (Diastereomer A) | 563.9 |
| 56. | (Diastereomer B) | 563.9 |

TABLE 1-continued

Example Compounds Nos. 13 to 107

| Cpd No. | Structure | Mass# |
|---|---|---|
| 57. | 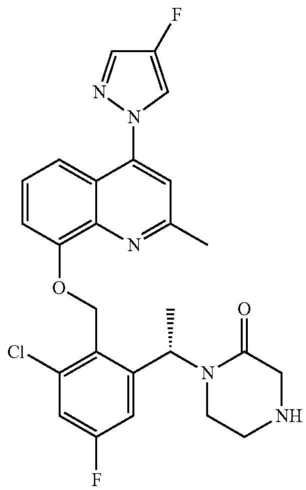 [SMILES: Cc1cc(-n2cc(F)cn2)c2cccc(OCc3c(Cl)cc(F)cc3[C@H](C)N3CCNCC3=O)c2n1] | 512.0 |
| 58. | Diastereomer A | 511.4 |
| 59. | Diastereomer B | 511.1 |
| 60. | Diastereomer A | 508.0 |
| 61. | Diastereomer B | 508.0 |
| 62. | 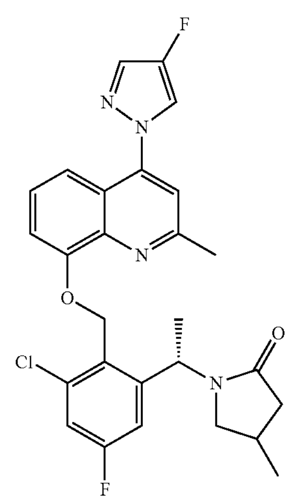 [SMILES: Cc1cc(-n2cc(F)cn2)c2cccc(OCc3c(Cl)cc(F)cc3[C@H](C)N3CC(C)CC3=O)c2n1] | 511.4 |

TABLE 1-continued

Example Compounds Nos. 13 to 107

| Cpd No. | Structure | Mass# |
|---|---|---|
| 63. | 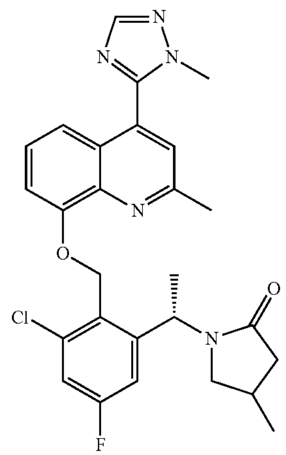 [SMILES: Cc1cc(-c2ncnn2C)c2cccc(OCc3c(Cl)cc(F)cc3[C@H](C)N3CC(C)CC3=O)c2n1] | 508.0 |
| 64. | 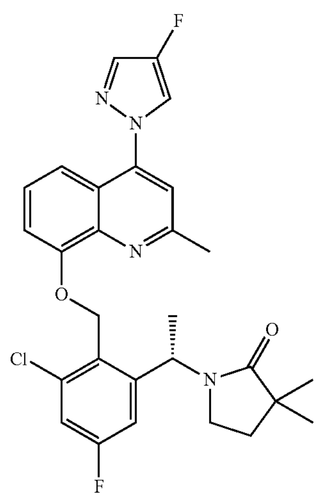 [SMILES: Cc1cc(-n2cc(F)cn2)c2cccc(OCc3c(Cl)cc(F)cc3[C@H](C)N3CCC(C)(C)C3=O)c2n1] | 525.5 |
| 65. | 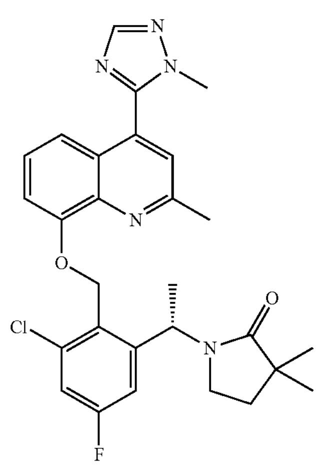 [SMILES: Cc1cc(-c2ncnn2C)c2cccc(OCc3c(Cl)cc(F)cc3[C@H](C)N3CCC(C)(C)C3=O)c2n1] | 522.2 |
| 66. | 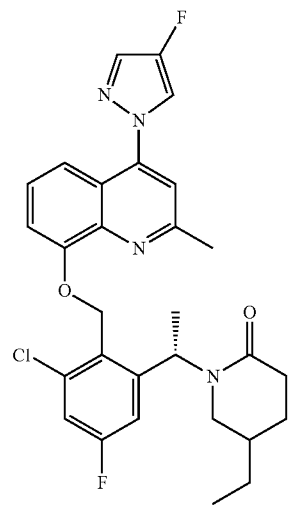 [SMILES: CCC1CCC(=O)N([C@@H](C)c2cc(F)cc(Cl)c2COc2cccc3c(-n4cc(F)cn4)cc(C)nc23)C1] | 539.5 |
| 67. | 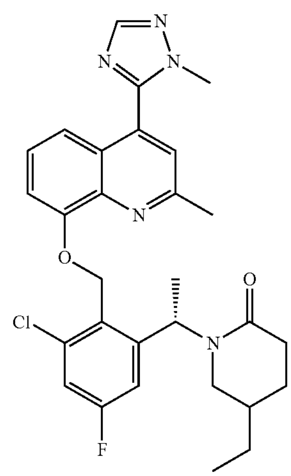 [SMILES: CCC1CCC(=O)N([C@@H](C)c2cc(F)cc(Cl)c2COc2cccc3c(-c4ncnn4C)cc(C)nc23)C1] | 536.1 |
| 68. | 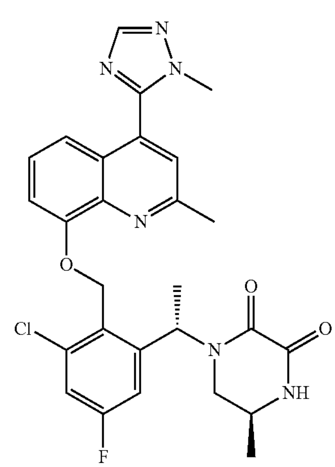 [SMILES: Cc1cc(-c2ncnn2C)c2cccc(OCc3c(Cl)cc(F)cc3[C@H](C)N3C[C@H](C)NC(=O)C3=O)c2n1] | 537.1 |

TABLE 1-continued

Example Compounds Nos. 13 to 107

| Cpd No. | Structure | Mass# |
|---|---|---|
| 69. | 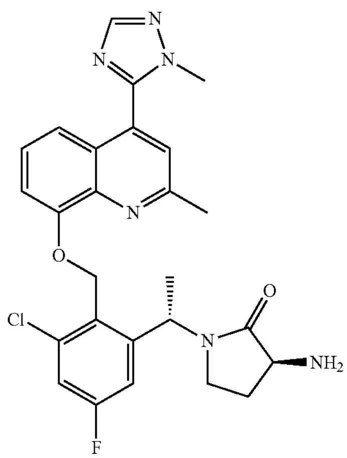 [SMILES: Cc1cc(-c2ncnn2C)c2cccc(OCc3c(Cl)cc(F)cc3[C@H](C)N3CC[C@H](N)C3=O)c2n1] | 510.2 |
| 70. | Diastereomer A | 525.1 |
| 71. | Diastereomer B | 525.0 |
| 72. | 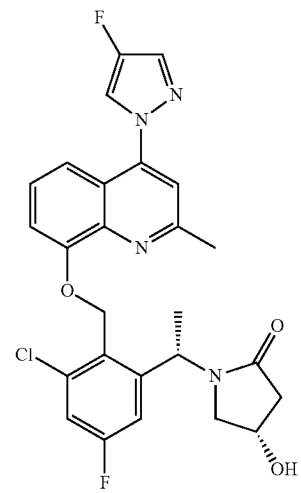 [SMILES: Cc1cc(-n2cc(F)cn2)c2cccc(OCc3c(Cl)cc(F)cc3[C@H](C)N3C[C@@H](O)CC3=O)c2n1] | 513.4 |
| 73. | 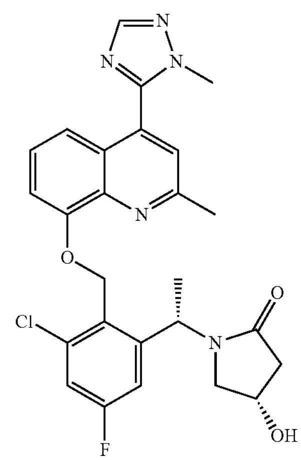 [SMILES: Cc1cc(-c2ncnn2C)c2cccc(OCc3c(Cl)cc(F)cc3[C@H](C)N3C[C@@H](O)CC3=O)c2n1] | 510.1 |
| 74. | 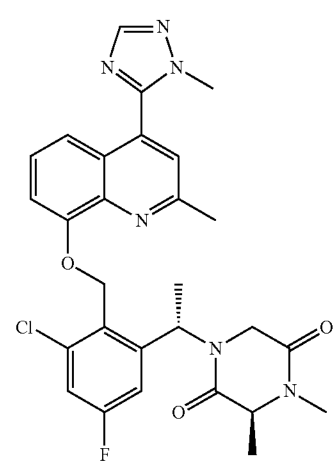 [SMILES: Cc1cc(-c2ncnn2C)c2cccc(OCc3c(Cl)cc(F)cc3[C@H](C)N3CC(=O)N(C)[C@@H](C)C3=O)c2n1] | 552.3 |

TABLE 1-continued

Example Compounds Nos. 13 to 107

| Cpd No. | Structure | Mass# |
|---|---|---|
| 75. | 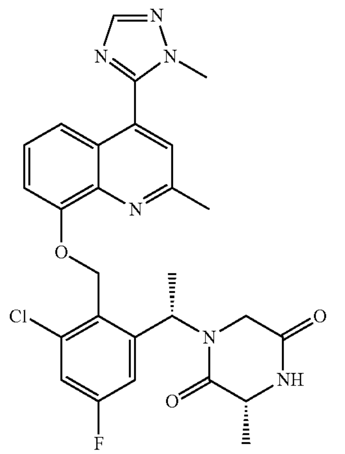 [SMILES: Cc1cc(-c2ncnn2C)c2cccc(OCc3c(Cl)cc(F)cc3[C@H](C)N3CC(=O)N[C@H](C)C3=O)c2n1] | 537.3 |
| 76. | 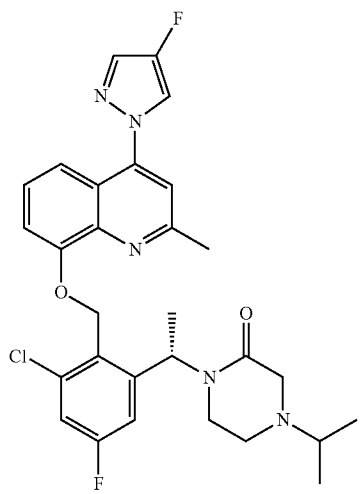 [SMILES: Cc1cc(-n2cc(F)cn2)c2cccc(OCc3c(Cl)cc(F)cc3[C@H](C)N3CCN(C(C)C)CC3=O)c2n1] | 554.9 |
| 77. | 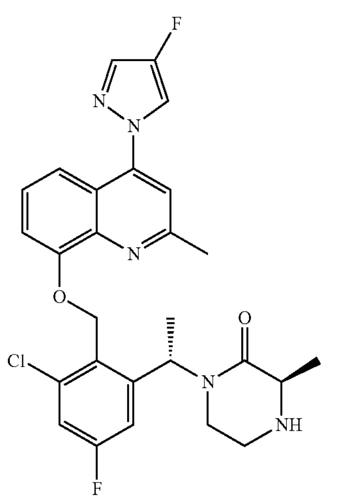 | 526.2 |
| 78. | | 554.4 |
| 79. | | 626.1 |
| 80. | | 626.2 |

TABLE 1-continued

Example Compounds Nos. 13 to 107

| Cpd No. | Structure | Mass# |
|---|---|---|
| 81. | 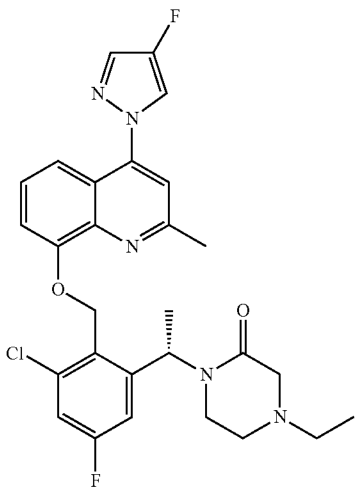 [SMILES: CCN1CCN([C@@H](C)c2cc(F)cc(Cl)c2COc2cccc3c(-n4cc(F)cn4)cc(C)nc23)C(=O)C1] | 540.1 |
| 82. | 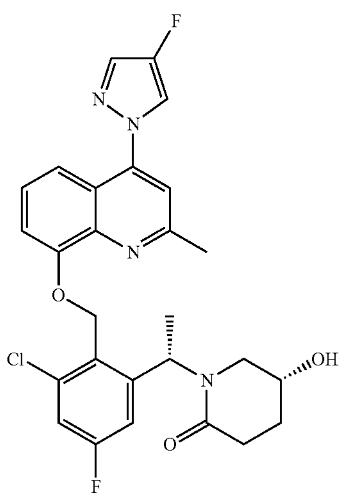 [SMILES: Cc1cc(-n2cc(F)cn2)c2cccc(OCc3c(Cl)cc(F)cc3[C@H](C)N3C[C@H](O)CCC3=O)c2n1] | 527.0 |
| 83. | 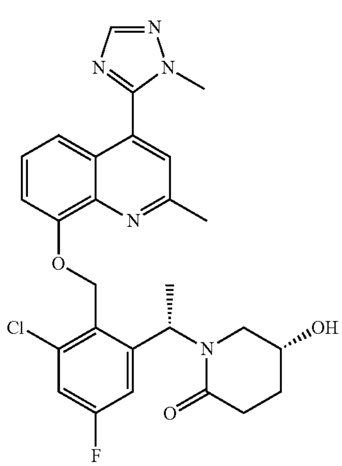 [SMILES: Cc1cc(-c2ncnn2C)c2cccc(OCc3c(Cl)cc(F)cc3[C@H](C)N3C[C@H](O)CCC3=O)c2n1] | 524.1 |
| 84. | 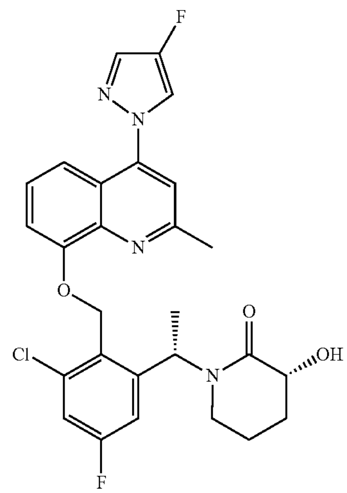 [SMILES: Cc1cc(-n2cc(F)cn2)c2cccc(OCc3c(Cl)cc(F)cc3[C@H](C)N3CCC[C@@H](O)C3=O)c2n1] | 527.1 |
| 85. | 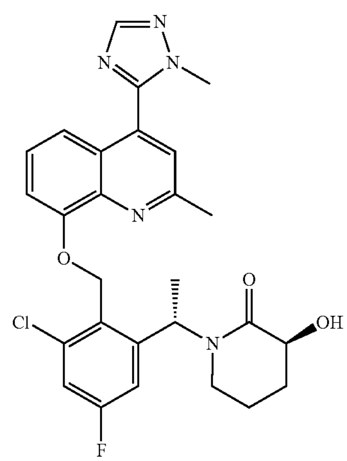 [SMILES: Cc1cc(-c2ncnn2C)c2cccc(OCc3c(Cl)cc(F)cc3[C@H](C)N3CCC[C@H](O)C3=O)c2n1] | 524.2 |
| 86. | 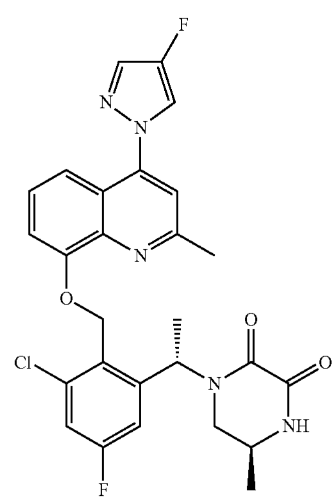 [SMILES: Cc1cc(-n2cc(F)cn2)c2cccc(OCc3c(Cl)cc(F)cc3[C@H](C)N3C[C@H](C)NC(=O)C3=O)c2n1] | 540.1 |

TABLE 1-continued

Example Compounds Nos. 13 to 107

| Cpd No. | Structure | Mass# |
|---|---|---|
| 87. | 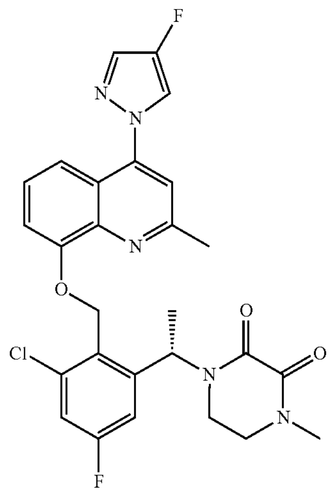 [SMILES: Cc1cc(-n2cc(F)cn2)c2cccc(OCc3c(Cl)cc(F)cc3[C@H](C)N3CCN(C)C(=O)C3=O)c2n1] | 540.1 |
| 88. | 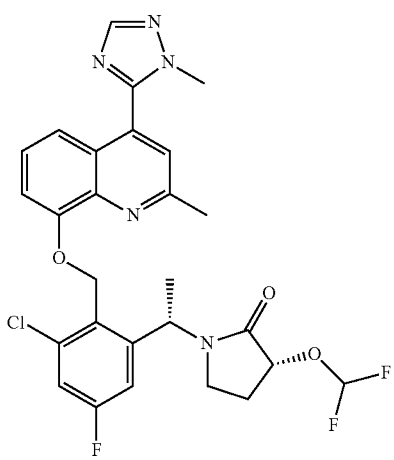 [SMILES: Cc1cc(-c2ncnn2C)c2cccc(OCc3c(Cl)cc(F)cc3[C@H](C)N3CC[C@@H](OC(F)F)C3=O)c2n1] | 560.0 |
| 89. | 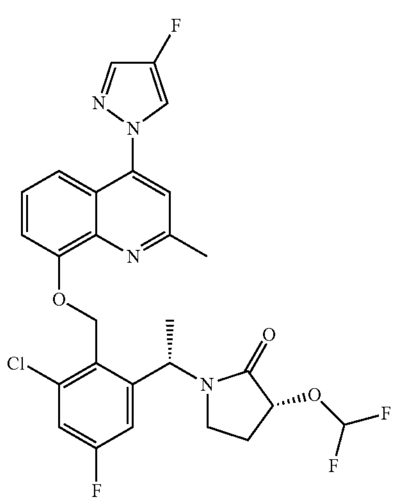 [SMILES: Cc1cc(-n2cc(F)cn2)c2cccc(OCc3c(Cl)cc(F)cc3[C@H](C)N3CC[C@@H](OC(F)F)C3=O)c2n1] | 563.0 |
| 90. | | 554.0 |
| 91. | | 512.1 |
| 92. | | 540.2 |

TABLE 1-continued

Example Compounds Nos. 13 to 107

| Cpd No. | Structure | Mass# |
|---|---|---|
| 93. | 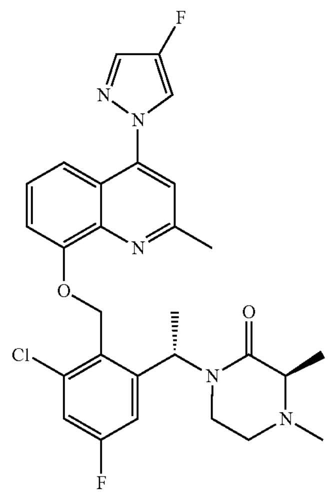 [SMILES: Cc1cc(-n2cc(F)cn2)c2cccc(OCc3c(Cl)cc(F)cc3[C@H](C)N3CCN(C)[C@H](C)C3=O)c2n1] | 540.1 |
| 94. | 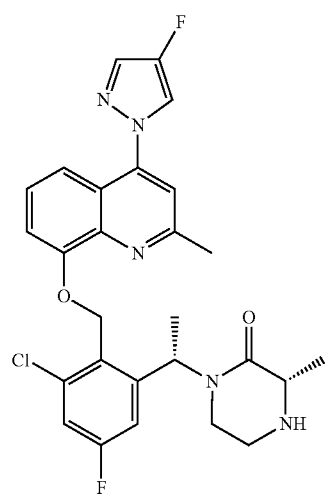 [SMILES: Cc1cc(-n2cc(F)cn2)c2cccc(OCc3c(Cl)cc(F)cc3[C@H](C)N3CCN[C@@H](C)C3=O)c2n1] | 526.1 |
| 95. | 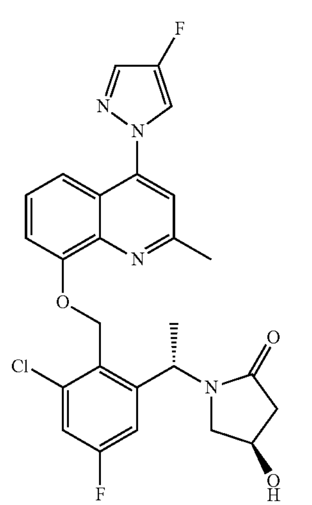 [SMILES: Cc1cc(-n2cc(F)cn2)c2cccc(OCc3c(Cl)cc(F)cc3[C@H](C)N3C[C@H](O)CC3=O)c2n1] | 513.0 |
| 96. | | 510.0 |
| 97. | | 540.9 |
| 98. | | 538.2 |

TABLE 1-continued

Example Compounds Nos. 13 to 107

| Cpd No. | Structure | Mass# |
|---|---|---|
| 99. | 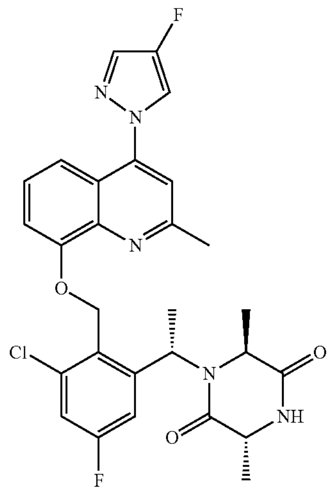 [SMILES: Cc1cc(-n2cc(F)cn2)c2cccc(OCc3c(Cl)cc(F)cc3[C@H](C)N3C(=O)[C@@H](C)NC(=O)[C@@H]3C)c2n1] | 555.3 |
| 100. | 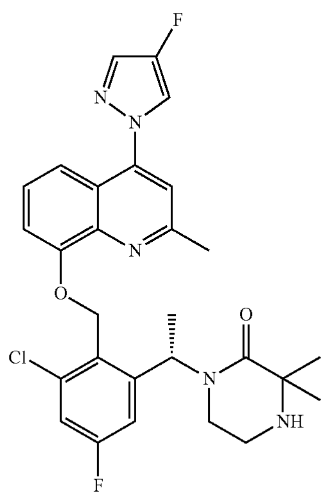 [SMILES: Cc1cc(-n2cc(F)cn2)c2cccc(OCc3c(Cl)cc(F)cc3[C@H](C)N3CCNC(C)(C)C3=O)c2n1] | 540.2 |
| 101. | 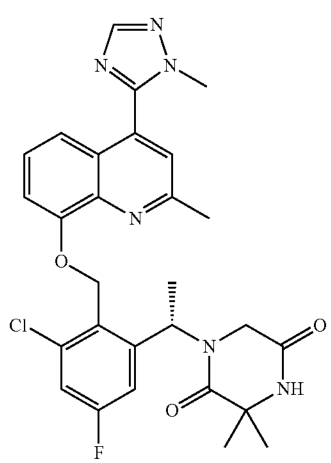 [SMILES: Cc1cc(-c2ncnn2C)c2cccc(OCc3c(Cl)cc(F)cc3[C@H](C)N3CC(=O)NC(C)(C)C3=O)c2n1] | 551.1 |
| 102. | | 554.0 |
| 103. | | 554.0 |
| 104. | | 551.0 |

TABLE 1-continued

Example Compounds Nos. 13 to 107

| Cpd No. | Structure | Mass# |
|---|---|---|
| 105. | 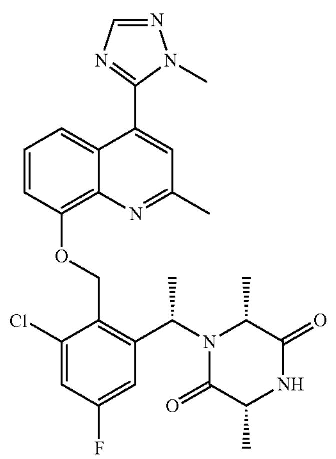 [SMILES: Cc1cc(-c2ncnn2C)c2cccc(OCc3c(Cl)cc(F)cc3[C@H](C)N3C(=O)[C@@H](C)NC(=O)[C@H]3C)c2n1] | 551.8 |
| 106. | 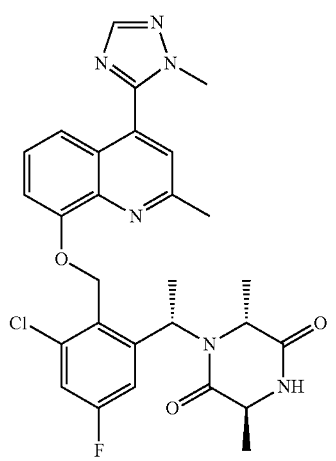 [SMILES: Cc1cc(-c2ncnn2C)c2cccc(OCc3c(Cl)cc(F)cc3[C@H](C)N3C(=O)[C@H](C)NC(=O)[C@H]3C)c2n1] | 551.8 |
| 107. | 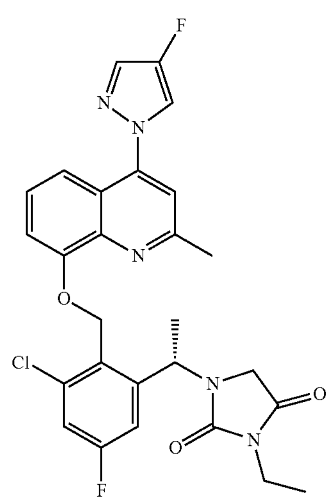 [SMILES: CCN1C(=O)CN([C@@H](C)c2cc(F)cc(Cl)c2COc2cccc3c(-n4cc(F)cn4)cc(C)nc23)C1=O] | 540.2 |

Mass: The mass spectrometry data (from liquid chromatography mass spectrometry spectra) are indicated (m/z) and represent the values for the protonated molecular ions [M + H⁺]

*Absolute configuration at indicated atom has not been determined, but respective stereoisomer was isolated in pure form.

Example 14: Antagonistic Activity of Test Compounds Towards Human B2R

The following cell-based human bradykinin B2 receptor calcium mobilization (hB2R-CaM) assay was used to determine the antagonistic activity of compounds selected from the example compounds Nos. 1 to 107 towards human bradykinin B2 receptor (hB2R). The assay is defined herein as a standard in vitro B2 receptor activity assay, which can be used to determine $IC_{50}$ values of the compounds according to the present invention, e. g. the compounds shown in Examples 1-13.

The antagonistic activity of compounds according to the present invention was investigated with the hB2R-CaM assay using the B2 Bradykinin Receptor Stable Cell Line HTS041C (Eurofins, St. Charles MO) and the FLIPR Calcium 6 Assay Kit (Molecular Devices, Wokingham, UK) according to the instructions of the providers. CaM assay measurements were performed with a Flexstation 3 System (Molecular Devices) which allows the precise addition of compounds (B2R antagonists) and bradykinin (B2R agonist) to the cells and adjacent continuous recording of the time-dependent CaM assay signals.

Cell Culture, Plating and Starvation:

HTS041C cells were cultured in high glucose DMEM cell culture medium (Lonza) supplemented with 10% heat-inactivated FBS (PAN Biotech), 10 mM HEPES, Penicillin/Streptomycin (200 U/mL, 200 µg/mL), 1x non-essential amino acids (Lonza), and 250 µg/mL G418 (Invivogen) in cell incubator at 37° C. in a 5% $CO_2$ atmosphere. One day before the CaM assay experiments cells were seeded in 200 µL DMEM cell culture medium with reduced FBS (5%) and without G418 on clear bottom black 96 well plates (ThermoFisher #165305). Cell starvation was carried out by incubation (37° C., 5% $CO_2$) of 70.000 cells/well for 24 h to 28 h. Immediately prior calcium dye-loading the medium was carefully aspirated and cells were washed with Hank's balanced salt solution (HBSS, Gibco) containing $Ca^{2+}$, $Mg^{2+}$ and 20 mM HEPES, adjusted to pH 7.4 (HBSS+).

Calcium Dye Loading of the Cells:

For calcium dye-loading one FLIPR 6 assay aliquot was dissolved in 20 mL HBSS+. 150 µL of the dye loading solution was added to cell plate and incubated for 120 min at 37° C. and 5% $CO_2$. After dye loading the cell plate was immediately transferred to the pre-warmed (37° C.) Flexstation 3 System for CaM assaying.

Intracellular Calcium Mobilization Assay (CaM Assay):

Freshly prepared compound (B2 receptor antagonists) dilution series (8 pt, n=2) and bradykinin (B2 receptor agonist) solution in non-binding plates (Costar) were transferred to the Flexstation System (source plate) shortly before starting the experiment. Bradykinin was added in EC80 concentration determined in n>3 preliminary experiments with 8 pt concentration response curves (n=8)). CaM assay was executed by Flexstation 3 System starting with recording of calcium-sensitive dye fluorescence in bottom-read Flex modus with ex/em=485 nm/525 nm, cut off(em)=515 nm After 20 s, 50 µL of 4-fold concentrated compound dilutions were added to the cells resulting in a final DMSO (Sigma) concentration of 0.1% in the cell plate. CaM signals were monitored for 80 s after additions for detection of potential agonistic activities. Prior to bradykinin stimulus compound- and vehicle-treated cells were incubated for 25 min at 37° C. within the Flexstation System. Then 50 µL of a 5-fold concentrated bradykinin solution (HBSS+, 0.1%

DMSO) was added to trigger CaM signals (Read out: Max-Min values) which were measured for 80 s post bradykinin stimulus.

IC50 determinations were performed by 4 parameter logistic model curve fitting of the 8 pt (n=2) compound concentration response curves using XLFIT (IDBS) software.

Measurement Results:

Example Compounds Nos. 4, 5, 11, 12, 15, 26, 27, 30, 34, 37, 40, 41, 44, 45, 46, 48, 49, 50, 53, 55, 60, 61, 63, 67, 68, 72, 73, 76, 81, 82, 86, 87, 88, 91, 92, 93, 94, 97, 98 and 104 showed an IC50-value of equal to or below 10 nM towards human bradykinin B2 receptor (hB2R).

Example Compounds Nos. 1, 2, 3, 6, 7, 8, 9, 10, 13, 14, 16, 17, 18, 19, 20, 21, 22, 23, 24, 25, 29, 32, 33, 35, 36, 38, 39, 42, 43, 47, 51, 54, 56, 57, 58, 59, 62, 64, 65, 66, 69, 70, 71, 74, 75, 77, 78, 83, 84, 89, 90, 95, 96, 99, 100, 101, 102, 103, 105, 106 and 107 showed an $IC_{50}$-value between 11 and 100 nM towards human bradykinin B2 receptor (hB2R).

Example Compounds Nos. 28, 31, 52, 79, 80 and 85 showed an $IC_{50}$-value between 101 nM and 500 nM towards human bradykinin B2 receptor (hB2R).

None of the tested compounds showed any toxic effects in the cell-based test system.

The features of the present invention disclosed in the specification and/or the claims may both separately and in any combination thereof be material for realizing the invention in various forms thereof.

The invention claimed is:

1. A compound of the general formula (I):

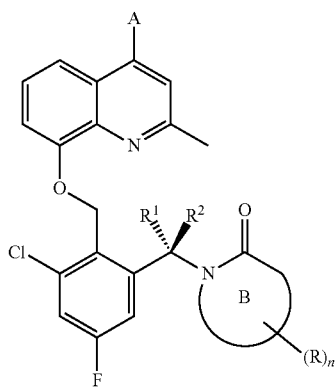

(I)

or a salt thereof, wherein
A represents a group:

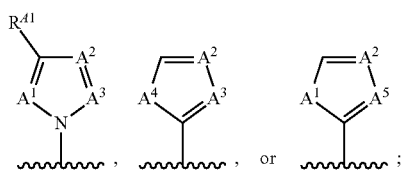

$A^1$ is N, or CH;
$A^2$ is N, or C—$R^{A2}$;
$A^3$ is N, or C—$R^{A3}$;
$A^4$ is NH, O, or S;
$A^5$ is N—$R^{A5}$;
$R^{A1}$ represents a hydrogen atom or a methyl group;

$R^{A2}$ and $R^{A3}$ each, independently of one another, represents a hydrogen atom, halogen atom, OH, CN, $NH_2$; $(C_1-C_3)$ alkyl, which may be substituted by one or more, identical or different, group(s) selected from a halogen atom, OH, =O, and $NH_2$; $(C_1-C_3)$ alkoxy, which may be substituted by one or more, identical or different, group(s) selected from a halogen atom, OH, =O, and $NH_2$; $(C_2-C_5)$ alkoxyalkyl, which may be substituted by one or more, identical or different, group(s) selected from a halogen atom, OH, =O, and $NH_2$; $C(O)NR^{A6}R^{A7}$; or $NR^{A6}R^{A7}$;

$R^{A5}$, $R^{A6}$ and $R^{A7}$ each, independently of one another, represents a hydrogen atom or a $(C_1-C_3)$ alkyl group, which may be substituted by one or more, identical or different, group(s) selected from a halogen atom, OH, =O, and $NH_2$;

$R^1$ represents a $(C_1-C_3)$ alkyl or $(C_2-C_5)$ alkoxyalkyl group, which alkyl group or alkoxyalkyl group may be substituted by one or more, identical or different, group(s) selected from a deuterium atom, halogen atom, OH, =O, and $NH_2$;

$R^2$ represents a hydrogen atom or a deuterium atom;

B represents a 5- or 6-membered nitrogen-containing heterocycloalkyl group having at least one oxo substituent and n substituents R, wherein n denotes the number 0, 1, 2, 3, 4 or 5; and each R, at each occasion independently, represents a halogen atom, OH, $NR^{C1}R^{C2}$, =O, G, OG, or a $(C_3-C_5)$ cycloalkyl group;

$R^{C1}$ and $R^{C2}$ each, independently of one another, represents a hydrogen atom or a $(C_1-C_3)$ alkyl group;

G represents a $(C_1-C_6)$ alkyl group, in which 1 to 5 H atoms may, at each occasion independently, be replaced by a halogen atom, =O, $OR^{G1}$, or $NR^{G2}R^{G3}$, and/or in which one $CH_2$ group, or two non-adjacent $CH_2$ groups, may be replaced by O, C(O), OC(O), C(O)O, C(O)NH, NHC(O), NH, S, SO, and/or $SO_2$;

$R^{G1}$, $R^{G2}$, and $R^{G3}$ each, independently of one another, represents a hydrogen atom, $(C_1-C_3)$ alkyl, $(C_1-C_3)$ haloalkyl, $(C_1-C_3)$ hydroxyalkyl, $(C_1-C_3)$ heteroalkyl, or $(C_3-C_5)$ cycloalkyl group.

2. The compound or salt according to claim 1, wherein $R^1$ represents a $(C_1-C_2)$ alkyl or $(C2-C_4)$ alkoxyalkyl group, which alkyl group or alkoxyalkyl group may be substituted by one or more, identical or different, group(s) selected from a halogen atom and OH.

3. The compound or salt according to claim 1, wherein the oxo-substituted, nitrogen-containing heterocycloalkyl group B represents the 5-membered group (HetB1):

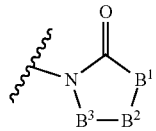

(HetB1)

wherein
$B^1$ is N—$R^{B1}$, O or $CR^{B2}R^{B3}$;
$B^2$ is $CR^{B4}R^{B5}$; and
$B^3$ is $CR^{B6}R^{B7}$;
$R^{B1}$ represents a hydrogen atom, G, or a $(C_3-C_5)$ cycloalkyl group;
$R^{B2}$ and $R^{B3}$ each, independently of one another, represents a hydrogen atom, a halogen atom, OH, G, OG, or $NR^{C1}R^{C2}$;

$R^{B4}$ and $R^{B5}$ each, independently of one another, represents a hydrogen atom, a halogen atom, OH, G, or OG; or $R^{B4}$ and $R^{B5}$ are taken together to form =O;

$R^{B6}$ and $R^{B7}$ each, independently of one another, represents a hydrogen atom, a halogen atom, or G; and G, $R^{C1}$ and $R^{C2}$ are defined as in claim 1.

4. The compound or salt according to claim 3, wherein $B^1$ to $B^3$ are as defined in any one of the following (i) to (iii):
   (i) $B^1$ is N—$R^{B1}$; $B^2$ is C=O or $CH_2$; and $B^3$ is $CH_2$ or $CH(CH_3)$;
   (ii) $B^1$ is O; $B^2$ is $CR^{B4}R^{B5}$; and $B^3$ is $CH_2$ or $CH(CH_3)$; or
   (iii) $B^1$ is $CR^{B2}R^{B3}$; $B^2$ is $CR^{B4}R^{B5}$; and $B^3$ is $CH_2$; and $R^{B1}$; $R^{B2}$, $R^{B3}$, $R^{B4}$ and $R^{B5}$ are as defined in claim 3.

5. The compound or salt according to claim 3, wherein the 5-membered group (HetB1) is selected from:

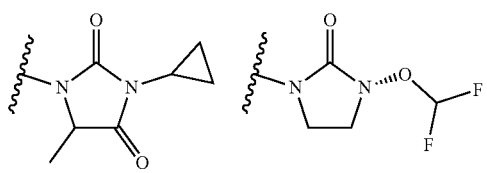
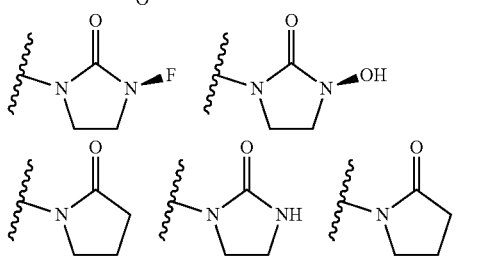
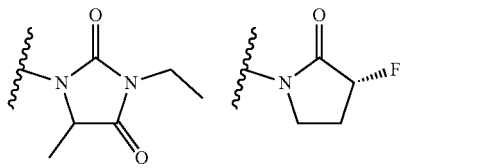
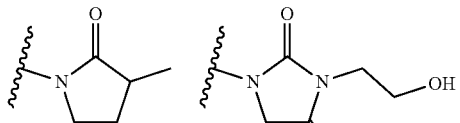
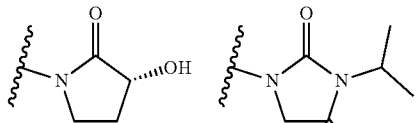
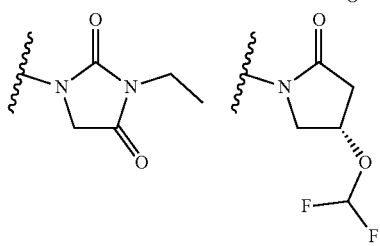
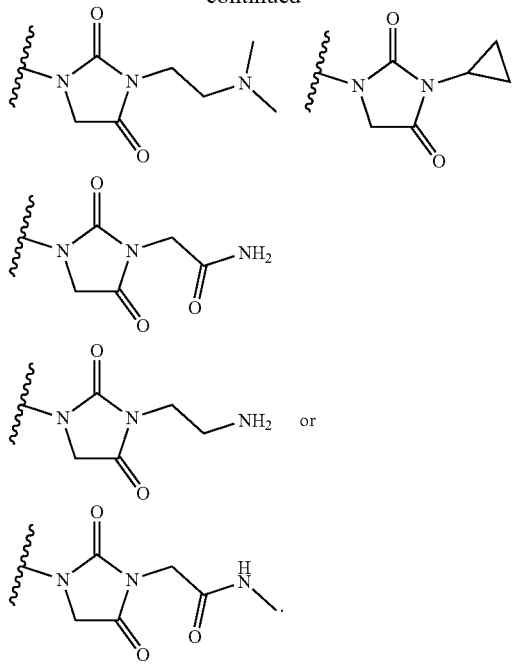

6. The compound or salt according to claim 1, wherein the oxo-substituted, nitrogen-containing heterocycloalkyl group B represents the 6-membered group (HetB2):

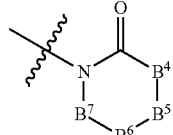

(HetB2)

wherein
$B^4$ is C=O or $CR^{B11}R^{B12}$;
$B^5$ is N—$R^{B13}$, O or $CR^{B14}R^{B15}$;
$B^6$ is C=O or $CR^{B16}R^{B17}$;
$B^7$ is $CR^{B18}R^{B19}$;
$R^{B11}$, $R^{B12}$, $R^{B14}$, $R^{B15}$, $R^{B16}$, $R^{B17}$, $R^{B18}$ and $R^{B19}$ each, independently of one another, represents a hydrogen atom, halogen atom, G, OH, OG, ($C_3$-$C_5$) cycloalkyl, or an O($C_3$-$C_5$) cycloalkyl group;
$R^{B13}$ represents a hydrogen atom, G, or a ($C_3$-$C_5$) cycloalkyl group; and
G is defined as in claim 1.

7. The compound or salt according to claim 6, wherein $B^4$ to $B^6$ are as defined in any one of the following (i) to (v):
   (i) $B^4$ is C=O; $B^5$ is N—$R^{B13}$; and $B^6$ is $CR^{B16}R^{B17}$;
   (ii) $B^4$ is $CR^{B11}R^{B12}$; $B^5$ is N—$R^{B13}$; and $B^6$ is C=O;
   (iii) $B^4$ is $CR^{B11}R^{B12}$; $B^5$ is O; and $B^6$ is $CR^{B16}R^{B17}$;
   (iv) $B^4$ is $CR^{B11}R^{B12}$, $B^5$ is N—$R^{B13}$; and $B^6$ is $CR^{B16}R^{B17}$; or
   (v) $B^4$ is $CR^{B11}R^{B12}$, $B^5$ is $CR^{B14}R^{B15}$; and $B^6$ is $CR^{B16}R^{B17}$;

$B^7$ represents $CH_2$ or $CH(CH_3)$; and
$R^{B11}$, $R^{B12}$, $R^{B13}$, $R^{B14}$, $R^{B15}$, $R^{B16}$, $R^{B17}$, $R^{B18}$ and $R^{B19}$ are defined as in claim 6.

8. The compound or salt according to claim 6, wherein the 6-membered group (HetB2) is selected from:

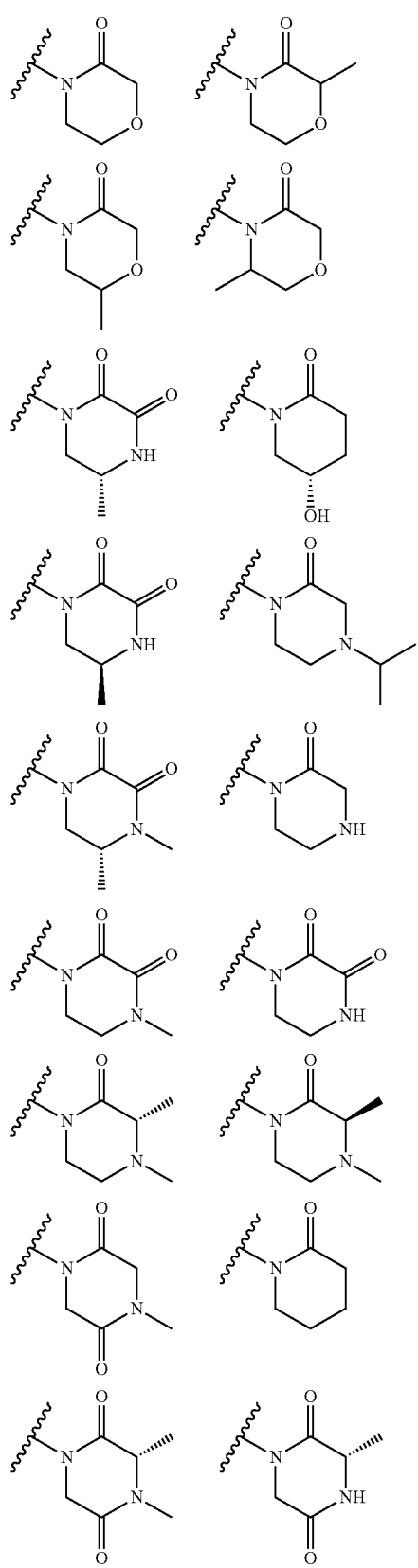
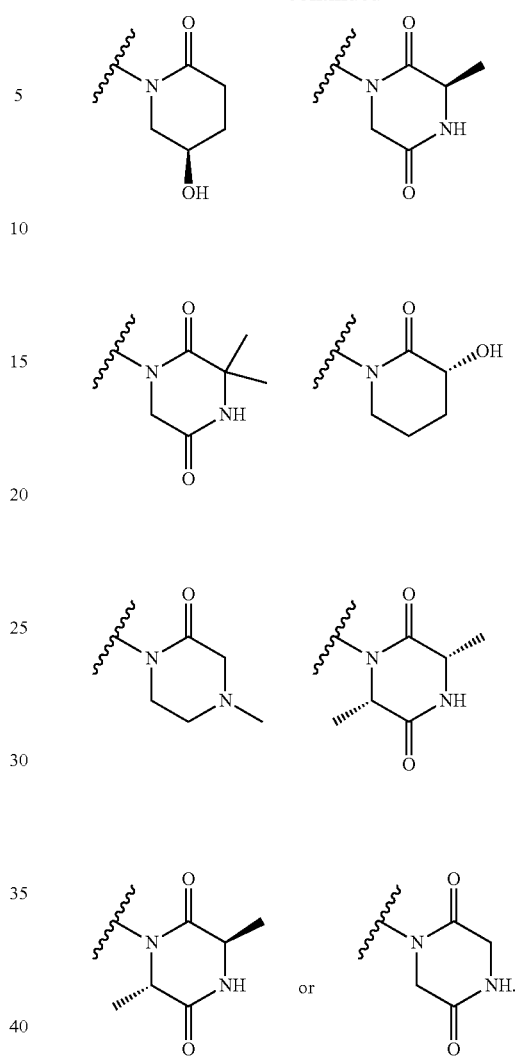
9. The compound or salt according to claim 1, wherein the compound is selected from the group:
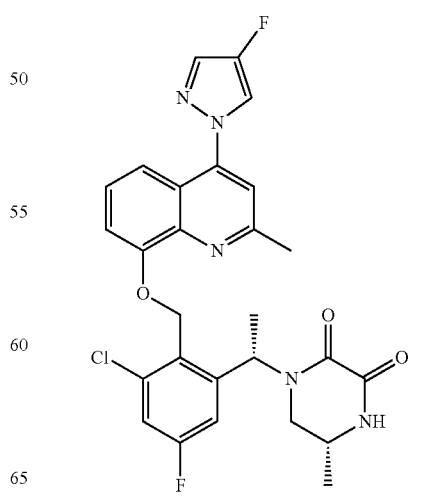

97
-continued
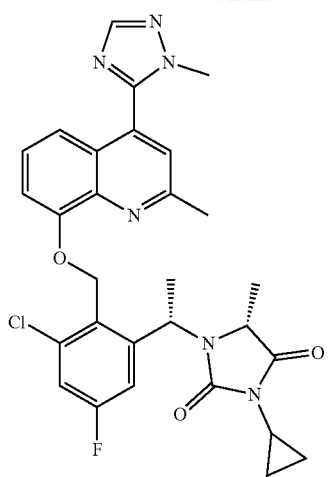
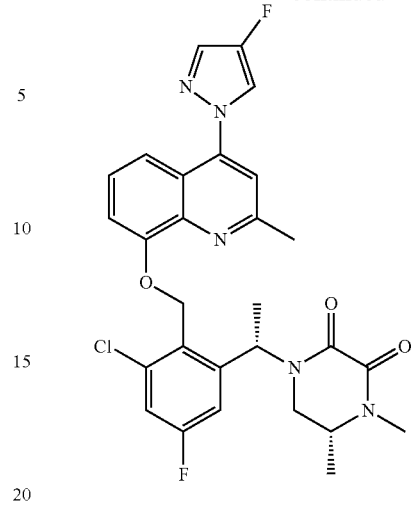
98
-continued
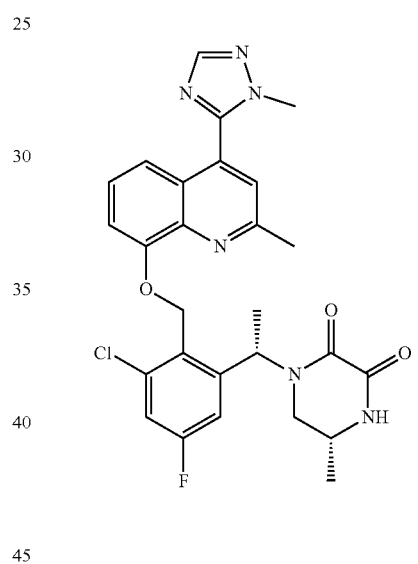
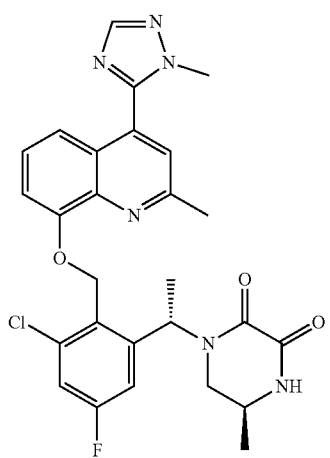
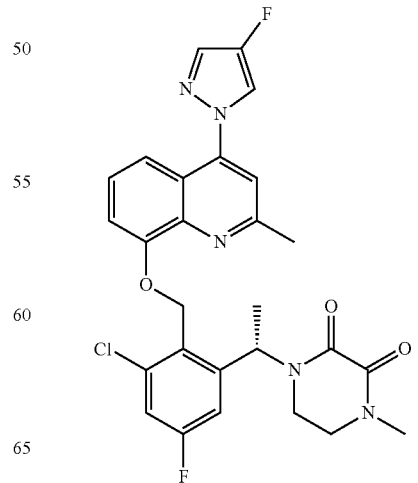

99
-continued
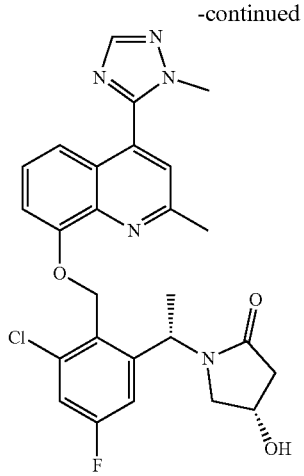
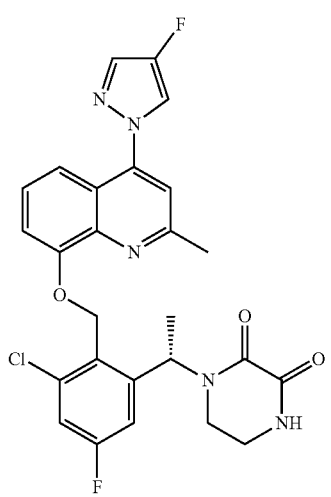
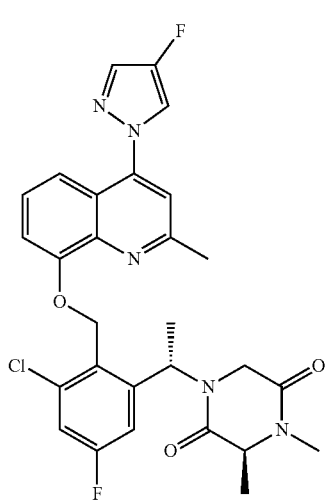
100
-continued
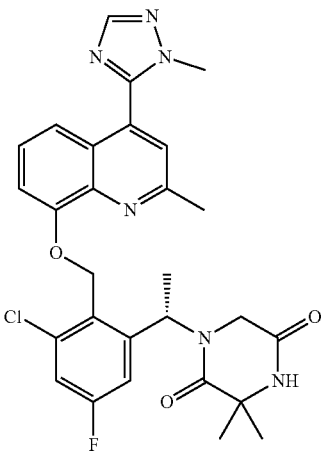
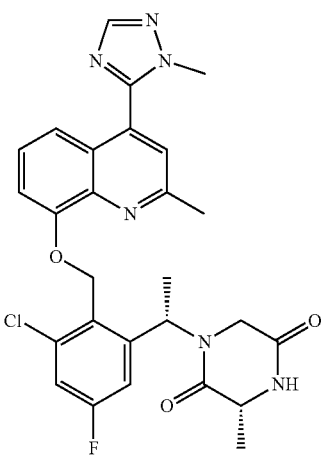
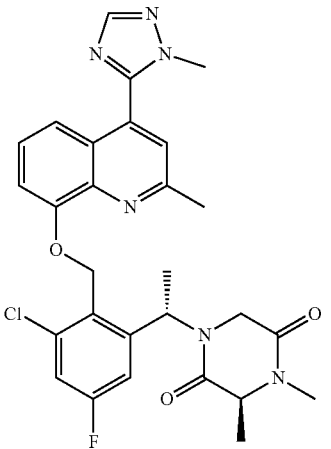

101
-continued
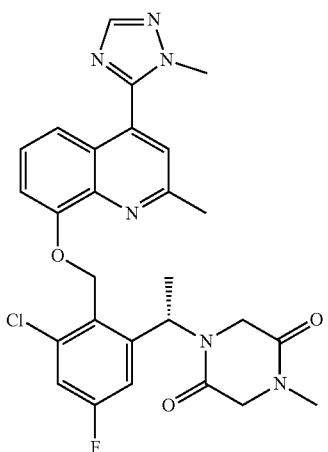
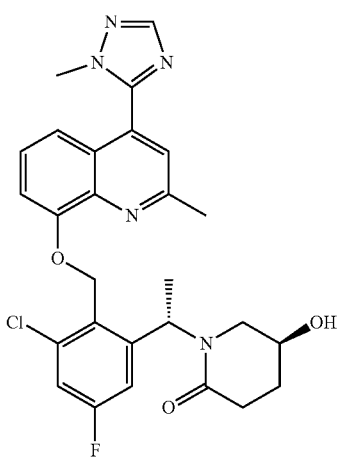
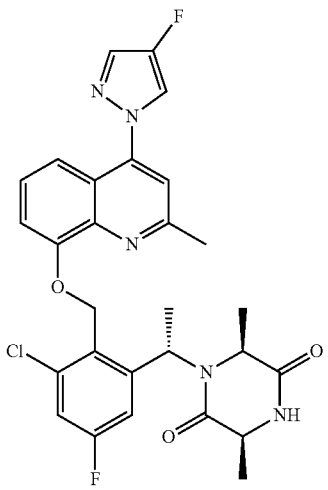
102
-continued
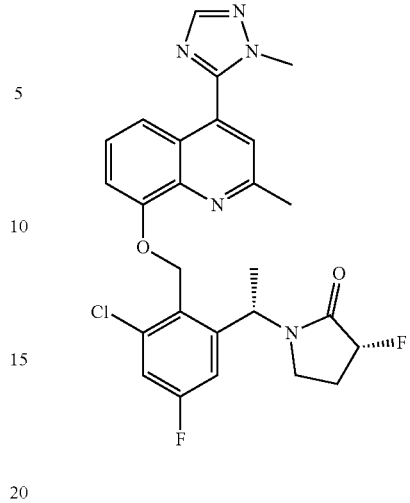
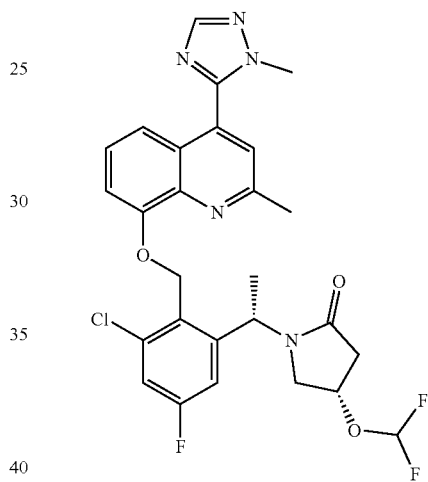
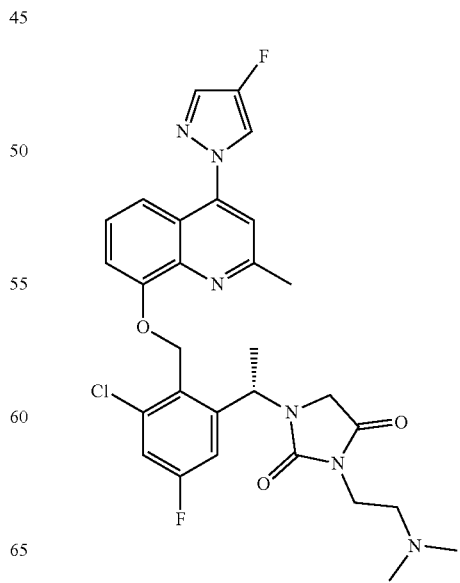

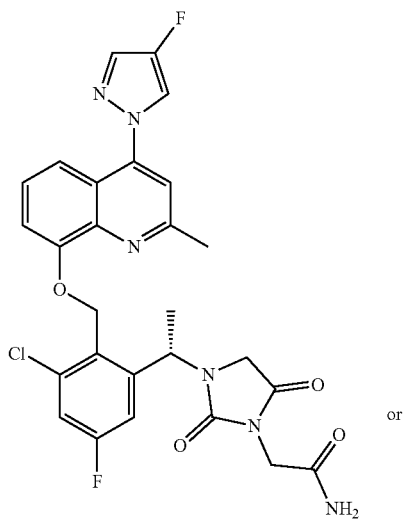

or

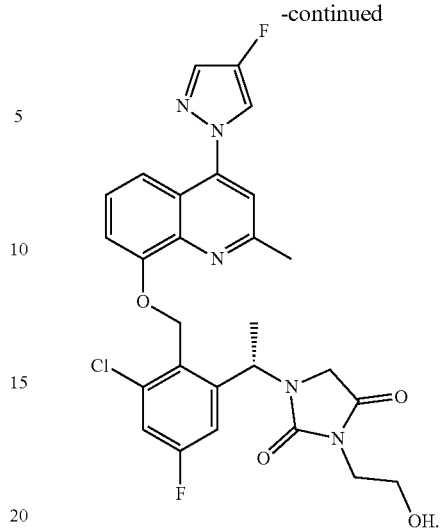

10. A pharmaceutical composition comprising a compound, or a pharmaceutically acceptable salt thereof, according to claim 1 and at least one carrier substance, excipient and/or adjuvant.

11. The pharmaceutical composition according to claim 10, wherein the pharmaceutical composition is formulated as an aerosol, a cream, a gel, a pill, a capsule, a syrup, a solution, a transdermal patch or a pharmaceutical delivery device.

12. A combination preparation containing at least a compound, or a pharmaceutically acceptable salt thereof, according to claim 1 and at least one further active pharmaceutical ingredient.

\* \* \* \* \*

UNITED STATES PATENT AND TRADEMARK OFFICE
CERTIFICATE OF CORRECTION

PATENT NO. : 12,312,330 B2  
APPLICATION NO. : 17/530967  
DATED : May 27, 2025  
INVENTOR(S) : Christoph Gibson et al.

Page 1 of 1

It is certified that error appears in the above-identified patent and that said Letters Patent is hereby corrected as shown below:

In the Claims

Column 91, Claim 1, Line 57, replace " 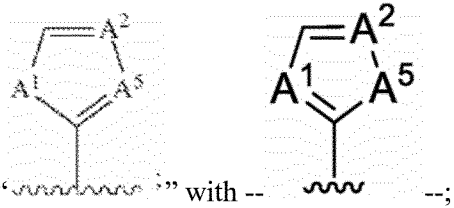 " with -- --;

Column 93, Claim 4, Line 9, replace "(ill)" with --(iii)--;

Claim 5, Line 25, replace " 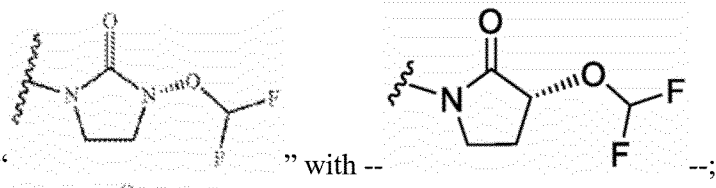 " with -- --;

Claim 5, Line 30, replace " 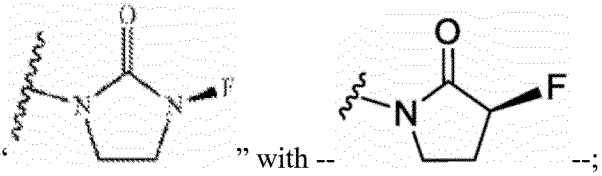 " with -- --;

Claim 5, Line 30, replace " 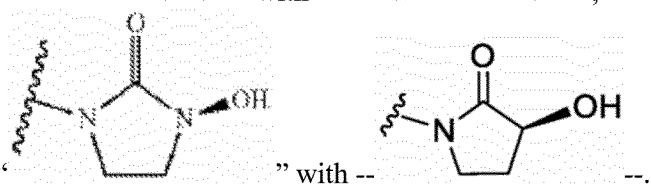 " with -- --.

Signed and Sealed this  
Second Day of September, 2025

Coke Morgan Stewart  
*Acting Director of the United States Patent and Trademark Office*